US009555094B2

(12) United States Patent
Kuroda et al.

(10) Patent No.: US 9,555,094 B2
(45) Date of Patent: Jan. 31, 2017

(54) ISOLATED NUCLEIC ACID FOR THE PRODUCTION OF A VACCINE AGAINST VIRUS

(71) Applicant: THE INSTITUTE OF BIOLOGICAL RESOURCES, Nago (JP)

(72) Inventors: Kazumichi Kuroda, Tokyo (JP); Shigeo Sugita, Koga (JP); Kuniaki Nerome, Nago (JP); Reiko Nerome, Nago (JP)

(73) Assignee: The Institute of Biological Resources, Tokyo (JP)

( * ) Notice: Subject to any disclaimer, the term of this patent is extended or adjusted under 35 U.S.C. 154(b) by 0 days.

(21) Appl. No.: 14/413,700

(22) PCT Filed: Jul. 23, 2013

(86) PCT No.: PCT/JP2013/069935
§ 371 (c)(1),
(2) Date: Jan. 9, 2015

(87) PCT Pub. No.: WO2014/017493
PCT Pub. Date: Jan. 30, 2014

(65) Prior Publication Data
US 2015/0140103 A1 May 21, 2015

(30) Foreign Application Priority Data

Jul. 23, 2012 (JP) ................ 2012-162413

(51) Int. Cl.
| *A61K 39/145* | (2006.01) |
| *C07K 14/005* | (2006.01) |
| *A61K 39/29* | (2006.01) |
| *C12N 7/00* | (2006.01) |
| *A61K 39/12* | (2006.01) |
| *A01K 67/033* | (2006.01) |
| *C12N 15/85* | (2006.01) |

(52) U.S. Cl.
CPC ......... *A61K 39/145* (2013.01); *A01K 67/0335* (2013.01); *A61K 39/12* (2013.01); *A61K 39/29* (2013.01); *C07K 14/005* (2013.01); *C12N 7/00* (2013.01); *C12N 15/8509* (2013.01); *A01K 2227/703* (2013.01); *A01K 2267/01* (2013.01); *C12N 2710/00043* (2013.01); *C12N 2760/16122* (2013.01); *C12N 2760/16134* (2013.01); *C12N 2760/20122* (2013.01); *C12N 2760/20134* (2013.01); *C12N 2770/20034* (2013.01); *C12N 2770/24122* (2013.01); *C12N 2770/24222* (2013.01); *C12N 2770/24234* (2013.01); *C12N 2770/32134* (2013.01); *C12N 2799/026* (2013.01); *C12N 2800/22* (2013.01)

(58) Field of Classification Search
None
See application file for complete search history.

(56) References Cited

U.S. PATENT DOCUMENTS

| 5,547,871 A * | 8/1996 | Black .................... A01N 63/00 435/320.1 |
| 2008/0287651 A1 | 11/2008 | Hiramatsu et al. |
| 2015/0140103 A1* | 5/2015 | Kuroda ................ A61K 39/12 424/489 |

FOREIGN PATENT DOCUMENTS

| CN | 102304529 A | 1/2012 |
| CN | 102321634 A | 1/2012 |
| JP | 03-108480 A | 5/1991 |
| JP | 2000-230931 A | 8/2000 |
| WO | 2005/068495 A1 | 7/2005 |
| WO | 2007/046439 A1 | 4/2007 |

OTHER PUBLICATIONS

Jin et al. (PLoSOne. Dec. 2008; 3 (12): e3933).*
Zhang et al. Machine translation of CN102321634 (Jan. 2012).*
Zhang et al. Machine translation of CN102304529 (Jan 2012).*
Deo et al. (Journal of Virological Methods. 2011; 177: 147-152).*
Shoji et al. (Human Vaccines. Jan./Feb. 2011; 7 (Supply): 41-50).*
Gomez-Casado et al., "Inset larvae biofactories as a platform for influenza vaccine production," Protein Expression and Purification, 2011, 79:35-43.
Li et al., "FMD subunit vaccine produced using a silkworm-baculovirus expression system: Protective efficacy against two type Asia1 isolates in cattle," Veterinary Microbiology, 2011, 149:99-103.
Lee et al., "Production of Classical Swine Fever Virus Envelope Glycoprotein E2 as Recombinant Polyhedra in Baculovirus-Infected Silkworm Larvae," Mol Biotechnol, 2012, 50:211-220.
Feng et al., "Recombinant canine parvovirus-like particles express foreign epitopes in silkworm pupae," Veterinary Microbiology, 2011, 154:49-57.
Yin et al., "Rabies virus nucleoprotein expressed in silkworm pupae at high-levels and evaluation of immune responses in mice," Journal of Biotechnology, 2013, 163:333-338.
Extended European Search Report issued in European Patent Application No. 13822848.1, dated Feb. 23, 2016.
International Search Report for PCT/JP2013/069935, dated Sep. 3, 2013.
Maeda, S. et al., "Production of human α-interferon in silkworm using a baculovirus vector", Nature (Jun. 13, 1985) pp. 592-594, vol. 315.
Nerome, K. et al., "Kaiko ni Okeru Influenza Vaccine no Seisan to Sono Riyoho", Japanese Journal of Bacteriology (1991), p. 71, vol. 46, No. 1, with English-language translation.

* cited by examiner

*Primary Examiner* — Shanon A Foley
(74) *Attorney, Agent, or Firm* — Riverside Law LLP

(57) ABSTRACT

The present invention relates to a nucleic acid for vaccine that has undergone codon optimization for expression in *Bombyx mori*, a vector comprising the nucleic acid, *Bombyx mori* comprising the vector, and a method for producing a vaccine in which they are used.

13 Claims, 47 Drawing Sheets

Fig. 1

| | | | |
|---|---|---|---|
| UUU F 15.3( 6894) | UCU S 12.7( 5718) | UAU Y 13.9( 6250) | UGU C  8.7( 3929) |
| UUC F 24.0(10823) | UCC S 12.0( 5399) | UAC Y 22.0( 9918) | UGC C 11.3( 5094) |
| UUA L 13.1( 5885) | UCA S 13.0( 5846) | **UAA \*  1.4(  633)** | UGA \*  0.6(  276) |
| UUG L 15.8( 7124) | UCG S 11.0( 4969) | UAG \*  0.6(  289) | UGG W 11.7( 5272) |
| | | | |
| CUU L 11.5( 5193) | CCU P 14.0( 6283) | CAU H 10.3( 4656) | CGU R  9.8( 4399) |
| CUC L 14.6( 6570) | CCC P 11.7( 5256) | CAC H 13.8( 6198) | CGC R 10.5( 4711) |
| CUA L  8.8( 3941) | CCA P 13.6( 6110) | CAA Q 18.7( 8409) | CGA R  7.0( 3153) |
| CUG L 18.4( 8268) | CCG P 13.0( 5860) | CAG Q 17.4( 7845) | CGG R  5.4( 2423) |
| | | | |
| AUU I 18.6( 8391) | ACU T 15.6( 7037) | AAU N 20.5( 9230) | AGU S 10.3( 4632) |
| AUC I 20.7( 9321) | ACC T 14.2( 6390) | AAC N 24.9(11200) | AGC S 12.5( 5618) |
| AUA I 15.9( 7173) | ACA T 15.9( 7146) | AAA K 34.0(15283) | AGA R 14.1( 6325) |
| AUG M 23.4(10544) | ACG T 11.9( 5350) | AAG K 28.4(12759) | AGG R  8.9( 4011) |
| | | | |
| GUU V 16.8( 7558) | GCU A 25.3(11368) | GAU D 25.6(11532) | GGU G 21.7( 9761) |
| GUC V 16.7( 7502) | GCC A 19.7( 8860) | GAC D 28.8(12971) | GGC G 18.8( 8443) |
| GUA V 12.4( 5588) | GCA A 14.6( 6556) | GAA E 36.0(16217) | GGA G 21.4( 9636) |
| GUG V 19.4( 8735) | GCG A 13.5( 6066) | GAG E 26.2(11781) | GGG G  7.7( 3465) |

Fig. 2

| | | | | | | | | | |
|---|---|---|---|---|---|---|---|---|---|
| N | AAC | G | GGU | Y | UAC | F | UUC | \* | UAA |
| D | GAC | Q | CAA | W | UGG | P | CCU | B | RAC |
| A | GCU | E | GAA | T | ACA | M | AUG | Z | SAA |
| R | AGA | C | UGC | V | GUG | K | AAA | X | NNN |
| I | AUC | S | UCA | H | CAC | L | CUG | ? | NNN |

Fig. 3-1

| SEQ ID NO: 4 | 1 | ATG GAA AAA ATC GTG CTG CTG TTC ACA ACA ATC GGT CTG GTG AAA | 45 |
| SEQ ID NO: 3 | 1 | Met Glu Lys Ile Val Leu Leu Phe Thr Thr Ile Gly Leu Val Lys | 15 |
| | 46 | TCA GAC CAC ATC TGC ATC GGT TAC CAC GCT AAC AAC TCA ACA GAA | 90 |
| | 16 | Ser Asp His Ile Cys Ile Gly Tyr His Ala Asn Asn Ser Thr Glu | 30 |
| | 91 | CAA GTG GAC ACA ATC ATG GAA AAA AAC GTG ACA GTG ACA CAC GCT | 135 |
| | 31 | Gln Val Asp Thr Ile Met Glu Lys Asn Val Thr Val Thr His Ala | 45 |
| | 136 | CAA GAC ATC CTG GAA AAA ACA CAC AAC GGT AAA CTG TGC GAC CTG | 180 |
| | 46 | Gln Asp Ile Leu Glu Lys Thr His Asn Gly Lys Leu Cys Asp Leu | 60 |
| | 181 | AAC GGT GTG AAA CCT CTG ATC CTG AAA GAC TGC TCA GTG GCT GGT | 225 |
| | 61 | Asn Gly Val Lys Pro Leu Ile Leu Lys Asp Cys Ser Val Ala Gly | 75 |
| | 226 | TGG CTG CTG GGT AAC CCT CTG TGC GAC GAA TTC ATC AAC GTG CCT | 270 |
| | 76 | Trp Leu Leu Gly Asn Pro Leu Cys Asp Glu Phe Ile Asn Val Pro | 90 |
| | 271 | GAA TGG TCA TAC ATC GTG GAA AAA GCT AAC CCT GCT AAC GAC CTG | 315 |
| | 91 | Glu Trp Ser Tyr Ile Val Glu Lys Ala Asn Pro Ala Asn Asp Leu | 105 |
| | 316 | TGC TAC CCT GGT AAC TTC AAC GAC TAC GAA GAA CTG AAA CAC CTG | 360 |
| | 106 | Cys Tyr Pro Gly Asn Phe Asn Asp Tyr Glu Glu Leu Lys His Leu | 120 |
| | 361 | CTG TCA AGA ATC AAC CAC TTC GAA AAA ATC CAA ATC ATC CCT AAA | 405 |
| | 121 | Leu Ser Arg Ile Asn His Phe Glu Lys Ile Gln Ile Ile Pro Lys | 135 |
| | 406 | GAC TCA TGG TCA GAC CAC GAA GCT TCA CTG GGT GTG TCA GCT GCT | 450 |
| | 136 | Asp Ser Trp Ser Asp His Glu Ala Ser Leu Gly Val Ser Ala Ala | 150 |
| | 451 | TGC TCA TAC CAA GGT AAC TCA TCA TTC TTC AGA AAC GTG GTG TGG | 495 |
| | 151 | Cys Ser Tyr Gln Gly Asn Ser Ser Phe Phe Arg Asn Val Val Trp | 165 |

Fig. 3-2

| | | | |
|---|---|---|---|
| SEQ ID NO: 4 cont. 496 | CTG ATC AAA AAA GAC AAC GCT TAC CCT ACA ATC AAA AAA GGT TAC | 540 |
| SEQ ID NO: 3 cont. 166 | Leu Ile Lys Lys Asp Asn Ala Tyr Pro Thr Ile Lys Lys Gly Tyr | 180 |
| 541 | AAC AAC ACA AAC CAA GAA GAC CTG CTG GTG CTG TGG GGT ATC CAC | 585 |
| 181 | Asn Asn Thr Asn Gln Glu Asp Leu Leu Val Leu Trp Gly Ile His | 195 |
| 586 | CAC CCT AAC GAC GAA GCT GAA CAA ACA AGA CTG TAC CAA AAC CCT | 630 |
| 196 | His Pro Asn Asp Glu Ala Glu Gln Thr Arg Leu Tyr Gln Asn Pro | 210 |
| 631 | ACA ACA TAC ATC TCA ATC GGT ACA TCA ACA CTG AAC CAA AGA CTG | 675 |
| 211 | Thr Thr Tyr Ile Ser Ile Gly Thr Ser Thr Leu Asn Gln Arg Leu | 225 |
| 676 | GTG CCT AAA ATC GCT ACA AGA TCA AAA ATC AAC GGT CAA AGA GGT | 720 |
| 226 | Val Pro Lys Ile Ala Thr Arg Ser Lys Ile Asn Gly Gln Arg Gly | 240 |
| 721 | AGA ATC GAC TTC TTC TGG ACA ATC CTG AAA CCT AAC GAC GCT ATC | 765 |
| 241 | Arg Ile Asp Phe Phe Trp Thr Ile Leu Lys Pro Asn Asp Ala Ile | 255 |
| 766 | CAC TTC GAA TCA AAC GGT AAC TTC ATC GCT CCT GAA TAC GCT TAC | 810 |
| 256 | His Phe Glu Ser Asn Gly Asn Phe Ile Ala Pro Glu Tyr Ala Tyr | 270 |
| 811 | AAA ATC GTG AAA AAA GGT GAC TCA ACA ATC ATG AAA TCA GAA GTG | 855 |
| 271 | Lys Ile Val Lys Lys Gly Asp Ser Thr Ile Met Lys Ser Glu Val | 285 |
| 856 | GAA TAC GGT AAC TGC AAC ACA AGA TGC CAA ACA CCT ATC GGT GCT | 900 |
| 286 | Glu Tyr Gly Asn Cys Asn Thr Arg Cys Gln Thr Pro Ile Gly Ala | 300 |
| 901 | ATC AAC TCA TCA ATG CCT TTC CAC AAC ATC CAC CCT CTG ACA ATC | 945 |
| 301 | Ile Asn Ser Ser Met Pro Phe His Asn Ile His Pro Leu Thr Ile | 315 |
| 946 | GGT GAA TGC CCT AAA TAC GTG AAA TCA AAC AAA CTG GTG CTG GCT | 990 |
| 316 | Gly Glu Cys Pro Lys Tyr Val Lys Ser Asn Lys Leu Val Leu Ala | 330 |

Fig. 3-3

| | | | | | | | | | | | | | | | |
|---|---|---|---|---|---|---|---|---|---|---|---|---|---|---|---|
| SEQ ID NO: 4 cont. | 991 | ACA | GGT | CTG | AGA | AAC | TCA | CCT | CAA | AGA | GAA | ACA | AGA | GGT | CTG | TTC | 1035 |
| SEQ ID NO: 3 cont. | 331 | Thr | Gly | Leu | Arg | Asn | Ser | Pro | Gln | Arg | Glu | Thr | Arg | Gly | Leu | Phe | 345 |

HA1 ← → HA2

| | | | | | | | | | | | | | |
|---|---|---|---|---|---|---|---|---|---|---|---|---|---|
| 1036 | GGT | GCT | ATC | GCT | GGT | TTC | ATC | GAA | GGT | GGT | TGG | CAA | GGT | ATG | GTG | 1080 |
| 346 | Gly | Ala | Ile | Ala | Gly | Phe | Ile | Glu | Gly | Gly | Trp | Gln | Gly | Met | Val | 360 |

| 1081 | GAC | GGT | TGG | TAC | GGT | TAC | CAC | CAC | TCA | AAC | GAA | CAA | GGT | TCA | GGT | 1125 |
| 361 | Asp | Gly | Trp | Tyr | Gly | Tyr | His | His | Ser | Asn | Glu | Gln | Gly | Ser | Gly | 375 |

| 1126 | TAC | GCT | GCT | GAC | AAA | GAA | TCA | ACA | CAA | AAA | GCT | ATC | GAC | GGT | GTG | 1170 |
| 376 | Tyr | Ala | Ala | Asp | Lys | Glu | Ser | Thr | Gln | Lys | Ala | Ile | Asp | Gly | Val | 390 |

| 1171 | ACA | AAC | AAA | GTG | AAC | TCA | ATC | ATC | GAC | AAA | ATG | AAC | ACA | CAA | TTC | 1215 |
| 391 | Thr | Asn | Lys | Val | Asn | Ser | Ile | Ile | Asp | Lys | Met | Asn | Thr | Gln | Phe | 405 |

| 1216 | GAA | GCT | GTG | GGT | AGA | GAA | TTC | AAC | AAC | CTG | GAA | AGA | AGA | ATC | GAA | 1260 |
| 406 | Glu | Ala | Val | Gly | Arg | Glu | Phe | Asn | Asn | Leu | Glu | Arg | Arg | Ile | Glu | 420 |

| 1261 | AAC | CTG | AAC | AAA | AAA | ATG | GAA | GAC | GGT | TTC | CTG | GAC | GTG | TGG | ACA | 1305 |
| 421 | Asn | Leu | Asn | Lys | Lys | Met | Glu | Asp | Gly | Phe | Leu | Asp | Val | Trp | Thr | 435 |

| 1306 | TAC | AAC | GCT | GAA | CTG | CTG | GTG | CTG | ATG | GAA | AAC | GAA | AGA | ACA | CTG | 1350 |
| 436 | Tyr | Asn | Ala | Glu | Leu | Leu | Val | Leu | Met | Glu | Asn | Glu | Arg | Thr | Leu | 450 |

| 1351 | GAC | TTC | CAC | GAC | TCA | AAC | GTG | AAA | AAC | CTG | TAC | GAC | AAA | GTG | AGA | 1395 |
| 451 | Asp | Phe | His | Asp | Ser | Asn | Val | Lys | Asn | Leu | Tyr | Asp | Lys | Val | Arg | 465 |

| 1396 | CTG | CAA | CTG | AAA | GAC | AAC | GCT | AAA | GAA | CTG | GGT | AAC | GGT | TGC | TTC | 1440 |
| 466 | Leu | Gln | Leu | Lys | Asp | Asn | Ala | Lys | Glu | Leu | Gly | Asn | Gly | Cys | Phe | 480 |

| 1441 | GAA | TTC | TAC | CAC | AAA | TGC | AAC | AAC | GAA | TGC | ATG | GAA | TCA | GTG | AGA | 1485 |
| 481 | Glu | Phe | Tyr | His | Lys | Cys | Asn | Asn | Glu | Cys | Met | Glu | Ser | Val | Arg | 495 |

Fig. 3-4

| | | | | | | | | | | | | | | | |
|---|---|---|---|---|---|---|---|---|---|---|---|---|---|---|---|
| SEQ ID NO: 4 cont. | 1486 | AAC | GGT | ACA | TAC | GAC | TAC | CCT | CAA | TAC | TCA | GAA | GAA | GCT | AGA | CTG | 1530 |
| SEQ ID NO: 3 cont. | 496 | Asn | Gly | Thr | Tyr | Asp | Tyr | Pro | Gln | Tyr | Ser | Glu | Glu | Ala | Arg | Leu | 510 |

| | 1531 | AAA | AGA | GAA | GAA | ATC | TCA | GGT | GTG | AAA | CTG | GAA | TCA | ATC | GGT | ATC | 1575 |
| | 511 | Lys | Arg | Glu | Glu | Ile | Ser | Gly | Val | Lys | Leu | Glu | Ser | Ile | Gly | Ile | 525 |

| | 1576 | TAC | CAA | ATC | CTG | TCA | ATC | TAC | TCA | ACA | GTG | GCT | TCA | TCA | CTG | GTG | 1620 |
| | 526 | Tyr | Gln | Ile | Leu | Ser | Ile | Tyr | Ser | Thr | Val | Ala | Ser | Ser | Leu | Val | 540 |

| | 1621 | CTG | GCT | ATC | ATG | ATG | GCT | GGT | CTG | TCA | CTG | TGG | ATG | TGC | TCA | AAC | 1665 |
| | 541 | Leu | Ala | Ile | Met | Met | Ala | Gly | Leu | Ser | Leu | Trp | Met | Cys | Ser | Asn | 555 |

| | 1666 | GGT | TCA | CTG | CAA | TGC | AGA | ATC | TGC | ATC | GAC | TAC | AAA | GAC | GAC | GAC | 1710 |
| | 556 | Gly | Ser | Leu | Gln | Cys | Arg | Ile | Cys | Ile | Asp | Tyr | Lys | Asp | Asp | Asp | 570 |

| | 1711 | GAC | AAA | TAA | 1719 |
| | 571 | Asp | Lys | End | 573 |

Asp Tyr Lys Asp Asp Asp — FLAG tag

Fig. 5-1

Query Range: 1 - 1691   SEQ ID NO: 4
Sbjct Range: 15 - 1714  SEQ ID NO: 1
1700 bp, INT.Score: 2684, OPT.Score: 4524
Identity: 1325 / 1700 (77%)
Similarity: 1325 / 1700 (77%)
Gaps: 9 / 1700 (0%)
Strand: Plus / Plus

```
SEQ ID NO: 4 cont. Query    1  ATGGAAAAAATCGTGCTGCTGTTCACAACAATCGGTCTGGTGAAATCAGACCACATCTGC   60
                                *****  *****  *****  ** **  ************  ** **  ***    ** ** ** ***
SEQ ID NO: 1 cont. Sbjct   15  ATGGAGAAAATAGTGCTTCTCTTTACAACAATCGGCCTTGTTAAAAGCGATCATATTTGC   74

Query   61  ATCGGTTACCACGCTAACAACTCAACAGAACAAGTGGACACAATCATGGAAAAAAACGTG  120
                                **  *****  **  ** **  *****   *****  **  **  ********  ********   *****  **
                   Sbjct   75  ATTGGTTATCATGCAAATAACTCGACAGAGCAGGTTGACACAATAATGGAAAAGAACGTT  134

Query  121  ACAGTGACACACGCTCAAGACATCCTGGAAAAAACACACAACGGTAAACTGTGCGACCTG  180
                                **  **  *****  **  ********  ********  ************  **  *****  **
                   Sbjct  135  ACTGTTACACATGCCCAAGACATACTGGAAAAGACACACAACGGGAAGCTCTGCGATCTA  194

Query  181  AACGGTGTGAAACCTCTGATCCTGAAAGACTGCTCAGTGGCTGGTTGGCTGCTGGGTAAC  240
                                **  **  *****  ********   *  *****  **       **  **  **  *****  **  **  ***
                   Sbjct  195  AATGGAGTGAAGCCTCTGATTTTAAAAGATTGTAGTGTAGCGGGATGGCTCCTCGGAAAC  254

Query  241  CCTCTGTGCGACGAATTCATCAACGTGCCTGAATGGTCATACATCGTGGAAAAAGCTAAC  300
                                **   ****  ************  *****  ********  **     **  ** ** **
                   Sbjct  255  CCATTGTGTGACGAATTCATCAATGTGCCAGAATGGTCTTACATAGTAGAGAAGGCCAAT  314

Query  301  CCTGCTAACGACCTGTGCTACCCTGGTAACTTCAACGACTACGAAGAACTGAAACACCTG  360
                                **  **  **  ******  **  *****  **  **  ********   **  ******  ************
                   Sbjct  315  CCAGCCAATGACCTCTGTTACCCAGGGAATTCAACGATTATGAAGAATTGAAACACCTA  374

Query  361  CTGTCAAGAATCAACCACTTCGAAAAAATCCAAATCATCCCTAAAGACTCATGGTCAGAC  420
                                **     **  **  *****  **  **  *****  **  ********  *******   ********
                   Sbjct  375  TTGAGCAGGATAAACCATTTTGAGAAAATACAGATCATCCCCAAAGACTCTTGGTCAGAT  434

Query  421  CACGAAGCTTCACTGGGTGTGTCAGCTGCTTGCTCATACCAAGGTAACTCATCATTCTTC  480
                                **  *****  ***  ****  ***     **  **  **  ********  **  ** **  **  *******
                   Sbjct  435  CATGAAGCCTCATTGGGGGTGAGCGCAGCATGTTCATACCAGGGAAATTCCTCCTTCTTC  494

Query  481  AGAAACGTGGTGTGGCTGATCAAAAAAGACAACGCTTACCCTACAATCAAAAAAGGTTAC  540
                                ******  ******  *****  ********  ****  ********  ** **  ******  ***
                   Sbjct  495  AGAAATGTGGTATGGCTTATCAAAAAGGACAATGCATACCCAACAATAAAGAAAGGCTAC  554

Query  541  AACAACACAAACCAAGAAGACCTGCTGGTGCTGTGGGGTATCCACCACCCTAACGACGAA  600
                                **  **  **  **********  **  *****   ****  ********  ************  **  **
                   Sbjct  555  AATAATACCAACCAAGAAGATCTCTTGGTACTGTGGGGATTCACCACCCTAATGATGAG  614

Query  601  GCTGAACAAACAAGACTGTACCAAAACCCTACAACATACATCTCAATCGGTACATCAACA  660
                                **  **  **  ******  **  **  ********  **  **  **  **  **  **  *********
                   Sbjct  615  GCAGAGCAGACAAGGCTCTATCAAAACCCAACCACCTATATTTCCATTGGACATCAACA  674

Query  661  CTGAACCAAAGACTGGTGCCTAAAATCGCTACAAGATCAAAAATCAACGGTCAAAGAGGT  720
                                **  *****  ***  ****  **  *****  **  **  *****  *****  *****  *****  **
                   Sbjct  675  CTAAACCAGAGATTGGTACCAAAAATAGCCACTAGATCCAAAATAAACGGGCAAAGGGGC  734

Query  721  AGAATCGACTTCTTCTGGACAATCCTGAAACCTAACGACGCTATCCACTTCGAATCAAAC  780
                                **  **  **  *************    *  *****  **  **  **  *************    **
                   Sbjct  735  AGGATAGATTTCTTCTGGACAATTTTAAAACCGAATGATGCAATCCACTTCGAGAGTAAT  794

Query  781  GGTAACTTCATCGCTCCTGAATACGCTTACAAAATCGTGAAAAAAGGTGACTCAACAATC  840
                                **  **  *****  *****  *****  **  ********  **  **  *****  *****  *****
                   Sbjct  795  GGAAATTTCATTGCTCCAGAATATGCATACAAAATTGTTAAGAAAGGAGACTCCACAATT  854
```

Fig. 5-2

| | | | |
|---|---|---|---|
| SEQ ID NO: 4 cont. Query | 841 | ATGAAATCAGAAGTGGAATACGGTAACTGCAACACAAGATGCCAAACACCTATCGGTGCT | 900 |
| SEQ ID NO: 1 cont. Sbjct | 855 | ATGAAAAGTGAAGTGGAATATGGTAACTGCAGCACCAGGTGTCAGACTCCGATAGGGGCG | 914 |
| Query | 901 | ATCAACTCATCAATGCCTTTCCACAACATCCACCCTCTGACAATCGGTGAATGCCCTAAA | 960 |
| Sbjct | 915 | ATAAACTCTAGTATGCCATTCCACAACATACCCCTCTCACCATCGGAGAATGTCCCAAA | 974 |
| Query | 961 | TACGTGAAATCAAACAAACTGGTGCTGGCTACAGGTCTGAGAAACTCACCTCAAAGAGAA | 1020 |
| Sbjct | 975 | TATGTGAAATCAAACAAATTAGTCCTTGCGACTGGGCTCAGAAATAGTCCTCAAAGAGAG | 1034 |
| Query | 1021 | ACAA----------GAGGTCTGTTCGGTGCTATCGCTGGTTTCATCGAAGGTGGTTGGCAA | 1071 |
| Sbjct | 1035 | AGAAGAAGAAAAGAGGACTGTTTGGAGCTATAGCAGGTTTTATAGAGGGAGGATGGCAG | 1094 |
| Query | 1072 | GGTATGGTGGACGGTTGGTACGGTTACCACCACTCAAACGAACAAGGTTCAGGTTACGCT | 1131 |
| Sbjct | 1095 | GGAATGGTAGATGGTTGGTATGGGTACCACCACAGCAATGAGCAGGGGAGTGGGTACGCT | 1154 |
| Query | 1132 | GCTGACAAAGAATCAACACAAAAAGCTATCGACGGTGTGACAAACAAAGTGAACTCAATC | 1191 |
| Sbjct | 1155 | GCAGACAAAGAATCTACTCAAAAGGCAATAGACGGAGTCACCAATAAGGTCAACTCGATC | 1214 |
| Query | 1192 | ATCGACAAAATGAACACACAATTCGAAGCTGTGGGTAGAGAATTCAACAACCTGGAAAGA | 1251 |
| Sbjct | 1215 | ATTGACAAAATGAACACTCAGTTTGAGGCCGTAGGAAGGGAATTTAACAACTTAGAGAGG | 1274 |
| Query | 1252 | AGAATCGAAAACCTGAACAAAAAAATGGAAGACGGTTTCCTGGACGTGTGGACATACAAC | 1311 |
| Sbjct | 1275 | AGAATAGAGAATTTAAACAAGAAGATGGAAGACGGATTCCTAGATGTTTGGACTTATAAT | 1334 |
| Query | 1312 | GCTGAACTGCTGGTGCTGATGGAAAACGAAAGAACACTGGACTTCCACGACTCAAACGTG | 1371 |
| Sbjct | 1335 | GCTGAACTTCTGGTTCTCATGGAAAATGAGAGAACTCTAGATTTCCATGACTCAAATGTC | 1394 |
| Query | 1372 | AAAAACCTGTACGACAAAGTGAGACTGCAACTGAAAGACAACGCTAAAGAACTGGGTAAC | 1431 |
| Sbjct | 1395 | AAGAACCTTTACGATAAGGTCAGACTACAGCTTAAGGATAATGCAAAAGAGTTGGGTAAC | 1454 |
| Query | 1432 | GGTTGCTTCGAATTCTACCACAAATGCAACAACGAATGCATGGAATCAGTGAGAAACGGT | 1491 |
| Sbjct | 1455 | GGTTGTTTCGAGTTCTATCACAAATGTAATAATGAATGTATGGAAAGTGTAAGAAACGGA | 1514 |
| Query | 1492 | ACATACGACTACCCTCAATACTCAGAAGAAGCTAGACTGAAAAGAGAAGAAATCTCAGGT | 1551 |
| Sbjct | 1515 | ACGTATGACTACCCGCAGTATTCAGAAGAAGCAAGACTAAAAAGAGAGGAAATAAGTGGA | 1574 |
| Query | 1552 | GTGAAACTGGAATCAATCGGTATCTACCAAATCCTGTCAATCTACTCAACAGTGGCTTCA | 1611 |
| Sbjct | 1575 | GTAAAATTGGAATCAATAGGAATCTACCAAATACTGTCAATTTATTCAACAGTGGCGAGT | 1634 |
| Query | 1612 | TCACTGGTGCTGGCTATCATGATGGCTGGTCTGTCACTGTGGATGTGCTCAAACGGTTCA | 1671 |
| Sbjct | 1635 | TCCCTAGTGCTGGCAATCATGATGGCTGGTCTGTCTTTATGGATGTGTTCCAACGGATCG | 1694 |
| Query | 1672 | CTGCAATGCAGAATCTGCAT | 1691 |
| Sbjct | 1695 | TTACAGTGCAGAATTTGCAT | 1714 |

HI antibody reaction with epizootic viruses

| Test antigens | HI titer |
|---|---|
| | Antibody to silkworm derived HA |
| A/chicken/Legok/2004 (H5N1) | 256 |
| A/chicken/West Java/2009 (H5N1) | 256 |
| Silkworm-derived HA | 2,048 |

Fig. 8 a) Fractionation of HA molecules

Fig. 10-1

| SEQ ID NO: 12 | 1 | ATG GAA AAA ACA GCT CTG CTG CTG GCT ATC GTG TCA CTG GTG AAA | 45 |
|---|---|---|---|
| SEQ ID NO: 11 | 1 | Met Glu Lys Thr Ala Leu Leu Leu Ala Ile Val Ser Leu Val Lys | 15 |
| | 46 | TCA GAC CAA ATC TGC ATC GGT TAC CAC GCT AAC AAC TCA ACA GAA | 90 |
| | 16 | Ser Asp Gln Ile Cys Ile Gly Tyr His Ala Asn Asn Ser Thr Glu | 30 |
| | 91 | CAA GTG GAC ACA ATC ATG GAA AAA AAC GTG ACA GTG ACA CAC GCT | 135 |
| | 31 | Gln Val Asp Thr Ile Met Glu Lys Asn Val Thr Val Thr His Ala | 45 |
| | 136 | CAA GAC ATC CTG GAA AAA ACA CAC AAC GGT AAA CTG TGC GAC CTG | 180 |
| | 46 | Gln Asp Ile Leu Glu Lys Thr His Asn Gly Lys Leu Cys Asp Leu | 60 |
| | 181 | GAC GGT GTG AAA CCT CTG ATC CTG AGA GAC TGC TCA GTG GCT GGT | 225 |
| | 61 | Asp Gly Val Lys Pro Leu Ile Leu Arg Asp Cys Ser Val Ala Gly | 75 |
| | 226 | TGG CTG CTG GGT AAC CCT ATG TGC GAC GAA TTC ATC AAA GTG AAA | 270 |
| | 76 | Trp Leu Leu Gly Asn Pro Met Cys Asp Glu Phe Ile Lys Val Lys | 90 |
| | 271 | GAA TGG TCA TAC ATC GTG GAA AAA GCT TCA CCT ACA AAC GAC CTG | 315 |
| | 91 | Glu Trp Ser Tyr Ile Val Glu Lys Ala Ser Pro Thr Asn Asp Leu | 105 |
| | 316 | TGC TAC CCT GGT TCA TTC AAC GAC TAC GAA GAA CTG AAA CAC CTG | 360 |
| | 106 | Cys Tyr Pro Gly Ser Phe Asn Asp Tyr Glu Glu Leu Lys His Leu | 120 |
| | 361 | CTG TCA AGA ATC AAA CAC TTC GAA AAA ATC AGA ATC ATC CCT AGA | 405 |
| | 121 | Leu Ser Arg Ile Lys His Phe Glu Lys Ile Arg Ile Ile Pro Arg | 135 |
| | 406 | TCA GAC TGG TCA GAC CAC GAA ACA TCA GGT GTG TCA TCA GCT TGC | 450 |
| | 136 | Ser Asp Trp Ser Asp His Glu Thr Ser Gly Val Ser Ser Ala Cys | 150 |
| | 451 | CCT TAC CTG GGT TCA CCT TCA TTC TTC AGA AAC GTG GTG TGG CTG | 495 |
| | 151 | Pro Tyr Leu Gly Ser Pro Ser Phe Phe Arg Asn Val Val Trp Leu | 165 |

Fig. 10-2

| | | | | | | | | | | | | | | | | |
|---|---|---|---|---|---|---|---|---|---|---|---|---|---|---|---|---|
| SEQ ID NO: 12 cont. | 496 | ACA | CAA | AAA | AAC | TCA | ACA | TAC | CCT | ATC | ATC | AAA | AAA | TCA | TAC | AAA | 540 |
| SEQ ID NO: 11 cont. | 166 | Thr | Gln | Lys | Asn | Ser | Thr | Tyr | Pro | Ile | Ile | Lys | Lys | Ser | Tyr | Lys | 180 |
| | 541 | AAC | ACA | AAC | CAA | GAA | GAC | CTG | CTG | ATC | CTG | TGG | GGT | ATC | CAC | CAC | 585 |
| | 181 | Asn | Thr | Asn | Gln | Glu | Asp | Leu | Leu | Ile | Leu | Trp | Gly | Ile | His | His | 195 |
| | 586 | TCA | AAC | AAC | GTG | GAA | GAA | CAA | ACA | AGA | CTG | TAC | CAA | AAC | CTG | ACA | 630 |
| | 196 | Ser | Asn | Asn | Val | Glu | Glu | Gln | Thr | Arg | Leu | Tyr | Gln | Asn | Leu | Thr | 210 |
| | 631 | ACA | TAC | ATC | TCA | ATC | GGT | ACA | TCA | ACA | CTG | AAC | CAA | AGA | TCA | GTG | 675 |
| | 211 | Thr | Tyr | Ile | Ser | Ile | Gly | Thr | Ser | Thr | Leu | Asn | Gln | Arg | Ser | Val | 225 |
| | 676 | CCT | AAA | ATC | GCT | ACA | AGA | ACA | AAA | GTG | CAC | GGT | CAA | TCA | GGT | AGA | 720 |
| | 226 | Pro | Lys | Ile | Ala | Thr | Arg | Thr | Lys | Val | His | Gly | Gln | Ser | Gly | Arg | 240 |
| | 721 | ATG | GAC | TTC | TTC | TGG | ACA | ATC | CTG | AAC | TCA | AAC | GAC | ACA | ATC | TAC | 765 |
| | 241 | Met | Asp | Phe | Phe | Trp | Thr | Ile | Leu | Asn | Ser | Asn | Asp | Thr | Ile | Tyr | 255 |
| | 766 | TTC | GAA | TCA | AAC | GGT | AAC | TTC | ATC | GCT | CCT | GAA | TAC | GCT | TAC | AAA | 810 |
| | 256 | Phe | Glu | Ser | Asn | Gly | Asn | Phe | Ile | Ala | Pro | Glu | Tyr | Ala | Tyr | Lys | 270 |
| | 811 | ATC | GTG | AAA | AAA | GGT | GAC | TCA | GCT | ATC | ATG | AAA | TCA | GAA | CTG | GAA | 855 |
| | 271 | Ile | Val | Lys | Lys | Gly | Asp | Ser | Ala | Ile | Met | Lys | Ser | Glu | Leu | Glu | 285 |
| | 856 | TAC | GGT | GAC | TGC | AAC | ACA | AAA | TGC | CAA | ACA | CCT | ATG | GGT | GCT | ATC | 900 |
| | 286 | Tyr | Gly | Asp | Cys | Asn | Thr | Lys | Cys | Gln | Thr | Pro | Met | Gly | Ala | Ile | 300 |
| | 901 | AAC | TCA | TCA | ATG | CCT | TTC | CAC | AAC | ATC | CAC | CCT | CTG | ACA | ATC | GGT | 945 |
| | 301 | Asn | Ser | Ser | Met | Pro | Phe | His | Asn | Ile | His | Pro | Leu | Thr | Ile | Gly | 315 |
| | 946 | GAA | TGC | CCT | AAA | TAC | GTG | AAA | TCA | AAC | AGA | CTG | GTG | CTG | GCT | ACA | 990 |
| | 316 | Glu | Cys | Pro | Lys | Tyr | Val | Lys | Ser | Asn | Arg | Leu | Val | Leu | Ala | Thr | 330 |

Fig. 10-3

SEQ ID NO: 12 cont.
HA1 ← → HA2
SEQ ID NO: 11 cont.

| | | |
|---|---|---|
| 991 | GGT CTG AGA AAC TCA CCT CAA AGA GAA TCA AGA GGT CTG TTC GGT | 1035 |
| 331 | Gly Leu Arg Asn Ser Pro Gln Arg Glu Ser Arg Gly Leu Phe Gly | 345 |
| 1036 | GCT ATC GCT GGT TTC ATC GAA GGT GGT TGG CAA GGT ATG GTG GAC | 1080 |
| 346 | Ala Ile Ala Gly Phe Ile Glu Gly Gly Trp Gln Gly Met Val Asp | 360 |
| 1081 | GGT TGG TAC GGT TAC CAC CAC TCA AAC GAA CAA GGT TCA GGT TAC | 1125 |
| 361 | Gly Trp Tyr Gly Tyr His His Ser Asn Glu Gln Gly Ser Gly Tyr | 375 |
| 1126 | GCT GCT GAC AAA GAA TCA ACA CAA AAA GCT ATC GAC GGT ATC ACA | 1170 |
| 376 | Ala Ala Asp Lys Glu Ser Thr Gln Lys Ala Ile Asp Gly Ile Thr | 390 |
| 1171 | AAC AAA GTG AAC TCA ATC ATC GAC AAA ATG AAC ACA CAA TTC GAA | 1215 |
| 391 | Asn Lys Val Asn Ser Ile Ile Asp Lys Met Asn Thr Gln Phe Glu | 405 |
| 1216 | GCT GTG GGT AGA GAA TTC AAC AAC CTG GAA AGA AGA ATC GAA AAC | 1260 |
| 406 | Ala Val Gly Arg Glu Phe Asn Asn Leu Glu Arg Arg Ile Glu Asn | 420 |
| 1261 | CTG AAC AAA AAA ATG GAA GAC GGT TTC CTG GAC GTG TGG ACA TAC | 1305 |
| 421 | Leu Asn Lys Lys Met Glu Asp Gly Phe Leu Asp Val Trp Thr Tyr | 435 |
| 1306 | AAC GCT GAA CTG CTG GTG CTG ATG GAA AAC GAA AGA ACA CTG GAC | 1350 |
| 436 | Asn Ala Glu Leu Leu Val Leu Met Glu Asn Glu Arg Thr Leu Asp | 450 |
| 1351 | TTC CAC GAC TCA AAC GTG AAA AAC CTG TAC GAC AAA GTG AGA CTG | 1395 |
| 451 | Phe His Asp Ser Asn Val Lys Asn Leu Tyr Asp Lys Val Arg Leu | 465 |
| 1396 | CAA CTG AGA GAC AAC GCT AAA GAA CTG GGT AAC GGT TGC TTC GAA | 1440 |
| 466 | Gln Leu Arg Asp Asn Ala Lys Glu Leu Gly Asn Gly Cys Phe Glu | 480 |
| 1441 | TTC TAC CAC AAA TGC GAC AAC GAA TGC ATG GAA TCA ATC AGA AAC | 1485 |
| 481 | Phe Tyr His Lys Cys Asp Asn Glu Cys Met Glu Ser Ile Arg Asn | 495 |

Fig. 10-4

```
SEQ ID NO: 12 cont. 1486  GGT ACA TAC AAC TAC CCT CAA TAC TCA GAA GAA GCT AGA CTG AAA  1530
SEQ ID NO: 11 cont. 496   Gly Thr Tyr Asn Tyr Pro Gln Tyr Ser Glu Glu Ala Arg Leu Lys  510

1531  AGA GAA GAA ATC TCA GGT GTG AAA CTG GAA TCA ATC GGT ACA TAC  1575
                    511   Arg Glu Glu Ile Ser Gly Val Lys Leu Glu Ser Ile Gly Thr Tyr  525

1576  CAA ATC CTG TCA ATC TAC TCA ACA GTG GCT TCA TCA CTG GCT CTG  1620
                    526   Gln Ile Leu Ser Ile Tyr Ser Thr Val Ala Ser Ser Leu Ala Leu  540

1621  GCT ATC ATG ATG GCT GGT CTG TCA CTG TGG ATG TGC TCA AAC GGT  1665
                    541   Ala Ile Met Met Ala Gly Leu Ser Leu Trp Met Cys Ser Asn Gly  555

1666  TCA CTG CAA TGC AGA ATC TGC ATC GAC TAC AAA GAC GAC GAC GAC  1710
                    556   Ser Leu Gln Cys Arg Ile Cys Ile |Asp Tyr Lys Asp Asp Asp Asp| 570

1711  AAA TAA  1716
                    571   |Lys|End  572                          ——— FLAG tag
```

Fig. 11

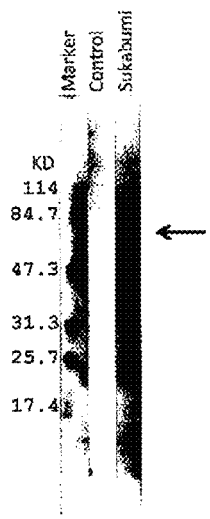

Fig. 12-1

| SEQ ID NO: 15 | 1 | ATG TCA ACA AAC CCT AAA CCT CAA AGA AAA ACA AAA AGA AAC ACA | 45 |
|---|---|---|---|
| SEQ ID NO: 14 | 1 | Met Ser Thr Asn Pro Lys Pro Gln Arg Lys Thr Lys Arg Asn Thr | 15 |
| | | CORE Protein | |
| | 46 | AAC AGA AGA CCT CAA GAC GTG AAA TTC CCT GGT GGT GGT CAA ATC | 90 |
| | 16 | Asn Arg Arg Pro Gln Asp Val Lys Phe Pro Gly Gly Gly Gln Ile | 30 |
| | 91 | GTG GGT GGT GTG TAC CTG CTG CCT AGA AGA GGT CCT AGA CTG GGT | 135 |
| | 31 | Val Gly Gly Val Tyr Leu Leu Pro Arg Arg Gly Pro Arg Leu Gly | 45 |
| | 136 | GTG AGA GCT ACA AGA AAA ACA TCA GAA AGA TCA CAA CCT AGA GGT | 180 |
| | 46 | Val Arg Ala Thr Arg Lys Thr Ser Glu Arg Ser Gln Pro Arg Gly | 60 |
| | 181 | AGA AGA CAA CCT ATC CCT AAA GCT AGA CAA CCT GAA GGT AGA GCT | 225 |
| | 61 | Arg Arg Gln Pro Ile Pro Lys Ala Arg Gln Pro Glu Gly Arg Ala | 75 |
| | 226 | TGG GCT CAA CCT GGT TAC CCT TGG CCT CTG TAC GGT AAC GAA GGT | 270 |
| | 76 | Trp Ala Gln Pro Gly Tyr Pro Trp Pro Leu Tyr Gly Asn Glu Gly | 90 |
| | 271 | ATG GGT TGG GCT GGT TGG CTG CTG TCA CCT AGA GGT TCA AGA CCT | 315 |
| | 91 | Met Gly Trp Ala Gly Trp Leu Leu Ser Pro Arg Gly Ser Arg Pro | 105 |
| | 316 | TCA TGG GGT CCT ACA GAC CCT AGA AGA AGA TCA AGA AAC CTG GGT | 360 |
| | 106 | Ser Trp Gly Pro Thr Asp Pro Arg Arg Arg Ser Arg Asn Leu Gly | 120 |
| | 361 | AAA GTG ATC GAC ACA CTG ACA TGC GGT TTC GCT GAC CTG ATG GGT | 405 |
| | 121 | Lys Val Ile Asp Thr Leu Thr Cys Gly Phe Ala Asp Leu Met Gly | 135 |
| | 406 | TAC ATC CCT CTG GTG GGT GCT CCT CTG GGT GGT GCT GCT AGA GCT | 450 |
| | 136 | Tyr Ile Pro Leu Val Gly Ala Pro Leu Gly Gly Ala Ala Arg Ala | 150 |
| | 451 | CTG GCT CAC GGT GTG AGA GTG CTG GAA GAC GGT GTG AAC TAC GCT | 495 |
| | 151 | Leu Ala His Gly Val Arg Val Leu Glu Asp Gly Val Asn Tyr Ala | 165 |

Fig. 12-2

| | | |
|---|---|---|
| SEQ ID NO: 15 cont. 496 | ACA GGT AAC CTG CCT GGT TGC TCA TTC TCA ATC TTC CTG CTG GCT | 540 |
| SEQ ID NO: 14 cont. 166 | Thr Gly Asn Leu Pro Gly Cys Ser Phe Ser Ile Phe Leu Leu Ala | 180 |

| | | |
|---|---|---|
| 541 | CTG CTG TCA TGC CTG ACA ATC CCT GCT TCA GCT TAC GAA GTG AGA | 585 |
| 181 | Leu Leu Ser Cys Leu Thr Ile Pro Ala Ser Ala Tyr Glu Val Arg | 195 |

Core ←——→ E1

| | | |
|---|---|---|
| 586 | AAC GTG TCA GGT GCT TAC CAC GTG ACA AAC GAC TGC GCT AAC ACA | 630 |
| 196 | Asn Val Ser Gly Ala Tyr His Val Thr Asn Asp Cys Ala Asn Thr | 210 |

| | | |
|---|---|---|
| 631 | TCA ATC GTG TAC GAA GCT GCT GAC ATG ATC ATG CAC ACA CCT GGT | 675 |
| 211 | Ser Ile Val Tyr Glu Ala Ala Asp Met Ile Met His Thr Pro Gly | 225 |

| | | |
|---|---|---|
| 676 | TGC GTG CCT TGC GTG AGA GAA AAC AAC TCA TCA AGA TGC TGG GTG | 720 |
| 226 | Cys Val Pro Cys Val Arg Glu Asn Asn Ser Ser Arg Cys Trp Val | 240 |

| | | |
|---|---|---|
| 721 | GCT CTG ACA CCT ACA CTG GCT GCT AGA AAC GCT TCA ATC CCT ACA | 765 |
| 241 | Ala Leu Thr Pro Thr Leu Ala Ala Arg Asn Ala Ser Ile Pro Thr | 255 |

| | | |
|---|---|---|
| 766 | ACA ACA ATC AGA AGA CAC GTG GAC CTG CTG GTG GGT GCT GCT GCT | 810 |
| 256 | Thr Thr Ile Arg Arg His Val Asp Leu Leu Val Gly Ala Ala Ala | 270 |

| | | |
|---|---|---|
| 811 | TTC TGC TCA GCT ATG TAC GTG GGT GAC CTG TGC GGT TCA GTG TTC | 855 |
| 271 | Phe Cys Ser Ala Met Tyr Val Gly Asp Leu Cys Gly Ser Val Phe | 285 |

| | | |
|---|---|---|
| 856 | CTG GTG TCA CAA CTG TTC GTG TTC TCA CCT AGA AGA CAC GAA ACA | 900 |
| 286 | Leu Val Ser Gln Leu Phe Val Phe Ser Pro Arg Arg His Glu Thr | 300 |

| | | |
|---|---|---|
| 901 | GTG CAA GAC TGC AAC TGC TCA ATC TAC CCT GGT CAC GTG TCA GGT | 945 |
| 301 | Val Gln Asp Cys Asn Cys Ser Ile Tyr Pro Gly His Val Ser Gly | 315 |

| | | |
|---|---|---|
| 945 | CAC AGA ATG GCT TGG GAC ATG ATG ATG AAC TGG TCA CCT ACA GCT | 990 |

Fig. 12-3

| | | | |
|---|---|---|---|
| SEQ ID NO: 14 cont. | 316 | His Arg Met Ala Trp Asp Met Met Met Asn Trp Ser Pro Thr Ala | 330 |
| SEQ ID NO: 15 cont. | 991 | GCT CTG ATG GTG TCA CAA CTG CTG AGA ATC CCT CAA GCT GTG GTG | 1035 |
| SEQ ID NO: 14 cont. | 331 | Ala Leu Met Val Ser Gln Leu Leu Arg Ile Pro Gln Ala Val Val | 345 |
| | 1036 | GAC ATG GTG GCT GGT GCT CAC TGG GGT ATC CTG GCT GGT CTG GCT | 1080 |
| | 346 | Asp Met Val Ala Gly Ala His Trp Gly Ile Leu Ala Gly Leu Ala | 360 |
| | 1081 | TAC TAC TCA ATG GTG GGT AAC TGG GCT AAA GTG CTG ATC GTG ATG | 1125 |
| | 361 | Tyr Tyr Ser Met Val Gly Asn Trp Ala Lys Val Leu Ile Val Met | 375 |
| | 1126 | CTG CTG TTC GCT GGT GTG GAC GGT ACA ACA CAC GTG TCA GGT GGT | 1170 |
| | 376 | Leu Leu Phe Ala Gly Val Asp Gly Thr Thr His Val Ser Gly Gly | 390 |

E1 ←——┘└——→ E2

| | | |
|---|---|---|
| 1171 | GCT GCT GGT AGA AAC ACA TAC GGT CTG ACA TCA CTG TTC ACA CCT | 1215 |
| 391 | Ala Ala Gly Arg Asn Thr Tyr Gly Leu Thr Ser Leu Phe Thr Pro | 405 |
| 1216 | GGT GCT TCA CAA AAC ATC CAA CTG ATC AAC ACA AAC GGT TCA TGG | 1260 |
| 406 | Gly Ala Ser Gln Asn Ile Gln Leu Ile Asn Thr Asn Gly Ser Trp | 420 |
| 1261 | CAC ATC AAC AGA ACA GCT CTG AAC TGC AAC GAC TCA CTG AAC ACA | 1305 |
| 421 | His Ile Asn Arg Thr Ala Leu Asn Cys Asn Asp Ser Leu Asn Thr | 435 |
| 1306 | GGT TTC CTG GCT GCT CTG TTC TAC ACA CAC AGA TTC AAC GCT TCA | 1350 |
| 436 | Gly Phe Leu Ala Ala Leu Phe Tyr Thr His Arg Phe Asn Ala Ser | 450 |
| 1351 | GGT TGC CCT GAA AGA CTG GCT CAC TGC AGA CCT ATC GAC ACA TTC | 1395 |
| 451 | Gly Cys Pro Glu Arg Leu Ala His Cys Arg Pro Ile Asp Thr Phe | 465 |
| 1396 | GCT CAA GGT TGG GGT CCT ATC ACA TAC GCT GGT CAA AGA GGT CTG | 1440 |
| 466 | Ala Gln Gly Trp Gly Pro Ile Thr Tyr Ala Gly Gln Arg Gly Leu | 480 |

Fig. 12-4

| | | | |
|---|---|---|---|
| SEQ ID NO: 15 cont. | 1441 | GAC CAA AGA CCT TAC TGC TGG CAC TAC GCT CCT AAA CCT TGC GGT | 1485 |
| SEQ ID NO: 14 cont. | 481 | Asp Gln Arg Pro Tyr Cys Trp His Tyr Ala Pro Lys Pro Cys Gly | 495 |
| | 1486 | ATC GTG CCT GCT TCA CAA GTG TGC GGT CCT GTG TAC TGC TTC ACA | 1530 |
| | 496 | Ile Val Pro Ala Ser Gln Val Cys Gly Pro Val Tyr Cys Phe Thr | 510 |
| | 1531 | CCT TCA CCT GTG GTG GTG GGT ACA ACA GAC AGA TTC GGT GTG CCT | 1575 |
| | 511 | Pro Ser Pro Val Val Val Gly Thr Thr Asp Arg Phe Gly Val Pro | 525 |
| | 1576 | ACA TAC ACA TGG GGT GAA AAC GAA ACA GAC GTG CTG CTG CTG AAC | 1620 |
| | 526 | Thr Tyr Thr Trp Gly Glu Asn Glu Thr Asp Val Leu Leu Leu Asn | 540 |
| | 1621 | AAC ACA AGA CCT CCT CAA GGT AAC TGG TTC GGT TGC ACA TGG ATG | 1665 |
| | 541 | Asn Thr Arg Pro Pro Gln Gly Asn Trp Phe Gly Cys Thr Trp Met | 555 |
| | 1666 | AAC TCA ACA GGT TAC ACA AAA ACA TGC GGT GGT CCT CCT TGC GAC | 1710 |
| | 556 | Asn Ser Thr Gly Tyr Thr Lys Thr Cys Gly Gly Pro Pro Cys Asp | 570 |
| | 1711 | ATC GGT GGT GCT GGT AAC AAC ACA CTG ATC TGC CCT ACA GAC TGC | 1755 |
| | 571 | Ile Gly Gly Ala Gly Asn Asn Thr Leu Ile Cys Pro Thr Asp Cys | 585 |
| | 1756 | TTC AGA AAA CAC CCT GAA GCT ACA TAC ACA AAA TGC GGT TCA GGT | 1800 |
| | 586 | Phe Arg Lys His Pro Glu Ala Thr Tyr Thr Lys Cys Gly Ser Gly | 600 |
| | 1801 | CCT TGG CTG ACA CCT AGA TGC ATG GTG GAC TAC CCT TAC AGA CTG | 1845 |
| | 601 | Pro Trp Leu Thr Pro Arg Cys Met Val Asp Tyr Pro Tyr Arg Leu | 615 |
| | 1846 | TGG CAC TAC CCT TGC ACA GTG AAC TTC ACA ATC TTC AAA GTG AGA | 1890 |
| | 616 | Trp His Tyr Pro Cys Thr Val Asn Phe Thr Ile Phe Lys Val Arg | 630 |
| | 1891 | ATG TAC GTG GGT GGT GTG GAA CAC AGA CTG AAC GCT GCT TGC AAC | 1935 |
| | 631 | Met Tyr Val Gly Gly Val Glu His Arg Leu Asn Ala Ala Cys Asn | 645 |

Fig. 12-5

| | | | |
|---|---|---|---|
| SEQ ID NO: 15 cont. | 1936 | TGG ACA AGA GGT GAA AGA TGC GAC CTG GAA GAC AGA GAC AGA TCA | 1980 |
| SEQ ID NO: 14 cont. | 646 | Trp Thr Arg Gly Glu Arg Cys Asp Leu Glu Asp Arg Asp Arg Ser | 660 |

```
1981   GAA CTG TCA CCT CTG CTG CTG TCA ACA ACA GAA TGG CAA ATC CTG   2025
661    Glu Leu Ser Pro Leu Leu Leu Ser Thr Thr Glu Trp Gln Ile Leu   675

2026   CCT TGC TCA TTC ACA ACA CTG CCT GCT CTG TCA ACA GGT CTG ATC   2070
676    Pro Cys Ser Phe Thr Thr Leu Pro Ala Leu Ser Thr Gly Leu Ile   690

2071   CAC CTG CAC CAA AAC ATC GTG GAC GTG CAA TAC CTG TAC GGT ATC   2115
691    His Leu His Gln Asn Ile Val Asp Val Gln Tyr Leu Tyr Gly Ile   705

2116   GGT TCA GTG GTG GTG TCA TTC GCT ATC AAA TGG GAA TAC GTG CTG   2160
706    Gly Ser Val Val Val Ser Phe Ala Ile Lys Trp Glu Tyr Val Leu   720

2161   CTG CTG TTC CTG CTG CTG GCT GAC GCT AGA GTG TGC GCT TGC CTG   2205
721    Leu Leu Phe Leu Leu Leu Ala Asp Ala Arg Val Cys Ala Cys Leu   735

2206   TGG ATG ATG CTG CTG ATC GCT CAA GCT GAA AGA GAC TAC AAA GAC   2250
736    Trp Met Met Leu Leu Ile Ala Gln Ala Glu |Arg| Asp Tyr Lys Asp   750
                     Original amino acid sequence |Ala|

2251   GAC GAC GAC AAA TAA   2265
751    |Asp Asp Asp Lys| End   755          FLAG tag
```

Fig. 14-1

| | | | |
|---|---|---|---|
| SEQ ID NO: 18 | 1 | ATG AAC ACA CAA ATC CTG GTG TTC GCT CTG ATC GCT ATC ATC CCT | 45 |
| SEQ ID NO: 17 | 1 | Met Asn Thr Gln Ile Leu Val Phe Ala Leu Ile Ala Ile Ile Pro | 15 |
| | 46 | ACA AAC GCT GAC AAA ATC TGC CTG GGT CAC CAC GCT GTG TCA AAC | 90 |
| | 16 | Thr Asn Ala Asp Lys Ile Cys Leu Gly His His Ala Val Ser Asn | 30 |
| | 91 | GGT ACA AAA GTG AAC ACA CTG ACA GAA AGA GGT GTG GAA GTG GTG | 135 |
| | 31 | Gly Thr Lys Val Asn Thr Leu Thr Glu Arg Gly Val Glu Val Val | 45 |
| | 136 | AAC GCT ACA GAA ACA GTG GAA AGA ACA AAC ATC CCT AGA ATC TGC | 180 |
| | 46 | Asn Ala Thr Glu Thr Val Glu Arg Thr Asn Ile Pro Arg Ile Cys | 60 |
| | 181 | TCA AAA GGT AAA AGA ACA GTG GAC CTG GGT CAA TGC GGT CTG CTG | 225 |
| | 61 | Ser Lys Gly Lys Arg Thr Val Asp Leu Gly Gln Cys Gly Leu Leu | 75 |
| | 226 | GGT ACA ATC ACA GGT CCT CCT CAA TGC GAC CAA TTC CTG GAA TTC | 270 |
| | 76 | Gly Thr Ile Thr Gly Pro Pro Gln Cys Asp Gln Phe Leu Glu Phe | 90 |
| | 271 | TCA GCT GAC CTG ATC ATC GAA AGA AGA GAA GGT TCA GAC GTG TGC | 315 |
| | 91 | Ser Ala Asp Leu Ile Ile Glu Arg Arg Glu Gly Ser Asp Val Cys | 105 |
| | 316 | TAC CCT GGT AAA TTC GTG AAC GAA GAA GCT CTG AGA CAA ATC CTG | 360 |
| | 106 | Tyr Pro Gly Lys Phe Val Asn Glu Glu Ala Leu Arg Gln Ile Leu | 120 |
| | 361 | AGA GAA TCA GGT GGT ATC GAC AAA GAA GCT ATG GGT TTC ACA TAC | 405 |
| | 121 | Arg Glu Ser Gly Gly Ile Asp Lys Glu Ala Met Gly Phe Thr Tyr | 135 |
| | 406 | TCA GGT ATC AGA ACA AAC GGT GGT ACA TCA GCT TGC AGA AGA TCA | 450 |
| | 136 | Ser Gly Ile Arg Thr Asn Gly Ala Thr Ser Ala Cys Arg Arg Ser | 150 |
| | 451 | GGT TCA TCA TTC TAC GCT GAA ATG AAA TGG CTG CTG TCA AAC ACA | 495 |
| | 151 | Gly Ser Ser Phe Tyr Ala Glu Met Lys Trp Leu Leu Ser Asn Thr | 165 |

Fig. 14-2

| | | |
|---|---|---|
| SEQ ID NO: 18 cont. 496 | GAC AAC GCT GCT TTC CCT CAA ATG ACA AAA TCA TAC AAA AAC ACA | 540 |
| SEQ ID NO: 17 cont. 166 | Asp Asn Ala Ala Phe Pro Gln Met Thr Lys Ser Tyr Lys Asn Thr | 180 |

```
541   AGA AAA TCA CCT GCT CTG ATC GTG TGG GGT ATC CAC CAC TCA GTG   585
181   Arg Lys Ser Pro Ala Leu Ile Val Trp Gly Ile His His Ser Val   195

586   TCA ACA GCT GAC CAA ACA AAA CTG TAC GGT TCA GGT AAC AAA CTG   630
196   Ser Thr Ala [Asp] Gln Thr Lys Leu Tyr Gly Ser Gly Asn Lys Leu   210
               [Glu] Original amino acid sequence 631   GTG ACA GTG GGT TCA TCA AAC TAC CAA CAA TCA TTC GTG CCT TCA   675
211   Val Thr Val Gly Ser Ser Asn Tyr Gln Gln Ser Phe Val Pro Ser   225

676   CCT GGT GCT AGA CCT CAA GTG AAC GAC CTG TCA GGT AGA ATC GAC   720
226   Pro Gly Ala Arg Pro Gln Val Asn [Asp] Leu Ser Gly Arg Ile Asp   240
              Original amino acid sequence [Gly]

721   TTC CAC TGG CTG ATG CTG AAC CCT AAC GAC ACA GTG ACA TTC TCA   765
241   Phe His Trp Leu Met Leu Asn Pro Asn Asp Thr Val Thr Phe Ser   255

766   TTC AAC GGT GCT TTC ATC GCT CCT GAC AGA GCT TCA TTC CTG AGA   810
256   Phe Asn Gly Ala Phe Ile Ala Pro Asp Arg Ala Ser Phe Leu Arg   270

811   GGT AAA TCA ATG GGT ATC CAA TCA GGT GTG CAA GTG GAC GCT AAC   855
271   Gly Lys Ser Met Gly Ile Gln Ser Gly Val Gln Val Asp Ala Asn   285

856   TGC GAA GGT GAC TGC TAC CAC TCA GGT GGT ACA ATC ATC TCA AAC   900
286   Cys Glu Gly Asp Cys Tyr His Ser Gly Gly Thr Ile Ile Ser Asn   300

901   CTG CCT TTC CAA AAC ATC GAC TCA AGA GCT GTG GGT AAA TGC CCT   945
301   Leu Pro Phe Gln Asn Ile Asp Ser Arg Ala Val Gly Lys Cys Pro   315

946   AGA TAC GTG AAA CAA AGA TCA CTG CTG CTG GCT ACA GGT ATG AAA   990
316   Arg Tyr Val Lys Gln Arg Ser Leu Leu Leu Ala Thr Gly Met Lys   330
```

Fig. 14-3

SEQ ID NO: 18 cont.  991   AAC GTG CCT GAA ATC CCT AAA GGT AGA GGT CTG TTC GGT GCT ATC   1035  →HA2
HA1←─────────────────────────────────────────────────────────────────
SEQ ID NO: 17 cont.  331   Asn Val Pro Glu Ile Pro Lys Gly Arg║Gly Leu Phe Gly Ala Ile    345

1036   GCT GGT TTC ATC GAA AAC GGT TGG GAA GGT CTG ATC GAC GGT TGG   1080
346    Ala Gly Phe Ile Glu Asn Gly Trp Glu Gly Leu Ile Asp Gly Trp    360

1081   TAC GGT TTC AGA CAC CAA AAC GCT CAA GGT GAA GGT ACA GCT GCT   1125
361    Tyr Gly Phe Arg His Gln Asn Ala Gln Gly Glu Gly Thr Ala Ala    375

1126   GAC TAC AAA TCA ACA CAA TCA GCT ATC GAC CAA ATC ACA GGT AAA   1170
376    Asp Tyr Lys Ser Thr Gln Ser Ala Ile Asp Gln Ile Thr Gly Lys    390

1171   CTG AAC AGA CTG ATC GAA AAA ACA AAC CAA CAA TTC GAA CTG ATC   1215
391    Leu Asn Arg Leu Ile Glu Lys Thr Asn Gln Gln Phe Glu Leu Ile    405

1216   GAC AAC GAA TTC AAC GAA GTG GAA AAA CAA ATC GGT AAC GTG ATC   1260
406    Asp Asn Glu Phe Asn Glu Val Glu Lys Gln Ile Gly Asn Val Ile    420

1261   AAC TGG ACA AGA GAC TCA ATC ACA GAA GTG TGG TCA TAC AAC GCT   1305
421    Asn Trp Thr Arg Asp Ser Ile Thr Glu Val Trp Ser Tyr Asn Ala    435

1306   GAA CTG CTG GTG GCT ATG GAA AAC CAA CAC ACA ATC GAC CTG GCT   1350
436    Glu Leu Leu Val Ala Met Glu Asn Gln His Thr Ile Asp Leu Ala    450

1351   GAC TCA GAA ATG GAC AAA CTG TAC GAA AGA GTG AAA AGA CAA CTG   1395
451    Asp Ser Glu Met Asp Lys Leu Tyr Glu Arg Val Lys Arg Gln Leu    465

1396   AGA GAA AAC GCT GAA GAA GAC GGT ACA GGT TGC TTC GAA ATC TTC   1440
466    Arg Glu Asn Ala Glu Glu Asp Gly Thr Gly Cys Phe Glu Ile Phe    480

1441   CAC AAA TGC GAC GAC GAC TGC ATG GCT TCA ATC AGA AAC AAC ACA   1485
481    His Lys Cys Asp Asp Asp Cys Met Ala Ser Ile Arg Asn Asn Thr    495

Fig. 14-4

| | | | | | | | | | | | | | | | | |
|---|---|---|---|---|---|---|---|---|---|---|---|---|---|---|---|---|
| SEQ ID NO: 18 cont. | 1486 | TAC | GAC | CAC | TCA | AAA | TAC | AGA | GAA | GAA | GCT | ATG | CAA | AAC | AGA | ATC | 1530 |
| SEQ ID NO: 17 cont. | 496 | Tyr | Asp | His | Ser | Lys | Tyr | Arg | Glu | Glu | Ala | Met | Gln | Asn | Arg | Ile | 510 |

1531 CAA ATC GAC CCT GTG AAA CTG TCA TCA GGT TAC AAA GAC GTG ATC 1575
511  Gln Ile Asp Pro Val Lys Leu Ser Ser Gly Tyr Lys Asp Val Ile 525

1576 CTG TGG TTC TCA TTC GGT GCT TCA TGC TTC ATC CTG CTG GCT ATC 1620
526  Leu Trp Phe Ser Phe Gly Ala Ser Cys Phe Ile Leu Leu Ala Ile 540

1621 GTG ATG GGT CTG GTG TTC ATC TGC GTG AAA AAC GGT AAC ATG AGA 1665
541  Val Met Gly Leu Val Phe Ile Cys Val Lys Asn Gly Asn Met Arg 555

1666 TGC ACA ATC TGC ATC GAC TAC AAA GAC GAC GAC GAC AAA TAA 1707
556  Cys Thr Ile Cys Ile |Asp Tyr Lys Asp Asp Asp Asp Lys| End 569

FLAG tag

Fig. 15

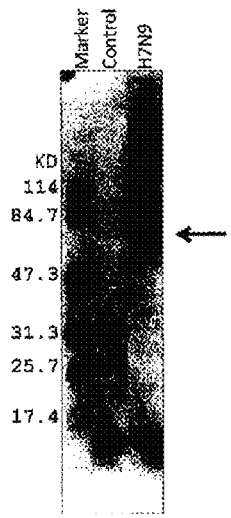

Fig. 16-1

| | | | |
|---|---|---|---|
| SEQ ID NO: 21 | 1 | ATG AAA CTG TCA AAC TTC CAA GGT AAA CTG CTG ATG ACA GTG AAC | 45 |
| SEQ ID NO: 20 | 1 | Met Lys Leu Ser Asn Phe Gln Gly Lys Leu Leu Met Thr Val Asn | 15 |
| | 46 | AAC ACA GAC ATC GCT GAC GTG ATC GTG ATC CCT ACA TCA AAA GGT | 90 |
| | 16 | Asn Thr Asp Ile Ala Asp Val Ile Val Ile Pro Thr Ser Lys Gly | 30 |
| | 91 | GAA AAC AGA TGC TGG GTG AGA GCT ATC GAC GTG GGT TAC ATG TGC | 135 |
| | 31 | Glu Asn Arg Cys Trp Val Arg Ala Ile Asp Val Gly Tyr Met Cys | 45 |
| | 136 | GAA GAC ACA ATC ACA TAC GAA TGC CCT AAA CTG ACA ATG GGT AAC | 180 |
| | 46 | Glu Asp Thr Ile Thr Tyr Glu Cys Pro Lys Leu Thr Met Gly Asn | 60 |
| | 181 | GAC CCT GAA GAC GTG GAC TGC TGG TGC GAC AAC CAA GAA GTG TAC | 225 |
| | 61 | Asp Pro Glu Asp Val Asp Cys Trp Cys Asp Asn Gln Glu Val Tyr | 75 |
| | 226 | GTG CAA TAC GGT AGA TGC ACA AGA ACA AGA CAC TCA AAA AGA TCA | 270 |
| | 76 | Val Gln Tyr Gly Arg Cys Thr Arg Thr Arg His Ser Lys Arg Ser | 90 |
| | 271 | AGA AGA TCA GTG TCA GTG CAA ACA CAC GGT GAA TCA TCA CTG GTG | 315 |
| | 91 | Arg Arg Ser Val Ser Val Gln Thr His Gly Glu Ser Ser Leu Val | 105 |
| | 316 | AAC AAA AAA GAA GCT TGG CTG GAC TCA ACA AAA GCT ACA AGA TAC | 360 |
| | 106 | Asn Lys Lys Glu Ala Trp Leu Asp Ser Thr Lys Ala Thr Arg Tyr | 120 |
| | 361 | CTG ATG AAA ACA GAA AAC TGG ATC GTG AGA AAC CCT GGT TAC GCT | 405 |
| | 121 | Leu Met Lys Thr Glu Asn Trp Ile Val Arg Asn Pro Gly Tyr Ala | 135 |
| | 406 | TTC CTG GCT GCT ATC CTG GGT TGG ATG CTG GGT TCA AAC AAC GGT | 450 |
| | 136 | Phe Leu Ala Ala Ile Leu Gly Trp Met Leu Gly Ser Asn Asn Gly | 150 |
| | 451 | CAA AGA GTG GTG TTC ACA ATC CTG CTG CTG GTG GCT CCT GCT | 495 |
| | 151 | Gln Arg Val Val Phe Thr Ile Leu Leu Leu Val Ala Pro Ala | 165 |

Fig. 16-2

SEQ ID NO: 21 cont.

PrM / M

SEQ ID NO: 20 cont.

| | | | | | | | | | | | | | | | |
|---|---|---|---|---|---|---|---|---|---|---|---|---|---|---|---|
| 496 | TAC | TCA | TTC | AAC | TGC | CTG | GGT | ATG | GGT | AAC | AGA | GAC | TTC | ATC | GAA | 540 |
| 166 | Tyr | Ser | Phe | Asn | Cys | Leu | Gly | Met | Gly | Asn | Arg | Asp | Phe | Ile | Glu | 180 |
| 541 | GGT | GCT | TCA | GGT | GCT | ACA | TGG | GTG | GAC | CTG | GTG | CTG | GAA | GGT | GAC | 585 |
| 181 | Gly | Ala | Ser | Gly | Ala | Thr | Trp | Val | Asp | Leu | Val | Leu | Glu | Gly | Asp | 195 |
| 586 | TCA | TGC | CTG | ACA | ATC | ATG | GCT | AAC | GAC | AAA | CCT | ACA | CTG | GAC | GTG | 630 |
| 196 | Ser | Cys | Leu | Thr | Ile | Met | Ala | Asn | Asp | Lys | Pro | Thr | Leu | Asp | Val | 210 |
| 631 | AGA | ATG | ATC | AAC | ATC | GAA | GCT | GTG | CAA | CTG | GCT | GAA | GTG | AGA | TCA | 675 |
| 211 | Arg | Met | Ile | Asn | Ile | Glu | Ala | Val | Gln | Leu | Ala | Glu | Val | Arg | Ser | 225 |
| 676 | TAC | TGC | TAC | CAC | GCT | TCA | GTG | ACA | GAC | ATC | TCA | ACA | GTG | GCT | AGA | 720 |
| 226 | Tyr | Cys | Tyr | His | Ala | Ser | Val | Thr | Asp | Ile | Ser | Thr | Val | Ala | Arg | 240 |
| 721 | TGC | CCT | ACA | ACA | GGT | GAA | GCT | CAC | AAC | AAA | AAA | AGA | GCT | GAC | TCA | 765 |
| 241 | Cys | Pro | Thr | Thr | Gly | Glu | Ala | His | Asn | Lys | Lys | Arg | Ala | Asp | Ser | 255 |
| 766 | TCA | TAC | GTG | TGC | AAA | CAA | GGT | TTC | ACA | GAC | AGA | GGT | TGG | GGT | AAC | 810 |
| 256 | Ser | Tyr | Val | Cys | Lys | Gln | Gly | Phe | Thr | Asp | Arg | Gly | Trp | Gly | Asn | 270 |
| 811 | GGT | TGC | GGT | CTG | TTC | GGT | AAA | GGT | TCA | ATC | GAC | ACA | TGC | GCT | AAA | 855 |
| 271 | Gly | Cys | Gly | Leu | Phe | Gly | Lys | Gly | Ser | Ile | Asp | Thr | Cys | Ala | Lys | 285 |
| 856 | TTC | TCA | TGC | ACA | TCA | AAA | GCT | ATC | GGT | AGA | ACA | ATC | CAA | CCT | GAA | 900 |
| 286 | Phe | Ser | Cys | Thr | Ser | Lys | Ala | Ile | Gly | Arg | Thr | Ile | Gln | Pro | Glu | 300 |
| 901 | AAC | ATC | AAA | TAC | GAA | GTG | GGT | ATC | TTC | GTG | CAC | GGT | ACA | ACA | ACA | 945 |
| 301 | Asn | Ile | Lys | Tyr | Glu | Val | Gly | Ile | Phe | Val | His | Gly | Thr | Thr | Thr | 315 |
| 946 | TCA | GAA | AAC | CAC | GGT | AAC | TAC | TCA | GCT | CAA | GTG | GGT | GCT | TCA | CAA | 990 |
| 316 | Ser | Glu | Asn | His | Gly | Asn | Tyr | Ser | Ala | Gln | Val | Gly | Ala | Ser | Gln | 330 |

Fig. 16-3

| SEQ ID NO: 21 cont. | 991 | GCT GCT AAA TTC ACA GTG ACA CCT AAC GCT CCT TCA ACA ACA CTG | 1035 |
| SEQ ID NO: 20 cont. | 331 | Ala Ala Lys Phe Thr Val Thr Pro Asn Ala Pro Ser Thr Thr Leu | 345 |
| | 1036 | AAA CTG GGT GAC TAC GGT GAA GTG ACA CTG GAC TGC GAA CCT AGA | 1080 |
| | 346 | Lys Leu Gly Asp Tyr Gly Glu Val Thr Leu Asp Cys Glu Pro Arg | 360 |
| | 1081 | TCA GGT CTG AAC ACA GAA GCT TTC TAC GTG ATG ACA GTG GGT TCA | 1125 |
| | 361 | Ser Gly Leu Asn Thr Glu Ala Phe Tyr Val Met Thr Val Gly Ser | 375 |
| | 1126 | AAA TCA TTC CTG GTG CAC AGA GAA TGG TTC CAC GAC CTG GCT CTG | 1170 |
| | 376 | Lys Ser Phe Leu Val His Arg Glu Trp Phe His Asp Leu Ala Leu | 390 |
| | 1171 | CCT TGG ACA CCT CCT TCA TCA ACA GCT TGG AGA AAC AGA GAA CTG | 1215 |
| | 391 | Pro Trp Thr Pro Pro Ser Ser Thr Ala Trp Arg Asn Arg Glu Leu | 405 |
| | 1216 | CTG ATG GAA TTC GAA GAA GCT CAC GCT ACA AAA CAA TCA GTG GTG | 1260 |
| | 406 | Leu Met Glu Phe Glu Glu Ala His Ala Thr Lys Gln Ser Val Val | 420 |
| | 1261 | GCT CTG GGT TCA CAA GAA GGT GGT CTG CAC CAA GCT CTG GCT GGT | 1305 |
| | 421 | Ala Leu Gly Ser Gln Glu Gly Gly Leu His Gln Ala Leu Ala Gly | 435 |
| | 1306 | GCT ATC GTG GTG GAA TAC TCA AAC TCA GTG AAA CTG ACA TCA GGT | 1350 |
| | 436 | Ala Ile Val Val Glu Tyr Ser Asn Ser Val Lys Leu Thr Ser Gly | 450 |
| | 1351 | CAC CTG AAA TGC AGA CTG AGA ATG GAC AAA CTG GCT CTG AAA GGT | 1395 |
| | 451 | His Leu Lys Cys Arg Leu Arg Met Asp Lys Leu Ala Leu Lys Gly | 465 |
| | 1396 | ACA ACA TAC GGT ATG TGC ACA GAA AAA TTC TCA TTC GCT AAA AAC | 1440 |
| | 466 | Thr Thr Tyr Gly Met Cys Thr Glu Lys Phe Ser Phe Ala Lys Asn | 480 |
| | 1441 | CCT GCT GAC ACA GGT CAC GGT ACA GTG GTG ATC GAA CTG TCA TAC | 1495 |
| | 481 | Pro Ala Asp Thr Gly His Gly Thr Val Val Ile Glu Leu Ser Tyr | 495 |

Fig. 16-4

| | | | |
|---|---|---|---|
| SEQ ID NO: 21 cont. | 1486 | TCA GGT TCA GAC GGT CCT TGC AAA ATC CCT ATC GTG TCA GTG GCT | 1530 |
| SEQ ID NO: 20 cont. | 496 | Ser Gly Ser Asp Gly Pro Cys Lys Ile Pro Ile Val Ser Val Ala | 510 |
| | 1531 | TCA CTG AAC GAC ATG ACA CCT GTG GGT AGA CTG GTG ACA GTG AAC | 1575 |
| | 511 | Ser Leu Asn Asp Met Thr Pro Val Gly Arg Leu Val Thr Val Asn | 525 |
| | 1576 | CCT TTC GTG GCT ACA TCA TCA GCT AAC TCA AAA GTG CTG GTG GAA | 1620 |
| | 526 | Pro Phe Val Ala Thr Ser Ser Ala Asn Ser Lys Val Leu Val Glu | 540 |
| | 1621 | ATG GAA CCT CCT TTC GGT GAC TCA TAC ATC GTG GTG GGT AGA GGT | 1665 |
| | 541 | Met Glu Pro Pro Phe Gly Asp Ser Tyr Ile Val Val Gly Arg Gly | 555 |
| | 1666 | GAC AAA CAA ATC AAC CAC CAC TGG CAC AAA GCT GGT TCA ACA CTG | 1710 |
| | 556 | Asp Lys Gln Ile Asn His His Trp His Lys Ala Gly Ser Thr Leu | 570 |
| | 1711 | GGT AAA GCT TTC TCA ACA ACA CTG AAA GGT GCT CAA AGA CTG GCT | 1755 |
| | 571 | Gly Lys Ala Phe Ser Thr Thr Leu Lys Gly Ala Gln Arg Leu Ala | 585 |
| | 1756 | GCT CTG GGT GAC ACA GCT TGG GAC TTC GGT TCA ATC GGT GGT GTG | 1800 |
| | 586 | Ala Leu Gly Asp Thr Ala Trp Asp Phe Gly Ser Ile Gly Gly Val | 600 |
| | 1801 | TTC AAC TCA ATC GGT AAA GCT GTG CAC CAA GTG TTC GGT GGT GCT | 1845 |
| | 601 | Phe Asn Ser Ile Gly Lys Ala Val His Gln Val Phe Gly Gly Ala | 615 |
| | 1846 | TTC AGA ACA CTG TTC GGT GGT ATG TCA TGG ATC ACA CAA GGT CTG | 1890 |
| | 616 | Phe Arg Thr Leu Phe Gly Gly Met Ser Trp Ile Thr Gln Gly Leu | 630 |
| | 1891 | ATG GGT GCT CTG CTG CTG TGG ATG GGT GTG AAC GCT AGA GAC AGA | 1935 |
| | 631 | Met Gly Ala Leu Leu Leu Trp Met Gly Val Asn Ala Arg Asp Arg | 645 |
| | 1936 | TCA ATC GCT CTG GCT TTC CTG GCT ACA GGT GGT GTG CTG GTG TTC | 1980 |
| | 646 | Ser Ile Ala Leu Ala Phe Leu Ala Thr Gly Gly Val Leu Val Phe | 660 |
| | 1981 | CTG GCT ACA AAC GTG CAC GCT GAC TAC AAA GAC GAC GAC GAC AAA | 2025 |
| | 661 | Leu Ala Thr Asn Val His Ala <u>Asp Tyr Lys Asp Asp Asp Asp Lys</u> | 675 |
| | 2026 | TAA  2028 | |
| | 676 | End  676 | |

FLAG tag

Fig. 18-1

| SEQ ID NO: 24 | 1 | ATG ATC CCT CAA GCT CTG CTG TTC GTG CCT CTG CTG GTG TTC TCA | 45 |
| SEQ ID NO: 23 | 1 | Met Ile Pro Gln Ala Leu Leu Phe Val Pro Leu Leu Val Phe Ser | 15 |
| | 46 | CTG TGC TTC GGT AAA TTC CCT ATC TAC ACA ATC CCT GAC AAA CTG | 90 |
| | 16 | Leu Cys Phe Gly Lys Phe Pro Ile Tyr Thr Ile Pro Asp Lys Leu | 30 |
| | 91 | GGT CCT TGG TCA CCT ATC GAC ATC CAC CAC CTG TCA TGC CCT AAC | 135 |
| | 31 | Gly Pro Trp Ser Pro Ile Asp Ile His His Leu Ser Cys Pro Asn | 45 |
| | 136 | AAC CTG GTG GTG GAA GAC GAA GGT TGC ACA AAC CTG TCA GGT TTC | 180 |
| | 46 | Asn Leu Val Val Glu Asp Glu Gly Cys Thr Asn Leu Ser Gly Phe | 60 |
| | 181 | TCA TAC ATG GAA CTG AAA GTG GGT TAC ATC TCA GCT ATC AAA GTG | 225 |
| | 61 | Ser Tyr Met Glu Leu Lys Val Gly Tyr Ile Ser Ala Ile Lys Val | 75 |
| | 226 | AAC GGT TTC ACA TGC ACA GGT GTG GTG ACA GAA GCT GAA ACA TAC | 270 |
| | 76 | Asn Gly Phe Thr Cys Thr Gly Val Val Thr Glu Ala Glu Thr Tyr | 90 |
| | 271 | ACA AAC TTC GTG GGT TAC GTG ACA ACA ACA TTC AAA AGA AAA CAC | 315 |
| | 91 | Thr Asn Phe Val Gly Tyr Val Thr Thr Thr Phe Lys Arg Lys His | 105 |
| | 316 | TTC AGA CCT ACA CCT GAC GCT TGC AGA GCT GCT TAC AAC TGG AAA | 360 |
| | 106 | Phe Arg Pro Thr Pro Asp Ala Cys Arg Ala Ala Tyr Asn Trp Lys | 120 |
| | 361 | ATG GCT GGT GAC CCT AGA TAC GAA GAA TCA CTG CAC AAC CCT TAC | 405 |
| | 121 | Met Ala Gly Asp Pro Arg Tyr Glu Glu Ser Leu His Asn Pro Tyr | 135 |
| | 406 | CCT GAC TAC CAC TGG CTG AGA ACA GTG AAA ACA ACA AAA GAA TCA | 450 |
| | 136 | Pro Asp Tyr His Trp Leu Arg Thr Val Lys Thr Thr Lys Glu Ser | 150 |
| | 451 | CTG GTG ATC ATC TCA CCT TCA GTG GCT GAC CTG GAC CCT TAC GAC | 495 |
| | 151 | Leu Val Ile Ile Ser Pro Ser Val Ala Asp Leu Asp Pro Tyr Asp | 165 |

Fig. 18-2

| | | | | | | | | | | | | | | |
|---|---|---|---|---|---|---|---|---|---|---|---|---|---|---|
| SEQ ID NO: 24 cont. | 496 | AAA | TCA | CTG | CAC | TCA | AGA | GTG | TTC | CCT | AAC | GGT | AAA | TGC | TCA | GGT | 540 |
| SEQ ID NO: 23 cont. | 166 | Lys | Ser | Leu | His | Ser | Arg | Val | Phe | Pro | Asn | Gly | Lys | Cys | Ser | Gly | 180 |

| | | | | | | | | | | | | | |
|---|---|---|---|---|---|---|---|---|---|---|---|---|---|
| 541 | ATC | ACA | GTG | TCA | TCA | ACA | TAC | TGC | TCA | ACA | AAC | CAC | GAC | TAC | ACA | 585 |
| 181 | Ile | Thr | Val | Ser | Ser | Thr | Tyr | Cys | Ser | Thr | Asn | His | Asp | Tyr | Thr | 195 |

| 586 | ATC | TGG | ATG | CCT | GAA | AAC | CCT | AGA | CTG | GGT | ACA | TCA | TGC | GAC | ATC | 630 |
|---|---|---|---|---|---|---|---|---|---|---|---|---|---|---|---|---|
| 196 | Ile | Trp | Met | Pro | Glu | Asn | Pro | Arg | Leu | Gly | Thr | Ser | Cys | Asp | Ile | 210 |

| 631 | TTC | ACA | AAC | TCA | AGA | GGT | AAA | AGA | GCT | TCA | AAA | GGT | TCA | AAA | ACA | 675 |
|---|---|---|---|---|---|---|---|---|---|---|---|---|---|---|---|---|
| 211 | Phe | Thr | Asn | Ser | Arg | Gly | Lys | Arg | Ala | Ser | Lys | Gly | Ser | Lys | Thr | 225 |

| 676 | TGC | GGT | TTC | GTG | GAC | GAA | AGA | GGT | CTG | TAC | AAA | TCA | CTG | AAA | GGT | 720 |
|---|---|---|---|---|---|---|---|---|---|---|---|---|---|---|---|---|
| 226 | Cys | Gly | Phe | Val | Asp | Glu | Arg | Gly | Leu | Tyr | Lys | Ser | Leu | Lys | Gly | 240 |

| 721 | GCT | TGC | AAA | CTG | AAA | CTG | TGC | GGT | GTG | CTG | GGT | CTG | AGA | CTG | ATG | 765 |
|---|---|---|---|---|---|---|---|---|---|---|---|---|---|---|---|---|
| 241 | Ala | Cys | Lys | Leu | Lys | Leu | Cys | Gly | Val | Leu | Gly | Leu | Arg | Leu | Met | 255 |

| 766 | GAC | GGT | ACA | TGG | GTG | GCT | CTG | CAA | ACA | TCA | GAC | GAA | ACA | AAA | TGG | 810 |
|---|---|---|---|---|---|---|---|---|---|---|---|---|---|---|---|---|
| 256 | Asp | Gly | Thr | Trp | Val | Ala | Leu | Gln | Thr | Ser | Asp | Glu | Thr | Lys | Trp | 270 |

| 811 | TGC | TCA | CCT | GAC | CAA | CTG | GTG | AAC | CTG | CAC | GAC | TTC | CAC | TCA | GAC | 855 |
|---|---|---|---|---|---|---|---|---|---|---|---|---|---|---|---|---|
| 271 | Cys | Ser | Pro | Asp | Gln | Leu | Val | Asn | Leu | His | Asp | Phe | His | Ser | Asp | 285 |

| 856 | GAA | ATC | GAA | CAC | CTG | GTG | GTG | GAA | GAA | CTG | GTG | AAA | AAA | AGA | GAA | 900 |
|---|---|---|---|---|---|---|---|---|---|---|---|---|---|---|---|---|
| 286 | Glu | Ile | Glu | His | Leu | Val | Val | Glu | Glu | Leu | Val | Lys | Lys | Arg | Glu | 300 |

| 901 | GAA | TGC | CTG | GAC | GCT | CTG | GAA | TCA | ATC | ATG | ACA | ACA | AAA | TCA | GTG | 945 |
|---|---|---|---|---|---|---|---|---|---|---|---|---|---|---|---|---|
| 301 | Glu | Cys | Leu | Asp | Ala | Leu | Glu | Ser | Ile | Met | Thr | Thr | Lys | Ser | Val | 315 |

Fig. 18-3

| SEQ ID NO: 24 cont. | 946 | TCA TTC AGA AGA CTG TCA CAC CTG AGA AAA CTG GTG CCT GGT TTC | 990 |
| SEQ ID NO: 23 cont. | 316 | Ser Phe Arg Arg Leu Ser His Leu Arg Lys Leu Val Pro Gly Phe | 330 |
| | 991 | GGT AAA GCT TAC ACA ATC TTC AAC AAA ACA CTG ATG GAA GCT GAC | 1035 |
| | 331 | Gly Lys Ala Tyr Thr Ile Phe Asn Lys Thr Leu Met Glu Ala Asp | 345 |
| | 1036 | GCT CAC TAC AAA TCA ATC AGA ACA TGG AAC GAA ATC ATC CCT TCA | 1080 |
| | 346 | Ala His Tyr Lys Ser Ile Arg Thr Trp Asn Glu Ile Ile Pro Ser | 360 |
| | 1081 | AAA GGT TGC CTG AGA GTG GGT GGT AAA TGC CAC CCT CAC GTG AAC | 1125 |
| | 361 | Lys Gly Cys Leu Arg Val Gly Gly Lys Cys His Pro His Val Asn | 375 |
| | 1126 | GGT GTG TTC TTC AAC GGT ATC ATC CTG GGT CCT GAC GGT CAC GTG | 1170 |
| | 376 | Gly Val Phe Phe Asn Gly Ile Ile Leu Gly Pro Asp Gly His Val | 390 |
| | 1171 | CTG ATC CCT GAA ATG CAA TCA TCA CTG CTG CAC CAA CAC ATG GAA | 1215 |
| | 391 | Leu Ile Pro Glu Met Gln Ser Ser Leu Leu His Gln His Met Glu | 405 |
| | 1216 | CTG CTG GAA TCA TCA GTG ATC CCT CTG ATG CAC CCT CTG GCT GAC | 1260 |
| | 406 | Leu Leu Glu Ser Ser Val Ile Pro Leu Met His Pro Leu Ala Asp | 420 |
| | 1261 | CCT TCA ACA GTG TTC AAA GAC GGT GAC GAA GCT GAA GAC TTC GTG | 1305 |
| | 421 | Pro Ser Thr Val Phe Lys Asp Gly Asp Glu Ala Glu Asp Phe Val | 435 |
| | 1306 | GAA GTG CAC CTG CCT GAC GTG CAC AAA CAA ATC TCA GGT GTG GAC | 1350 |
| | 436 | Glu Val His Leu Pro Asp Val His Lys Gln Ile Ser Gly Val Asp | 450 |
| | 1351 | CTG GGT CTG CCT AAC TGG GGT AAA TAC GTG CTG ATG TCA GCT GGT | 1395 |
| | 451 | Leu Gly Leu Pro Asn Trp Gly Lys Tyr Val Leu Met Ser Ala Gly | 465 |
| | 1396 | GCT CTG ACA GTG CTG ATG CTG ACA ATC TTC CTG GTG ACA TGC TGC | 1440 |
| | 466 | Ala Leu Thr Val Leu Met Leu Thr Ile Phe Leu Val Thr Cys Cys | 480 |

Fig. 18-4

| | | | | | | | | | | | | | | | |
|---|---|---|---|---|---|---|---|---|---|---|---|---|---|---|---|
| SEQ ID NO: 24 cont. | 1441 | AGA | AAA | ACA | AAC | AGA | GCT | GAA | TCA | ATC | CAA | CAC | TCA | TCA | GGT | GAA | 1485 |
| SEQ ID NO: 23 cont. | 481 | Arg | Lys | Thr | Asn | Arg | Ala | Glu | Ser | Ile | Gln | His | Ser | Ser | Gly | Glu | 495 |
| | 1486 | ACA | GGT | AGA | AAA | GTG | TCA | GTG | ACA | TCA | CAA | AAC | GGT | AGA | GTG | ATC | 1530 |
| | 496 | Thr | Gly | Arg | Lys | Val | Ser | Val | Thr | Ser | Gln | Asn | Gly | Arg | Val | Ile | 510 |
| | 1531 | TCA | TCA | TGG | GAA | TCA | TAC | AAA | TCA | GGT | GGT | GAA | ACA | AAA | CTG | GAC | 1575 |
| | 511 | Ser | Ser | Trp | Glu | Ser | Tyr | Lys | Ser | Gly | Gly | Glu | Thr | Lys | Leu | Asp | 525 |
| | 1576 | TAC | AAA | GAC | GAC | GAC | GAC | AAA | taa | 1599 | | | | | | | |
| | 526 | Tyr | Lys | Asp | Asp | Asp | Asp | Lys | End | 533 | | | | | | | |

FLAG tag

Fig. 19-1

```
[GENETYX-MAC: Translation of Nucleotides into Amino Acids for Thesis]
Date            : 2013.07.18
Filename        : WNVpreM_E_tagRSV_0626.nuc
Sequence size   : 2034
Sequence Position: 1 ~ 2034

Translation Position:     1 ~   2034

Genetic Code: Standard Genetic Code 10        20        30        40        50        60
SEQ ID NO: 27   ATGGTGACACTGTCAAACTTCCAAGGTAAAGTGATGATGACAGTGAACGCTACAGACGTG
SEQ ID NO: 26   MetValThrLeuSerAsnPheGlnGlyLysValMetMetThrValAsnAlaThrAspVal 70        80        90       100       110       120
                ACAGACGCTATCACAATCCCTACAGCTGCTGGTAAAAACCTGTGCATCGTGAGAGCTATG
                ThrAspAlaIleThrIleProThrAlaAlaGlyLysAsnLeuCysIleValArgAlaMet 130       140       150       160       170       180
                GACGTGGGTTACCTGTGCGAAGACACAATCACATACGAATGCCCTGTGCTGGCTGCTGGT
                AspValGlyTyrLeuCysGluAspThrIleThrTyrGluCysProValLeuAlaAlaGly 190       200       210       220       230       240
                AACGACCCTGAAGACATCGACTGCTGGTGCACAAAATCATCAGTGTACGTGAGATACGGT
                AsnAspProGluAspIleAspCysTrpCysThrLysSerSerValTyrValArgTyrGly 250       260       270       280       290       300
                AGATGCACAAAAACAAGACACTCAAGAAGATCAAGAAGATCACTGACAGTGCAAACACAC
                ArgCysThrLysThrArgHisSerArgArgSerArgArgSerLeuThrValGlnThrHis 310       320       330       340       350       360
                GGTGAATCAACACTGGCTAACAAAAAAGGTGCTTGGCTGGACTCAACAAAAGCTACAAGA
                GlyGluSerThrLeuAlaAsnLysLysGlyAlaTrpLeuAspSerThrLysAlaThrArg 370       380       390       400       410       420
                TACCTGGTGAAAACAGAATCATGGATCCTGAGAAACCCTGGTTACGCTCTGGTGGCTGCT
                TyrLeuValLysThrGluSerTrpIleLeuArgAsnProGlyTyrAlaLeuValAlaAla 430       440       450       460       470       480
                GTGATCGGTTGGATGCTGGGTTCAAACACAATGCAAAGAGTGGTGTTCGCTATCCTGCTG
                ValIleGlyTrpMetLeuGlySerAsnThrMetGlnArgValValPheAlaIleLeuLeu 490       500       510       520       530       540
                CTGCTGGTGGCTCCTGCTTACTCATTCAACTGCCTGGGTATGTCAAACAGAGACTTCCTG
                LeuLeuValAlaProAlaTyrSerPheAsnCysLeuGlyMetSerAsnArgAspPheLeu 550       560       570       580       590       600
                GAAGGTGTGTCAGGTGCTACATGGGTGGACCTGGTGCTGGAAGGTGACTCATGCGTGACA
                GluGlyValSerGlyAlaThrTrpValAspLeuValLeuGluGlyAspSerCysValThr

Fig. 19-2

```
                   610       620       630       640       650       660
SEQ ID NO: 27 cont. ATCATGTCAAAAGACAAACCTACAATCGACGTGAAAATGATGAACATGGAAGCTGCTAAC
SEQ ID NO: 26 cont. IleMetSerLysAspLysProThrIleAspValLysMetMetAsnMetGluAlaAlaAsn 670       680       690       700       710       720
                   CTGGCTGACGTGAGATCATACTGCTACCTGGCTTCAGTGTCAGACCTGTCAACAAAAGCT
                   LeuAlaAspValArgSerTyrCysTyrLeuAlaSerValSerAspLeuSerThrLysAla 730       740       750       760       770       780
                   GCTTGCCCTACAATGGGTGAAGCTCACAACGAAAAAAGAGCTGACCCTGCTTTCGTGTGC
                   AlaCysProThrMetGlyGluAlaHisAsnGluLysArgAlaAspProAlaPheValCys 790       800       810       820       830       840
                   AAACAAGGTGTGGTGGACAGAGGTTGGGGTAACGGTTGCGGTCTGTTCGGTAAAGGTTCA
                   LysGlnGlyValValAspArgGlyTrpGlyAsnGlyCysGlyLeuPheGlyLysGlySer 850       860       870       880       890       900
                   ATCGACACATGCGCTAAATTCGCTTGCACAACAAAAGCTACAGGTTGGATCATCCAAAAA
                   IleAspThrCysAlaLysPheAlaCysThrThrLysAlaThrGlyTrpIleIleGlnLys 910       920       930       940       950       960
                   GAAAACATCAAATACGAAGTGGCTATCTTCGTGCACGGTCCTACAACAGTGGAATCACAC
                   GluAsnIleLysTyrGluValAlaIlePheValHisGlyProThrThrValGluSerHis 970       980       990       1000      1010      1020
                   GGTAACTACTCAACACAAATCGGTGCTACACAAGCTGGTAGATTCTCAATCACACCTTCA
                   GlyAsnTyrSerThrGlnIleGlyAlaThrGlnAlaGlyArgPheSerIleThrProSer 1030      1040      1050      1060      1070      1080
                   GCTCCTTCATACACACTGAAACTGGGTGAATACGGTGAAGTGACAGTGGACTGCGAACCT
                   AlaProSerTyrThrLeuLysLeuGlyGluTyrGlyGluValThrValAspCysGluPro 1090      1100      1110      1120      1130      1140
                   AGATCAGGTATCGACACATCAGCTTACTACGTGATGTCAGTGGGTGCTAAATCATTCCTG
                   ArgSerGlyIleAspThrSerAlaTyrTyrValMetSerValGlyAlaLysSerPheLeu 1150      1160      1170      1180      1190      1200
                   GTGCACAGAGAATGGTTCATGGACCTGAACCTGCCTTGGTCATCAGCTGGTTCAACAACA
                   ValHisArgGluTrpPheMetAspLeuAsnLeuProTrpSerSerAlaGlySerThrThr 1210      1220      1230      1240      1250      1260
                   TGGAGAAACAGAGAAACACTGATGGAATTCGAAGAACCTCACGCTACAAAACAATCAGTG
                   TrpArgAsnArgGluThrLeuMetGluPheGluGluProHisAlaThrLysGlnSerVal 1270      1280      1290      1300      1310      1320
                   GTGGCTCTGGGTTCACAAGAAGGTGCTCTGCACCAAGCTCTGGCTGGTGCTATCCCTGTG
                   ValAlaLeuGlySerGlnGluGlyAlaLeuHisGlnAlaLeuAlaGlyAlaIleProVal
```

Fig. 19-3

```
                    1330      1340      1350      1360      1370      1380
SEQ ID NO: 27 cont. GAATTCTCATCAAACACAGTGAAACTGACATCAGGTCACCTGAAATGCAGAGTGAAAATG
SEQ ID NO: 26 cont. GluPheSerSerAsnThrValLysLeuThrSerGlyHisLeuLysCysArgValLysMet 1390      1400      1410      1420      1430      1440
                    GAAAAACTGCAACTGAAAGGTACAACATACGGTGTGTGCTCAAAAGCTTTCAAATTCGCT
                    GluLysLeuGlnLeuLysGlyThrThrTyrGlyValCysSerLysAlaPheLysPheAla 1450      1460      1470      1480      1490      1500
                    AGAACACCTGCTGACACAGGTCACGGTACAGTGGTGCTGGAACTGCAATACACAGGTAAA
                    ArgThrProAlaAspThrGlyHisGlyThrValValLeuGluLeuGlnTyrThrGlyLys 1510      1520      1530      1540      1550      1560
                    GACGGTCCTTGCAAAGTGCCTATCTCATCAGTGGCTTCACTGAACGACCTGACACCTGTG
                    AspGlyProCysLysValProIleSerSerValAlaSerLeuAsnAspLeuThrProVal 1570      1580      1590      1600      1610      1620
                    GGTAGACTGGTGACAGTGAACCCTTTCGTGTCAGTGGCTACAGCTAACTCAAAAGTGCTG
                    GlyArgLeuValThrValAsnProPheValSerValAlaThrAlaAsnSerLysValLeu 1630      1640      1650      1660      1670      1680
                    ATCGAACTGGAACCTCCTTTCGGTGACTCATACATCGTGGTGGGTAGAGGTGAACAACAA
                    IleGluLeuGluProProPheGlyAspSerTyrIleValValGlyArgGlyGluGlnGln 1690      1700      1710      1720      1730      1740
                    ATCAACCACCACTGGCACAAATCAGGTTCATCAATCGGTAAAGCTTTCACAACAACACTG
                    IleAsnHisHisTrpHisLysSerGlySerSerIleGlyLysAlaPheThrThrThrLeu 1750      1760      1770      1780      1790      1800
                    AGAGGTGCTCAAAGACTGGCTGCTCTGGGTGACACAGCTTGGGACTTCGGTTCAGTGGGT
                    ArgGlyAlaGlnArgLeuAlaAlaLeuGlyAspThrAlaTrpAspPheGlySerValGly 1810      1820      1830      1840      1850      1860
                    GGTGTGTTCACATCAGTGGGTAAAGCTATCCACCAAGTGTTCGGTGGTGCTTTCAGATCA
                    GlyValPheThrSerValGlyLysAlaIleHisGlnValPheGlyGlyAlaPheArgSer 1870      1880      1890      1900      1910      1920
                    CTGTTCGGTGGTATGTCATGGATCACACAAGGTCTGCTGGGTGCTCTGCTGCTGTGGATG
                    LeuPheGlyGlyMetSerTrpIleThrGlnGlyLeuLeuGlyAlaLeuLeuLeuTrpMet 1930      1940      1950      1960      1970      1980
                    GGTATCAACGCTAGAGACAGATCAATCGCTATGACATTCCTGGCTGTGGGTGGTGTGCTG
                    GlyIleAsnAlaArgAspArgSerIleAlaMetThrPheLeuAlaValGlyGlyValLeu 1990      2000      2010      2020      2030
                    CTGTTCCTGTCAGTGAACGTGCACGCTGACTACAAAGACGACGACGACAAAtaa
                    LeuPheLeuSerValAsnValHisAlaAspTyrLysAspAspAspAspLys***
```

Fig. 20-1

```
{GENETYX-MAC: Translation of Nucleotides into Amino Acids for Thesis}
Date            : 2013.07.18
Filename        : MERS-Cov_SpikewithTag_0626Rev.nuc
Sequence size   : 4086
Sequence Position: 1 - 4086

Translation Position:   1 - 4086

Genetic Code: Standard Genetic Code
```

```
                  10        20        30        40        50        60
SEQ ID NO: 30  ATGATCCACTCAGTGTTCCTGCTGATGTTCCTGCTGACACCTACAGAATCATACGTGGAC
SEQ ID NO: 29  MetIleHisSerValPheLeuLeuMetPheLeuLeuThrProThrGluSerTyrValAsp 70        80        90       100       110       120
               GTGGGTCCTGACTCAATCAAATCAGCTTGCATCGAAGTGGACATCCAACAAACATTCTTC
               ValGlyProAspSerIleLysSerAlaCysIleGluValAspIleGlnGlnThrPhePhe 130       140       150       160       170       180
               GACAAAACATGGCCTAGACCTATCGACGTGTCAAAAGCTGACGGTATCATCTACCCTCAA
               AspLysThrTrpProArgProIleAspValSerLysAlaAspGlyIleIleTyrProGln 190       200       210       220       230       240
               GGTAGAACATACTCAAACATCACAATCACATACCAAGGTCTGTTCCCTTACCAAGGTGAC
               GlyArgThrTyrSerAsnIleThrIleThrTyrGlnGlyLeuPheProTyrGlnGlyAsp 250       260       270       280       290       300
               CACGGTGACATGTACGTGTACTCAGCTGGTCACGCTACAGGTACAACACCTCAAAAACTG
               HisGlyAspMetTyrValTyrSerAlaGlyHisAlaThrGlyThrThrProGlnLysLeu 310       320       330       340       350       360
               TTCGTGGCTAACTACTCACAAGACGTGAAACAATTCGCTAACGGTTTCGTGGTGAGAATC
               PheValAlaAsnTyrSerGlnAspValLysGlnPheAlaAsnGlyPheValValArgIle 370       380       390       400       410       420
               GGTGCTGCTGCTAACTCAACAGGTACAGTGATCATCTCACCTTCAACATCAGCTACAATC
               GlyAlaAlaAlaAsnSerThrGlyThrValIleIleSerProSerThrSerAlaThrIle 430       440       450       460       470       480
               AGAAAAATCTACCCTGCTTTCATGCTGGGTTCATCAGTGGGTAACTTCTCAGACGGTAAA
               ArgLysIleTyrProAlaPheMetLeuGlySerSerValGlyAsnPheSerAspGlyLys 490       500       510       520       530       540
               ATGGGTAGATTCTTCAACCACACACTGGTGCTGCTGCCTGACGGTTGCGGTACACTGCTG
               MetGlyArgPhePheAsnHisThrLeuValLeuLeuProAspGlyCysGlyThrLeuLeu 550       560       570       580       590       600
               AGAGCTTTCTACTGCATCCTGGAACCTAGATCAGGTAACCACTGCCCTGCTGGTAACTCA
               ArgAlaPheTyrCysIleLeuGluProArgSerGlyAsnHisCysProAlaGlyAsnSer
```

Fig. 20-2

```
                        610        620        630        640        650        660
SEQ ID NO: 30 cont.   TACACATCATTCGCTACATACCACACACCTGCTACAGACTGCTCAGACGGTAACTACAAC
SEQ ID NO: 29 cont.   TyrThrSerPheAlaThrTyrHisThrProAlaThrAspCysSerAspGlyAsnTyrAsn 670        680        690        700        710        720
                      AGAAACGCTTCACTGAACTCATTCAAAGAATACTTCAACCTGAGAAACTGCACATTCATG
                      ArgAsnAlaSerLeuAsnSerPheLysGluTyrPheAsnLeuArgAsnCysThrPheMet 730        740        750        760        770        780
                      TACACATACAACATCACAGAAGACGAAATCCTGGAATGGTTCGGTATCACACAAACAGCT
                      TyrThrTyrAsnIleThrGluAspGluIleLeuGluTrpPheGlyIleThrGlnThrAla 790        800        810        820        830        840
                      CAAGGTGTGCACCTGTTCTCATCAAGATACGTGGACCTGTACGGTGGTAACATGTTCCAA
                      GlnGlyValHisLeuPheSerSerArgTyrValAspLeuTyrGlyGlyAsnMetPheGln 850        860        870        880        890        900
                      TTCGCTACACTGCCTGTGTACGACACAATCAAATACTACTCAATCATCCCTCACTCAATC
                      PheAlaThrLeuProValTyrAspThrIleLysTyrTyrSerIleIleProHisSerIle 910        920        930        940        950        960
                      AGATCAATCCAATCAGACAGAAAAGCTTGGGCTGCTTTCTACGTGTACAAACTGCAACCT
                      ArgSerIleGlnSerAspArgLysAlaTrpAlaAlaPheTyrValTyrLysLeuGlnPro 970        980        990       1000       1010       1020
                      CTGACATTCCTGCTGGACTTCTCAGTGGACGGTTACATCAGAAGAGCTATCGACTGCGGT
                      LeuThrPheLeuLeuAspPheSerValAspGlyTyrIleArgArgAlaIleAspCysGly 1030       1040       1050       1060       1070       1080
                      TTCAACGACCTGTCACAACTGCACTGCTCATACGAATCATTCGACGTGGAATCAGGTGTG
                      PheAsnAspLeuSerGlnLeuHisCysSerTyrGluSerPheAspValGluSerGlyVal 1090       1100       1110       1120       1130       1140
                      TACTCAGTGTCATCATTCGAAGCTAAACCTTCAGGTTCAGTGGTGGAACAAGCTGAAGGT
                      TyrSerValSerSerPheGluAlaLysProSerGlySerValValGluGlnAlaGluGly 1150       1160       1170       1180       1190       1200
                      GTGGAATGCGACTTCTCACCTCTGCTGTCAGGTACACCTCCTCAAGTGTACAACTTCAAA
                      ValGluCysAspPheSerProLeuLeuSerGlyThrProProGlnValTyrAsnPheLys 1210       1220       1230       1240       1250       1260
                      AGACTGGTGTTCACAAACTGCAACTACAACCTGACAAAACTGCTGTCACTGTTCTCAGTG
                      ArgLeuValPheThrAsnCysAsnTyrAsnLeuThrLysLeuLeuSerLeuPheSerVal 1270       1280       1290       1300       1310       1320
                      AACGACTTCACATGCTCACAAATCTCACCTGCTGCTATCGCTTCAAACTGCTACTCATCA
                      AsnAspPheThrCysSerGlnIleSerProAlaAlaIleAlaSerAsnCysTyrSerSer
```

Fig. 20-3

SEQ ID NO: 30 cont.
SEQ ID NO: 29 cont.

```
          1330      1340      1350      1360      1370      1380
CTGATCCTGGACTACTTCTCATACCCTCTGTCAATGAAATCAGACCTGTCAGTGTCATCA
LeuIleLeuAspTyrPheSerTyrProLeuSerMetLysSerAspLeuSerValSerSer 1390      1400      1410      1420      1430      1440
GCTGGTCCTATCTCACAATTCAACTACAAACAATCATTCTCAAACCCTACATGCCTGATC
AlaGlyProIleSerGlnPheAsnTyrLysGlnSerPheSerAsnProThrCysLeuIle 1450      1460      1470      1480      1490      1500
CTGGCTACAGTGCCTCACAACCTGACAACAATCACAAAACCTCTGAAATACTCATACATC
LeuAlaThrValProHisAsnLeuThrThrIleThrLysProLeuLysTyrSerTyrIle 1510      1520      1530      1540      1550      1560
AACAAATGCTCAAGACTGCTGTCAGACGACAGAACAGAAGTGCCTCAACTGGTGAACGCT
AsnLysCysSerArgLeuLeuSerAspAspArgThrGluValProGlnLeuValAsnAla 1570      1580      1590      1600      1610      1620
AACCAATACTCACCTTGCGTGTCAATCGTGCCTTCAACAGTGTGGGAAGACGGTGACTAC
AsnGlnTyrSerProCysValSerIleValProSerThrValTrpGluAspGlyAspTyr 1630      1640      1650      1660      1670      1680
TACAGAAAACAACTGTCACCTCTGGAAGGTGGTGGTTGGCTGGTGGCTTCAGGTTCAACA
TyrArgLysGlnLeuSerProLeuGluGlyGlyGlyTrpLeuValAlaSerGlySerThr 1690      1700      1710      1720      1730      1740
GTGGCTATGACAGAACAACTGCAAATGGGTTTCGGTATCACAGTGCAATACGGTACAGAC
ValAlaMetThrGluGlnLeuGlnMetGlyPheGlyIleThrValGlnTyrGlyThrAsp 1750      1760      1770      1780      1790      1800
ACAAACTCAGTGTGCCCTAAACTGGAATTCGCTAACGACACAAAAATCGCTTCACAACTG
ThrAsnSerValCysProLysLeuGluPheAlaAsnAspThrLysIleAlaSerGlnLeu 1810      1820      1830      1840      1850      1860
GGTAACTGCGTGGAATACTCACTGTACGGTGTGTCAGGTAGAGGTGTGTTCCAAAACTGC
GlyAsnCysValGluTyrSerLeuTyrGlyValSerGlyArgGlyValPheGlnAsnCys 1870      1880      1890      1900      1910      1920
ACAGCTGTGGGTGTGAGACAACAAAGATTCGTGTACGACGCTTACCAAAACCTGGTGGGT
ThrAlaValGlyValArgGlnGlnArgPheValTyrAspAlaTyrGlnAsnLeuValGly 1930      1940      1950      1960      1970      1980
TACTACTCAGACGACGGTAACTACTACTGCCTGAGAGCTTGCGTGTCAGTGCCTGTGTCA
TyrTyrSerAspAspGlyAsnTyrTyrCysLeuArgAlaCysValSerValProValSer 1990      2000      2010      2020      2030      2040
GTGATCTACGACAAAGAAACAAAAACACACGCTACACTGTTCGGTTCAGTGGCTTGCGAA
ValIleTyrAspLysGluThrLysThrHisAlaThrLeuPheGlySerValAlaCysGlu
```

Fig. 20-4

```
                      2050      2060      2070      2080      2090      2100
SEQ ID NO: 30 cont.   CACATCTCATCAACAATGTCACAATACTCAAGATCAACAAGATCAATGCTGAAAAGAAGA
SEQ ID NO: 29 cont.   HisIleSerSerThrMetSerGlnTyrSerArgSerThrArgSerMetLeuLysArgArg 2110      2120      2130      2140      2150      2160
                      GACTCAACATACGGTCCTCTGCAAACACCTGTGGGTTGCGTGCTGGGTCTGGTGAACTCA
                      AspSerThrTyrGlyProLeuGlnThrProValGlyCysValLeuGlyLeuValAsnSer 2170      2180      2190      2200      2210      2220
                      TCACTGTTCGTGGAAGACTGCAAACTGCCTCTGGGTCAATCACTGTGCGCTCTGCCTGAC
                      SerLeuPheValGluAspCysLysLeuProLeuGlyGlnSerLeuCysAlaLeuProAsp 2230      2240      2250      2260      2270      2280
                      ACACCTTCAACACTGACACCTAGATCAGTGAGATCAGTGCCTGGTGAAATGAGACTGGCT
                      ThrProSerThrLeuThrProArgSerValArgSerValProGlyGluMetArgLeuAla 2290      2300      2310      2320      2330      2340
                      TCAATCGCTTTCAACCACCCTATCCAAGTGGACCAACTGAACTCATCATACTTCAAACTG
                      SerIleAlaPheAsnHisProIleGlnValAspGlnLeuAsnSerSerTyrPheLysLeu 2350      2360      2370      2380      2390      2400
                      TCAATCCCTACAAACTTCTCATTCGGTGTGACACAAGAATACATCCAAACAACAATCCAA
                      SerIleProThrAsnPheSerPheGlyValThrGlnGluTyrIleGlnThrThrIleGln 2410      2420      2430      2440      2450      2460
                      AAAGTGACAGTGGACTGCAAACAATACGTGTGCAACGGTTTCCAAAAATGCGAACAACTG
                      LysValThrValAspCysLysGlnTyrValCysAsnGlyPheGlnLysCysGluGlnLeu 2470      2480      2490      2500      2510      2520
                      CTGAGAGAATACGGTCAATTCTGCTCAAAAATCAACCAAGCTCTGCACGGTGCTAACCTG
                      LeuArgGluTyrGlyGlnPheCysSerLysIleAsnGlnAlaLeuHisGlyAlaAsnLeu 2530      2540      2550      2560      2570      2580
                      AGACAAGACGACTCAGTGAGAAACCTGTTCGCTTCAGTGAAATCATCACAATCATCACCT
                      ArgGlnAspAspSerValArgAsnLeuPheAlaSerValLysSerSerGlnSerSerPro 2590      2600      2610      2620      2630      2640
                      ATCATCCCTGGTTTCGGTGGTGACTTCAACCTGACACTGCTGGAACCTGTGTCAATCTCA
                      IleIleProGlyPheGlyGlyAspPheAsnLeuThrLeuLeuGluProValSerIleSer 2650      2660      2670      2680      2690      2700
                      ACAGGTTCAAGATCAGCTAGATCAGCTATCGAAGACCTGCTGTTCGACAAAGTGACAATC
                      ThrGlySerArgSerAlaArgSerAlaIleGluAspLeuLeuPheAspLysValThrIle 2710      2720      2730      2740      2750      2760
                      GCTGACCCTGGTTACATGCAAGGTTACGACGACTGCATGCAACAAGGTCCTGCTTCAGCT
                      AlaAspProGlyTyrMetGlnGlyTyrAspAspCysMetGlnGlnGlyProAlaSerAla
```

Fig. 20-5

```
                    2770      2780      2790      2800      2810      2820
SEQ ID NO: 30 cont.  AGAGACCTGATCTGCGCTCAATACGTGGCTGGTTACAAAGTGCTGCCTCCTCTGATGGAC
SEQ ID NO: 29 cont.  ArgAspLeuIleCysAlaGlnTyrValAlaGlyTyrLysValLeuProProLeuMetAsp 2830      2840      2850      2860      2870      2880
                    GTGAACATGGAAGCTGCTTACACATCATCACTGCTGGGTTCAATCGCTGGTGTGGGTTGG
                    ValAsnMetGluAlaAlaTyrThrSerSerLeuLeuGlySerIleAlaGlyValGlyTrp 2890      2900      2910      2920      2930      2940
                    ACAGCTGGTCTGTCATCATTCGCTGCTATCCCTTTCGCTCAATCAATCTTCTACAGACTG
                    ThrAlaGlyLeuSerSerPheAlaAlaIleProPheAlaGlnSerIlePheTyrArgLeu 2950      2960      2970      2980      2990      3000
                    AACGGTGTGGGTATCACACAACAAGTGCTGTCAGAAAACCAAAAACTGATCGCTAACAAA
                    AsnGlyValGlyIleThrGlnGlnValLeuSerGluAsnGlnLysLeuIleAlaAsnLys 3010      3020      3030      3040      3050      3060
                    TTCAACCAAGCTCTGGGTGCTATGCAAACAGGTTTCACAACAACAAACGAAGCTTTCCAC
                    PheAsnGlnAlaLeuGlyAlaMetGlnThrGlyPheThrThrThrAsnGluAlaPheHis 3070      3080      3090      3100      3110      3120
                    AAAGTGCAAGACGCTGTGAACAACAACGCTCAAGCTCTGTCAAAACTGGCTTCAGAACTG
                    LysValGlnAspAlaValAsnAsnAsnAlaGlnAlaLeuSerLysLeuAlaSerGluLeu 3130      3140      3150      3160      3170      3180
                    TCAAACACATTCGGTGCTATCTCAGCTTCAATCGGTGACATCATCCAAAGACTGGACGTG
                    SerAsnThrPheGlyAlaIleSerAlaSerIleGlyAspIleIleGlnArgLeuAspVal 3190      3200      3210      3220      3230      3240
                    CTGGAACAAGACGCTCAAATCGACAGACTGATCAACGGTAGACTGACAACACTGAACGCT
                    LeuGluGlnAspAlaGlnIleAspArgLeuIleAsnGlyArgLeuThrThrLeuAsnAla 3250      3260      3270      3280      3290      3300
                    TTCGTGGCTCAACAACTGGTGAGATCAGAATCAGCTGCTCTGTCAGCTCAACTGGCTAAA
                    PheValAlaGlnGlnLeuValArgSerGluSerAlaAlaLeuSerAlaGlnLeuAlaLys 3310      3320      3330      3340      3350      3360
                    GACAAAGTGAACGAATGCGTGAAAGCTCAATCAAAAAGATCAGGTTTCTGCGGTCAAGGT
                    AspLysValAsnGluCysValLysAlaGlnSerLysArgSerGlyPheCysGlyGlnGly 3370      3380      3390      3400      3410      3420
                    ACACACATCGTGTCATTCGTGGTGAACGCTCCTAACGGTCTGTACTTCATGCACGTGGGT
                    ThrHisIleValSerPheValValAsnAlaProAsnGlyLeuTyrPheMetHisValGly 3430      3440      3450      3460      3470      3480
                    TACTACCCTTCAAACCACATCGAAGTGGTGTCAGCTTACGGTCTGTGCGACGCTGCTAAC
                    TyrTyrProSerAsnHisIleGluValValSerAlaTyrGlyLeuCysAspAlaAlaAsn
```

Fig. 20-6

SEQ ID NO: 30 cont.
SEQ ID NO: 29 cont.

```
          3480      3500      3510      3520      3530      3540
    CCTACAAACTGCATCGCTCCTGTGAACGGTTACTTCATCAAAACAAACAACACAAGAATC
    ProThrAsnCysIleAlaProValAsnGlyTyrPheIleLysThrAsnAsnThrArgIle 3550      3560      3570      3580      3590      3600
    GTGGACGAATGGTCATACACAGGTTCATCATTCTACGCTCCTGAACCTATCACATCACTG
    ValAspGluTrpSerTyrThrGlySerSerPheTyrAlaProGluProIleThrSerLeu 3610      3620      3630      3640      3650      3660
    AACACAAAATACGTGGCTCCTCAAGTGACATACCAAAACATCTCAACAAACCTGCCTCCT
    AsnThrLysTyrValAlaProGlnValThrTyrGlnAsnIleSerThrAsnLeuProPro 3670      3680      3690      3700      3710      3720
    CCTCTGCTGGGTAACTCAACAGGTATCGACTTCCAAGACGAACTGGACGAATTCTTCAAA
    ProLeuLeuGlyAsnSerThrGlyIleAspPheGlnAspGluLeuAspGluPhePheLys 3730      3740      3750      3760      3770      3780
    AACGTGTCAACATCAATCCCTAACTTCGGTTCACTGACACAAATCAACACAACACTGCTG
    AsnValSerThrSerIleProAsnPheGlySerLeuThrGlnIleAsnThrThrLeuLeu 3790      3800      3810      3820      3830      3840
    GACCTGACATACGAAATGCTGTCACTGCAACAAGTGGTGAAAGCTCTGAACGAATCATAC
    AspLeuThrTyrGluMetLeuSerLeuGlnGlnValValLysAlaLeuAsnGluSerTyr 3850      3860      3870      3880      3890      3900
    ATCGACCTGAAAGAACTGGGTAACTACACATACTACAACAAATGGCCTTGGTACATCTGG
    IleAspLeuLysGluLeuGlyAsnTyrThrTyrTyrAsnLysTrpProTrpTyrIleTrp 3910      3920      3930      3940      3950      3960
    CTGGGTTTCATCGCTGGTCTGGTGGCTCTGGCTCTGTGCGTGTTCTTCATCCTGTGCTGC
    LeuGlyPheIleAlaGlyLeuValAlaLeuAlaLeuCysValPhePheIleLeuCysCys 3970      3980      3990      4000      4010      4020
    ACAGGTTGCGGTACAAACTGCATGGGTAAACTGAAATGCAACAGATGCTGCGACAGATAC
    ThrGlyCysGlyThrAsnCysMetGlyLysLeuLysCysAsnArgCysCysAspArgTyr 4030      4040      4050      4060      4070      4080
    GAAGAATACGACCTGGAACCTCACAAAGTGCACGTGCACGACTACAAAGACGACGACGAC
    GluGluTyrAspLeuGluProHisLysValHisValHisAspTyrLysAspAspAspAsp

AAAtaa
    Lys***
```

Fig. 21-1

```
[GENETYX-MAC: Translation of Nucleotides into Amino Acids for Thesis]
Date         : 2013.07.18
Filename     : FMDV_Miyazaki_M-dykddddk-VP4VP2VP3VP12A3C_0627.nuc
Sequence size ; 2937
Sequence Position: 1 - 2937

Translation Position:    1 -  2937

Genetic Code: Standard Genetic Code
```

```
                    10        20        30        40        50        60
SEQ ID NO: 33  ATGGACTACAAAGACGACGACGACAAAGGTGCTGGTCAATCATCACCTGCTACAGGTTCA
SEQ ID NO: 32  MetAspTyrLysAspAspAspAspLysGlyAlaGlyGlnSerSerProAlaThrGlySer 70        80        90       100       110       120
               CAAAACCAATCAGGTAACACAGGTTCAATCATCAACAACTACTACATGCAACAATACCAA
               GlnAsnGlnSerGlyAsnThrGlySerIleIleAsnAsnTyrTyrMetGlnGlnTyrGln 130       140       150       160       170       180
               AACTCAATGGACACACAACTGGGTGACAACGCTATCTCAGGTGGTTCAAACGAAGGTTCA
               AsnSerMetAspThrGlnLeuGlyAspAsnAlaIleSerGlyGlySerAsnGluGlySer 190       200       210       220       230       240
               ACAGACACAACATCAACACACACAACAAACACACAAAACAACGACTGGTTCTCAAGACTG
               ThrAspThrThrSerThrHisThrThrAsnThrGlnAsnAsnAspTrpPheSerArgLeu 250       260       270       280       290       300
               GCTTCATCAGCTTTCTCAGGTCTGTTCGGTGCTCTGCTGGCTGACAAAAAAACAGAAGAA
               AlaSerSerAlaPheSerGlyLeuPheGlyAlaLeuLeuAlaAspLysLysThrGluGlu 310       320       330       340       350       360
               ACAACACTGCTGGAAGACAGAATCCTGACAACAAGAAACGGTCACACAACATCAACAACA
               ThrThrLeuLeuGluAspArgIleLeuThrThrArgAsnGlyHisThrThrSerThrThr 370       380       390       400       410       420
               CAATCATCAGTGGGTGTGACATACGGTTACGCTGTGACAGAAGACGCTGTGTCAGGTCCT
               GlnSerSerValGlyValThrTyrGlyTyrAlaValThrGluAspAlaValSerGlyPro 430       440       450       460       470       480
               AACACATCAGGTCTGGAAACAAGAGTGACACAAGCTGAAAGATTCTTCAAAAAACACCTG
               AsnThrSerGlyLeuGluThrArgValThrGlnAlaGluArgPhePheLysLysHisLeu 490       500       510       520       530       540
               TTCGACTGGACACCTAACCTGGCTTTCGGTCACTGCCACTACCTGGAACTGCCTACAGAA
               PheAspTrpThrProAsnLeuAlaPheGlyHisCysHisTyrLeuGluLeuProThrGlu 550       560       570       580       590       600
               CACAAAGGTGTGTACGGTTCACTGATGGACTCATACGCTTACATGAGAAACGGTTGGGAC
               HisLysGlyValTyrGlySerLeuMetAspSerTyrAlaTyrMetArgAsnGlyTrpAsp
```

Fig. 21-2

```
                     610       620       630       640       650       660
SEQ ID NO: 33 cont.  ATCGAAGTGACAGCTGTGGGTAACCAATTCAACGGTGGTTGCCTGCTGGTGGCTCTGGTG
SEQ ID NO: 32 cont.  IleGluValThrAlaValGlyAsnGlnPheAsnGlyGlyCysLeuLeuValAlaLeuVal 670       680       690       700       710       720
                     CCTGAACTGAAAGAACTGGACACAAGACAAAAATACCAACTGACACTGTTCCCTCACCAA
                     ProGluLeuLysGluLeuAspThrArgGlnLysTyrGlnLeuThrLeuPheProHisGln 730       740       750       760       770       780
                     TTCATCAACCCTAGAACAAACATGACAGCTCACATCAACGTGCCTTTCGTGGGTGTGAAC
                     PheIleAsnProArgThrAsnMetThrAlaHisIleAsnValProPheValGlyValAsn 790       800       810       820       830       840
                     AGATACGACCAATACGCTCTGCACAAACCTTGGACACTGGTGGTGATGGTGGTGGCTCCT
                     ArgTyrAspGlnTyrAlaLeuHisLysProTrpThrLeuValValMetValValAlaPro 850       860       870       880       890       900
                     CTGACAGTGAAAACAGGTGGTTCAGAACAAATCAAAGTGTACATGAACGCTGCTCCTACA
                     LeuThrValLysThrGlyGlySerGluGlnIleLysValTyrMetAsnAlaAlaProThr 910       920       930       940       950       960
                     TACGTGCACGTGGCTGGTGAACTGCCTTCAAAAGAAGGTATCGTGCCTGTGGCTTGCGCT
                     TyrValHisValAlaGlyGluLeuProSerLysGluGlyIleValProValAlaCysAla 970       980       990       1000      1010      1020
                     GACGGTTACGGTAACATGGTGACAACAGACCCTAAAACAGCTGACCCTGTGTACGGTAAA
                     AspGlyTyrGlyAsnMetValThrThrAspProLysThrAlaAspProValTyrGlyLys 1030      1040      1050      1060      1070      1080
                     GTGTTCAACCCTCCTAGAACAAACCTGCCTGGTAGATTCACAAACTTCCTGGACGTGGCT
                     ValPheAsnProProArgThrAsnLeuProGlyArgPheThrAsnPheLeuAspValAla 1090      1100      1110      1120      1130      1140
                     GAAGCTTGCCCTACATTCCTGAGATTCGGTGAAGTGCCTTTCGTGAAAACAGTGAACTCA
                     GluAlaCysProThrPheLeuArgPheGlyGluValProPheValLysThrValAsnSer 1150      1160      1170      1180      1190      1200
                     GGTGACAGACTGCTGGCTAAATTCGACGTGTCACTGGCTGCTGGTCACATGTCAAACACA
                     GlyAspArgLeuLeuAlaLysPheAspValSerLeuAlaAlaGlyHisMetSerAsnThr 1210      1220      1230      1240      1250      1260
                     TACCTGGCTGGTCTGGCTCAATACTACACACAATACTCAGGTACAATGAACATCCACTTC
                     TyrLeuAlaGlyLeuAlaGlnTyrTyrThrGlnTyrSerGlyThrMetAsnIleHisPhe 1270      1280      1290      1300      1310      1320
                     ATGTTCACAGGTCCTACAGACGCTAAAGCTAGATACATGGTGGCTTACGTGCCTCCTGGT
                     MetPheThrGlyProThrAspAlaLysAlaArgTyrMetValAlaTyrValProProGly
```

Fig. 21-3

SEQ ID NO: 33 cont.
SEQ ID NO: 32 cont.

```
           1330      1340      1350      1360      1370      1380
ATGACACCTCCTACAGACCCTGAAAGAGCTGCTCACTGCATCCACTCAGAATGGGACACA
MetThrProProThrAspProGluArgAlaAlaHisCysIleHisSerGluTrpAspThr 1390      1400      1410      1420      1430      1440
GGTCTGAACTCAAAATTCACATTCTCAATCCCTTACCTGTCAGCTGCTGACTACGCTTAC
GlyLeuAsnSerLysPheThrPheSerIleProTyrLeuSerAlaAlaAspTyrAlaTyr 1450      1460      1470      1480      1490      1500
ACAGCTTCAGACGTGGCTGAAGCTACATCAGTGCAAGGTTGGGTGTGCATCTACCAAATC
ThrAlaSerAspValAlaGluAlaThrSerValGlnGlyTrpValCysIleTyrGlnIle 1510      1520      1530      1540      1550      1560
ACACACGGTAAAGCTGAAGGTGACGCTCTGGTGGTGTCAGCTTCAGCTGGTAAAGACTTC
ThrHisGlyLysAlaGluGlyAspAlaLeuValValSerAlaSerAlaGlyLysAspPhe 1570      1580      1590      1600      1610      1620
GAATTCAGACTGCCTGTGGACGCTAGACAACAAACAACAACAGGTGAATCAGCTGAC
GluPheArgLeuProValAspAlaArgGlnGlnThrThrThrGlyGluSerAlaAsp 1630      1640      1650      1660      1670      1680
CCTGTGACAACAACAGTGGAAAACTACGGTGGTGAAACACAAACAGCTAGAAGACTGCAC
ProValThrThrThrValGluAsnTyrGlyGlyGluThrGlnThrAlaArgArgLeuHis 1690      1700      1710      1720      1730      1740
ACAGACGTGGCTTTCGTGCTGGACAGATTCGTGAAATTCACACCTAAAAACACACAAACA
ThrAspValAlaPheValLeuAspArgPheValLysPheThrProLysAsnThrGlnThr 1750      1760      1770      1780      1790      1800
CTGGACCTGATGCAAATCCCTTCACACACACTGGTGGGTGCTCTGCTGAGATCAGCTACA
LeuAspLeuMetGlnIleProSerHisThrLeuValGlyAlaLeuLeuArgSerAlaThr 1810      1820      1830      1840      1850      1860
TACTACTTCTCAGACCTGGAAATCGCTCTGGTGCACACAGGTCCTGTGACATGGGTGCCT
TyrTyrPheSerAspLeuGluIleAlaLeuValHisThrGlyProValThrTrpValPro 1870      1880      1890      1900      1910      1920
AACGGTGCTCCTAAAACAGCTCTGGACAACCAAACAAACCCTACAGCTTACCACAAACAA
AsnGlyAlaProLysThrAlaLeuAspAsnGlnThrAsnProThrAlaTyrHisLysGln 1930      1940      1950      1960      1970      1980
CCTATCACAAGACTGGCTCTGCCTTACACAGCTCCTCACAGAGTGCTGGCTACAGTGTAC
ProIleThrArgLeuAlaLeuProTyrThrAlaProHisArgValLeuAlaThrValTyr 1990      2000      2010      2020      2030      2040
AACGGTAAAACAACATACGGTGAAGAACCTACAATGAGAGGTGACAGAGCTGTGCTGGCT
AsnGlyLysThrThrTyrGlyGluGluProThrMetArgGlyAspArgAlaValLeuAla
```

Fig. 21-4

SEQ ID NO: 33 cont.
SEQ ID NO: 32 cont.

```
          2050      2060      2070      2080      2090      2100
TCAAAAGTGAACAAACAACTGCCTACATCATTCAACTACGGTGCTGTGAAAGCTGAAAAC
SerLysValAsnLysGlnLeuProThrSerPheAsnTyrGlyAlaValLysAlaGluAsn 2110      2120      2130      2140      2150      2160
ATCACAGAAATGCTGATCAGAATCAAAAGAGCTGAAACATACTGCCCTAGACCTCTGCTG
IleThrGluMetLeuIleArgIleLysArgAlaGluThrTyrCysProArgProLeuLeu 2170      2180      2190      2200      2210      2220
GCTCTGGACACAACACAAGACAGAAGAAAACAAGAAATCATCGCTCCTGAAAAACAACTG
AlaLeuAspThrThrGlnAspArgArgLysGlnGluIleIleAlaProGluLysGlnLeu 2230      2240      2250      2260      2270      2280
CTGAACTTCGACCTGCTGAAACTGGCTGGTGACGTGGAATCAAACCCTGGTCCTTTCTTC
LeuAsnPheAspLeuLeuLysLeuAlaGlyAspValGluSerAsnProGlyProPhePhe 2290      2300      2310      2320      2330      2340
TTCTCAGACGTGAGATCAGGTGCTCCTCCTACAGACCTGCAAAAAATGGTGATGGGTAAC
PheSerAspValArgSerGlyAlaProProThrAspLeuGlnLysMetValMetGlyAsn 2350      2360      2370      2380      2390      2400
ACAAAACCTGTGGAACTGATCCTGGACGGTAAAACAGTGGCTATCTGCTGCGCTACAGGT
ThrLysProValGluLeuIleLeuAspGlyLysThrValAlaIleCysCysAlaThrGly 2410      2420      2430      2440      2450      2460
GTGTTCGGTACAGCTTACCTGGTGCCTAGACACCTGTTCGCTGAAAAATACGACAAAATC
ValPheGlyThrAlaTyrLeuValProArgHisLeuPheAlaGluLysTyrAspLysIle 2470      2480      2490      2500      2510      2520
ATGCTGGACGGTAGAGCTATGACAGACTCAGACTACAGAGTGTTCGAATTCGAAATCAAA
MetLeuAspGlyArgAlaMetThrAspSerAspTyrArgValPheGluPheGluIleLys 2530      2540      2550      2560      2570      2580
GTGAAAGGTCAAGACATGCTGTCAGACGCTGCTCTGATGGTGCTGCACAGAGGTAACAGA
ValLysGlyGlnAspMetLeuSerAspAlaAlaLeuMetValLeuHisArgGlyAsnArg 2590      2600      2610      2620      2630      2640
GTGAGAGACATCACAAAACACTTCAGAGACGTGGCTAGAATGAAAAAAGGTACACCTGTG
ValArgAspIleThrLysHisPheArgAspValAlaArgMetLysLysGlyThrProVal 2650      2660      2670      2680      2690      2700
GTGGGTGTGATCAACAACGCTGACGTGGGTAGACTGATCTTCTCAGGTGAAGCTCTGACA
ValGlyValIleAsnAsnAlaAspValGlyArgLeuIlePheSerGlyGluAlaLeuThr 2710      2720      2730      2740      2750      2760
TACAAGACATCGTGGTGTGCATGGACGGTGACACAATGCCTGGTCTGTTCGCTTACAAA
TyrLysAspIleValValCysMetAspGlyAspThrMetProGlyLeuPheAlaTyrLys
```

Fig. 21-5

```
                    2770      2780      2790      2800      2810      2820
SEQ ID NO: 33 cont.  GCTGCTACAAAAGCTGGTTACTGCGGTGGTGCTGTGCTGGCTAAAGACGGTGCTGAAACA
SEQ ID NO: 32 cont.  AlaAlaThrLysAlaGlyTyrCysGlyGlyAlaValLeuAlaLysAspGlyAlaGluThr 2830      2840      2850      2860      2870      2880
                     TTCATCGTGGGTACACACTCAGCTGGTGGTAACGGTGTGGGTTACTGCTCATGCGTGTCA
                     PheIleValGlyThrHisSerAlaGlyGlyAsnGlyValGlyTyrCysSerCysValSer 2890      2900      2910      2920      2930
                     AGATCAATGCTGCTGAAAATGAAAGCTCACATCGACCCTGAACCTCACCACGAAtaa
                     ArgSerMetLeuLeuLysMetLysAlaHisIleAspProGluProHisHisGlu***
```

… # ISOLATED NUCLEIC ACID FOR THE PRODUCTION OF A VACCINE AGAINST VIRUS

TECHNICAL FIELD

The present invention relates to a nucleic acid for a vaccine, a vector comprising the nucleic acid, *Bombyx mori* comprising the vector, and a method for producing a vaccine in which they are used.

BACKGROUND ART

The deployment of vaccine countermeasures against human diseases is currently an issue of critical importance. For example, the following problems have occurred with respect to influenza. Although the proteins hemagglutinin (HA) and neuraminidase (NA) are present on the surface of influenza virus particles, there are 16 types of HA subtypes and 9 types of NA subtypes, and all of these subtypes are present in birds. Among these, highly virulent (highly pathogenic) viruses that kill large numbers of birds are limited to the H5 and H7 subtypes. Influenza caused by a virulent virus having the H5 subtype was first discovered in 1961 in South Africa after spreading among sea birds in the form of the common term. Since then, the virus spread throughout the US in 1983 and 1984, spread to chickens and humans in Hong Kong in 1997, and has since spread throughout all regions of the world. An inactivated whole-virus vaccine for use in humans and chickens has already been developed for the purpose of its prevention. Moreover, the H7 virus, which demonstrates potent virulence in birds, spread throughout the world starting in 1927. It was responsible for a large number of human victims in the Netherlands in the latter half of the 1980s in particular, and after the H7N7 virus had spread to domestic poultry in 2003 as well, it was confirmed to have infected 89 persons and caused 1 death. Subsequent surveys revealed that 59% of persons who had contact with infected poultry were antibody-positive and it is estimated that at least 1,000 people were infected. Moreover, the avian influenza that occurred in China starting in March 2013 also spread to humans, and its cause was determined to be an attenuated strain of the H7N9 subtype.

In addition, hepatitis C virus not only induces symptoms of acute hepatitis through its infection, but also plays a significant negative role in chronic hepatitis and the subsequent onset of cirrhosis and its subsequent escalation to liver cancer. There are two types of viral hepatitis, consisting of that in which infection spreads by oral infection and that which infects through the blood, with the latter being represented by hepatitis B virus and hepatitis C virus. Although vaccines have recently come to be able to be used for hepatitis B virus, with respect to hepatitis C, although there has been considerable progress in the area of chemotherapy, there is still no definitive treatment that is effective against all virus strains, and although research is being aggressively conducted primarily in advanced nations, there is essentially no vaccine that can be provided for practical use.

The causative virus of Japanese encephalitis is a virus that was isolated in Japan in 1935, and there were numerous patients of this disease in Japan at the time. Subsequently, a vaccine inoculation was developed in 1954, after which the number of patients decreased dramatically to the extent that fewer than 10 patients per year have been reported since 1992. However, this does not mean that the virus is no longer present in Japan. Although Japanese encephalitis is thought to infect humans from pigs by being transmitted by mosquitoes, the serum of a large number of pigs in Japan are positive for anti-Japanese encephalitis antibody even at present. In addition, in looking overseas, patients having this disease occur at the rate of 35,000 to 50,000 patients annually, primarily in Asia, with about 10,000 to 15,000 fatalities, thus making this an important infectious disease that requires countermeasures. Inoculation with the vaccine currently used in Japan began in 2009, and is considered to have fewer adverse side-effects than previous vaccines. However, two fatalities from this disease were reported in 2012 in patients who had received inoculations against the disease. In consideration of these circumstances, there is clearly an urgent need to develop a vaccine that is inexpensive and demonstrates few adverse side-effects.

Japan, along with the UK, Australia, New Zealand, Taiwan and Sweden, is one of the exceptional countries where there are no outbreaks of rabies. Outbreaks have occurred in other countries, and these outbreaks cause 30,000 to 50,000 deaths annually. Rabies virus is able to propagate in numerous wild animals, and it is necessary to introduce immunity into wild animals in order to completely prevent rabies. Live vaccines using recombinant vaccinia virus have been effective and are currently attracting attention. However, although problems have yet to be reported at present, the possibility cannot be denied that the wide-ranging introduction of live vaccines into the natural world will lead to unexpected results. Thus, there is a desire for the development of an inexpensive and effective oral inactivated vaccine.

The West Nile virus was first isolated in Uganda in 1935. The infection cycle of this virus exists between birds and mosquitoes and human may occasionally be infected by mosquitoes. Although the rate at which an infected person exhibits symptoms is about 80%, patients with the disease exhibit serious encephalitis and meningitis symptoms at the rate of about 1 in 150 persons, with the disease being fatal in 3% to 15% of serious cases. This disease had not infiltrated the western hemisphere until the occurrence of an outbreak in New York in the summer of 1999. Infected persons have since appeared throughout nearly the entire US, and there is the risk of this disease eventually invading Japan. 36,500 patients have been confirmed in the US during the period from 1999 to 2012, and 1,500 of those patients have died. Mosquitoes already present in Japan are considered to have the ability to transmit this virus, and as such, the entry of this disease into Japan is most likely just a matter of time. Thus, there is an urgent need to develop an effective vaccine.

PRIOR ART DOCUMENTS

Patent Documents

Patent Document 1: International Publication No. WO 2007/046439

Non-Patent Documents

Non-Patent Document 1: Maeda, S. et al., Nature (1985), 315, 592-594

DISCLOSURE OF THE INVENTION

Problems to be Solved by the Invention

Despite such circumstances, the production of influenza vaccine still traditionally uses fertilized eggs at 10 to 11 days of development. Production in cultured MDCK or VERO cells has also become possible through progress made in current science and technology. What is particularly noteworthy is that proteins for a target influenza vaccine have become able to be produced in yeast or silkworm (*Bombyx mori*) individuals or in *Bombyx mori* cultured cells with gene manipulation technologies using various vectors. The inventors of the present invention succeeded in large-volume production of the HA protein of the H5 avian influenza virus in *Bombyx mori* in 1998. At that time, the gene used was obtained by reverse-transcribing DNA encoding hemagglutinin (HA) protein from A/HK/483/97 (H5N1) influenza RNA virus isolated from humans in Hong Kong in 1997, followed by cloning the DNA in an *E. coli* plasmid. DNA encoding HA protein for producing an influenza vaccine was further recombined in a baculovirus transfer vector to carry out production of the vaccine protein.

The hemagglutination activity (HA activity) of *Bombyx mori* infected with a recombinant baculovirus produced by this method demonstrated a value of 8,192 on day 5 of infection. As a result, in the case of comparing with the typical HA activity of vaccine virus produced in embryonated chicken eggs of 1,024, since the volume of virus liquid produced from a single embryonated chicken egg is about 10 ml, the total HA activity becomes 10,240. On the other hand, the average value of total HA activity in 15 ml of HA protein solution produced by a single *Bombyx mori* demonstrates a value of 122,800, and this corresponds to a production ratio that is roughly 12 times higher. This represents the expression efficiency realized by conventional technology by which naturally-occurring, highly pathogenic avian influenza virus HA was produced in baculovirus vector without altering DNA design.

The production of vaccine from embryonated chicken eggs requires a large-scale facility such as a P3 facility for handling seed viruses used in vaccines, and is associated with various problems such as the high cost of obtaining safe seed viruses without altering antigenicity, the need to create a facility for safely handling infectious viruses for safely producing vaccines and the high costs in terms of both equipment and production, the fact that these vaccines can cause egg allergies, the need for a large volume of eggs, the risk of occasionally causing changes in antigenicity in order to increase the amount of virus in chicken eggs, and the difficulty in manufacturing component vaccines consisting of the active component only. On the other hand, vaccine production technologies using *Bombyx mori* thus far required the addition of surfactants.

In this manner, there were limitations in terms of costs and production volume on conventional technologies used to produce vaccines using embryonated chicken eggs, and the production of HA only as the active component has considerable problems with respect to cost and purification technology. A novel technology for large-volume production of HA protein will therefore be necessary in order to overcome these problems. [Is this supposed to be a separate paragraph or not?]

Accordingly, an object of the present invention is to provide a nucleic acid for a vaccine, a vector the nucleic acid, *Bombyx mori* comprising the vector, and a method for producing a vaccine using them.

Means for Solving the Problems

As a result of conducting extensive studies, the inventors of the present invention found for the first time that the titer of a vaccine protein produced by *Bombyx mori* can be increased significantly by using a nucleic acid sequence that has undergone codon optimization for expression in *Bombyx mori*, thereby leading to completion of the present invention.

Namely, the present invention is as follows:

[1] a nucleic acid comprising the nucleic acid sequence of a virus that has undergone codon optimization for expression in *Bombyx mori* for the production of a vaccine against that virus in *Bombyx mori*;

[2] the nucleic acid described in [1], wherein the virus is selected from the group consisting of influenza virus, hepatitis C virus, Japanese encephalitis virus, rabies virus, West Nile virus, MERS coronavirus and foot and mouth disease virus;

[3] the nucleic acid described in [2], wherein the virus is type A influenza virus;

[4] the nucleic acid described in [3], wherein the virus is selected from the group consisting of subtypes H5 and H 7;

[5] the nucleic acid described in [4], wherein the nucleic acid sequence encodes influenza virus HA protein;

[6] the nucleic acid described in [5], wherein the nucleic acid sequence has been modified to attenuate the influenza virus HA protein;

[7] the nucleic acid described in any of [1] to [6], wherein the nucleic acid sequence is a nucleic acid sequence selected from the group consisting of SEQ ID NO: 4, SEQ ID NO: 12 and SEQ ID NO: 18;

[8] the nucleic acid described in [2], wherein the virus is hepatitis C virus;

[9] the nucleic acid described in [8], wherein the nucleic acid sequence encodes an E1 protein, an E2 protein and/or a nuclear protein of hepatitis C virus;

[10] the nucleic acid described in [8], wherein the nucleic acid sequence encodes an E1 protein, an E2 protein and a nuclear protein of hepatitis C virus;

[11] the nucleic acid described in [10], wherein the nucleic acid sequence is SEQ ID NO: 15;

[12] the nucleic acid described in [2], wherein the nucleic acid sequence is SEQ ID NO: 4, 12, 15, 18, 21, 24, 27, 30 or 33;

[13] a vector comprising the nucleic acid described in any of [1] to [12];

[14] a recombinant baculovirus produced using the vector described in [13];

[15] *Bombyx mori* comprising the nucleic acid described in any of [1] to [12], the vector described in [13], or the recombinant baculovirus described in [14];

[16] a polypeptide composed of an amino acid sequence encoded by the nucleic acid described in any of [1] to [12];

[17] a method for producing a vaccine that uses the nucleic acid described in any of [1] to [12], the vector described in [13], the recombinant baculovirus described in [14] or the *Bombyx mori* described in [15];

[18] the method for producing a vaccine described in [17], comprising the following steps:

1) a step for obtaining the nucleic acid described in any of [1] to [12], the vector described in [13] or the recombinant baculovirus described in [14], 2) a step for introducing the nucleic acid described in any of [1] to [12], the vector described in [13] or the recombinant baculovirus described in [14] into *Bombyx mori*, and 3) a step for recovering protein from *Bombyx mori*;

[19] a vaccine comprising the polypeptide described in [16] or a vaccine produced according to the production method described in [17] or [18] for vaccinating an animal against a viral infection;

[20] the vaccine described in [19], which has a virus-like particle structure;

[21] the vaccine described in [20], wherein the diameter of the virus-like particle structure is 50 nm to 150 nm;

[22] a method for inoculating an animal with a vaccine against a viral infection, comprising: administering to the animal an effective amount of a vaccine comprising the HA polypeptide described in [16] or a vaccine produced according to the production method described in [17] or [18]; and,

[23] a method for inducing an immune response to a virus in an animal, comprising: administering to the animal an effective amount of a vaccine comprising the polypeptide described in [16] or a vaccine produced according to the production method described in [17] or [18].

Effects of the Invention

According to the present invention, a nucleic acid for a vaccine having a higher titer, a vector comprising the nucleic acid, *Bombyx mori* comprising the vector, and a method for producing a vaccine by using them are provided.

BRIEF DESCRIPTION OF THE DRAWINGS

FIG. 1 is a table showing codon usage frequencies in *Bombyx mori* obtained by investigating the usage frequencies among 450043 codons in 1180 coding regions (CDS) of *Bombyx mori*. The table shows the frequencies of occurrence per 1000 of each codon. Numbers in parentheses indicate the total number expressed. Boldface characters indicate the gene codons having the highest usage frequency for each amino acid.

FIG. 2 is a codon correspondence table that has been optimized based on the gene codons having the highest usage frequency shown in FIG. 1. The serine (S) codon is UCA, and the codon of its complementary strand is TGA, which is also the stop codon. Consequently, the complementary strand of serine is the stop codon, and large frames do not appear in the complementary strain.

FIG. 3-1 indicates the correspondence between an HA gene DNA sequence codon-optimized for avian influenza virus A/tufted duck/Fukushima/16/2011 (H5N1) and an amino acid sequence. The base sequence of a synthetic gene was determined based on the base sequence of the HA gene of highly pathogenic avian influenza virus A/tufted duck/Fukushima/16/2011 (H5N1) in consideration of attenuation, the introduction of a FLAG tag on the C terminal, and optimization of the codon usage frequency of *Bombyx mori* cells. The amino acid sequence predicted from the base sequence of the synthetic gene is also shown.

FIG. 3-2 indicates the correspondence between an HA gene DNA sequence codon-optimized for avian influenza virus A/tufted duck/Fukushima/16/2011 (H5N1) and an amino acid sequence. The base sequence of a synthetic gene was determined based on the base sequence of the HA gene of highly pathogenic avian influenza virus A/tufted duck/Fukushima/16/2011 (H5N1) in consideration of attenuation, the introduction of a FLAG tag on the C terminal, and optimization of the codon usage frequency of *Bombyx mori* cells. The amino acid sequence predicted from the base sequence of the synthetic gene is also shown.

FIG. 3-3 indicates the correspondence between an HA gene DNA sequence codon-optimized for avian influenza virus A/tufted duck/Fukushima/16/2011 (H5N1) and an amino acid sequence. The enclosed portion indicates the attenuation site. The base sequence of a synthetic gene was determined based on the base sequence of the HA gene of highly pathogenic avian influenza virus A/tufted duck/Fukushima/16/2011 (H5N1) in consideration of attenuation, the introduction of a FLAG tag on the C terminal, and optimization of the codon usage frequency of *Bombyx mori* cells. The amino acid sequence predicted from the base sequence of the synthetic gene is also shown.

FIG. 3-4 indicates the correspondence between an HA gene DNA sequence codon-optimized for avian influenza virus A/tufted duck/Fukushima/16/2011 (H5N1) and an amino acid sequence. The enclosed portion indicates the FLAG tag. The base sequence of a synthetic gene was determined based on the base sequence of the HA gene of highly pathogenic avian influenza virus A/tufted duck/Fukushima/16/2011 (H5N1) in consideration of attenuation, the introduction of an FLAG tag on the C terminal, and optimization of the codon usage frequency of *Bombyx mori* cells. The amino acid sequence predicted from the base sequence of the synthetic gene is also shown.

FIG. 4 shows the results of analyzing the coding frames of a gene encoding a synthesized vaccine HA protein. N1>-, N2>- and N3>- starting from the bottom indicate the results of analyzing three coding frames for each plus strand. The bar on top indicates the location of the start codon ATG, while the downward protruding bars indicate the locations of stop codons (TAA, TAG, TGA). Although only N1>- constitutes a single large coding frame, the other frames have a large number of downwardly protruding bars, and would be unable to produce a large protein even if they were expressed. N1<-, N2<- and N3<-starting from the fourth result from the bottom to the top indicate the results of analyzing coding frames of the complementary strand. Each of these frames would also be unable to produce a large protein even if expressed.

FIG. 5-1 indicates the alignment between a codon-optimized HA gene DNA sequence and an HA gene cDNA sequence of avian influenza virus A/tufted duck/Fukushima/16/2011 (H5N1). Query indicates the codon-optimized HA gene DNA sequence (coding region sequence excluding the FLAG tag), while Sbjct indicates avian influenza virus A/tufted duck/Fukushima/16/2011 (H5N1) (HA coding region sequence). Those portions where the sequences are the same are indicated with asterisks (*), while "-" symbols indicate gaps. Although homology is extremely low at 77%, the sequences are designed so as to express the same amino acid sequence with the exception of modifying and deleting the attenuated sequence.

FIG. 5-2 indicates the alignment between a codon-optimized HA gene DNA sequence and an HA gene cDNA sequence of avian influenza virus A/tufted duck/Fukushima/16/2011 (H5N1). Query indicates the codon-optimized HA gene DNA sequence (coding region sequence excluding the FLAG tag), while Sbjct indicates avian influenza virus A/tufted duck/Fukushima/16/2011 (H5N1) (HA coding region sequence). Those portions where the sequences are the same are indicated with asterisks (*), while "-" symbols indicate gaps. Although homology is extremely low at 77%, the sequences are designed so as to express the same amino acid sequence with the exception of modifying and deleting the attenuated sequence.

FIG. 6 indicates confirmation of expression of HA protein from codon-optimized HA gene of avian influenza virus A/chicken/tufted duck/Fukushima/16/2011 (H5N1) produced using *Bombyx mori* by western blotting. Marker indicates molecular weight markers. Control indicates uninfected *Bombyx mori*. Fukushima indicates *Bombyx mori* infected with codon-optimized HA gene. The arrow indicates a specific band.

FIG. 7 indicates HI activity of HI antibody to various influenza viruses in chickens using an HA solution prepared using pBm-8HA. The antibody reacted with a wide range of naturally-occurring viruses.

FIG. 8 indicates HA activity of various fractions of a sucrose density gradient. HA activity was distributed at a location indicating a lower density than the location where naturally-occurring virus precipitates.

FIG. 10-1 indicates the correspondence between an HA gene DNA sequence codon-optimized for avian influenza virus A/chicken/Sukabumi/2008 (H5N1) and an amino acid sequence. The base sequence of a synthetic gene was designed based on the base sequence of the HA gene of avian influenza virus A/chicken/Sukabumi/2008 (H5N1) in consideration of the introduction of a FLAG tag on the C terminal and optimization of the codon usage frequency of *Bombyx mori* cells. The amino acid sequence predicted from the base sequence of the synthetic gene is also shown.

FIG. 10-2 indicates the correspondence between an HA gene DNA sequence codon-optimized for avian influenza virus A/chicken/Sukabumi/2008 (H5N1) and an amino acid sequence. The base sequence of a synthetic gene was designed based on the base sequence of the HA gene of avian influenza virus A/chicken/Sukabumi/2008 (H5N1) in consideration of the introduction of a FLAG tag on the C terminal and optimization of the codon usage frequency of *Bombyx mori* cells. The amino acid sequence predicted from the base sequence of the synthetic gene is also shown.

FIG. 10-3 indicates the correspondence between an HA gene DNA sequence codon-optimized for avian influenza virus A/chicken/Sukabumi/2008 (H5N1) and an amino acid sequence. The enclosed portion indicates the attenuation site. The base sequence of a synthetic gene was designed based on the base sequence of the HA gene of avian influenza virus A/chicken/Sukabumi/2008 (H5N1) in consideration of the introduction of a FLAG tag on the C terminal and optimization of the codon usage frequency of *Bombyx mori* cells. The amino acid sequence predicted from the base sequence of the synthetic gene is also shown.

FIG. 10-4 indicates the correspondence between an HA gene DNA sequence codon-optimized for avian influenza virus A/chicken/Sukabumi/2008 (H5N1) and an amino acid sequence. The enclosed portion indicates the FLAG tag. The base sequence of a synthetic gene was designed based on the base sequence of the HA gene of avian influenza virus A/chicken/Sukabumi/2008 (H5N1) in consideration of the introduction of a FLAG tag on the C terminal and optimization of the codon usage frequency of *Bombyx mori* cells. The amino acid sequence predicted from the base sequence of the synthetic gene is also shown.

FIG. 11 indicates confirmation of expression of HA protein from codon-optimized HA gene of avian influenza virus A/chicken/Sukabumi/2008 (H5N1) produced using *Bombyx mori* by western blotting. Marker indicates molecular weight markers. Control indicates uninfected *Bombyx mori*. Sukabumi indicates *Bombyx mori* infected with codon-optimized HA gene. The arrow indicates a specific band.

FIG. 12-1 indicates the correspondence between a core-E1-E2 fused protein DNA sequence codon-optimized for hepatitis C virus and an amino acid sequence. Core protein: DNA sequence positions 1 to 573, E1 protein: positions 574 to 1149, E3 protein: positions 1150 to 2238, FLAG tag: positions 2239 to 2262.

FIG. 12-2 indicates the correspondence between a core-E1-E2 fused protein DNA sequence codon-optimized for hepatitis C virus and an amino acid sequence. Core protein: DNA sequence positions 1 to 573, E1 protein: positions 574 to 1149, E3 protein: positions 1150 to 2238, FLAG tag: positions 2239 to 2262.

FIG. 12-3 indicates the correspondence between a core-E1-E2 fused protein DNA sequence codon-optimized for hepatitis C virus and an amino acid sequence. Core protein: DNA sequence positions 1 to 573, E1 protein: positions 574 to 1149, E3 protein: positions 1150 to 2238, FLAG tag: positions 2239 to 2262.

FIG. 12-4 indicates the correspondence between a core-E1-E2 fused protein DNA sequence codon-optimized for hepatitis C virus and an amino acid sequence. Core protein: DNA sequence positions 1 to 573, E1 protein: positions 574 to 1149, E3 protein: positions 1150 to 2238, FLAG tag: positions 2239 to 2262.

FIG. 12-5 indicates the correspondence between a core-E1-E2 fused protein DNA sequence codon-optimized for hepatitis C virus and an amino acid sequence. Core protein: DNA sequence positions 1 to 573, E1 protein: positions 574 to 1149, E3 protein: positions 1150 to 2238, FLAG tag: positions 2239 to 2262.

FIG. 14-1 indicates the correspondence between an HA gene DNA sequence codon-optimized for avian influenza virus A/Shanghai/02/2013 and an amino acid sequence. The base sequence of a synthetic gene was designed based on the base sequence of the HA gene of avian influenza virus A/Shanghai/02/2013 (H7N9) in consideration of the introduction of a FLAG tag on the C terminal and optimization of the codon usage frequency of *Bombyx mori* cells. The amino acid sequence predicted from the base sequence of the synthetic gene is also shown.

FIG. 14-2 indicates the correspondence between an HA gene DNA sequence codon-optimized for avian influenza virus A/Shanghai/02/2013 and an amino acid sequence. The enclosed portion indicates the predicted mutation. The base sequence of a synthetic gene was designed based on the base sequence of the HA gene of avian influenza virus A/Shanghai/02/2013 (H7N9) in consideration of the introduction of a FLAG tag on the C terminal and optimization of the codon usage frequency of *Bombyx mori* cells. The amino acid sequence predicted from the base sequence of the synthetic gene is also shown.

FIG. 14-3 indicates the correspondence between an HA gene DNA sequence codon-optimized for avian influenza virus A/Shanghai/02/2013 and an amino acid sequence. The enclosed portion indicates the FLAG tag. The base sequence of a synthetic gene was designed based on the base sequence of the HA gene of avian influenza virus A/Shanghai/02/2013 (H7N9) in consideration of the introduction of a FLAG tag on the C terminal and optimization of the codon usage frequency of *Bombyx mori* cells. The amino acid sequence predicted from the base sequence of the synthetic gene is also shown.

FIG. 14-4 indicates the correspondence between an HA gene DNA sequence codon-optimized for avian influenza virus A/Shanghai/02/2013 and an amino acid sequence. The enclosed portion indicates the FLAG tag. The base sequence of a synthetic gene was designed based on the base sequence of the HA gene of avian influenza virus A/Shanghai/02/2013 (H7N9) in consideration of the introduction of a FLAG tag on the C terminal and optimization of the codon usage frequency of *Bombyx mori* cells. The amino acid sequence predicted from the base sequence of the synthetic gene is also shown.

FIG. 15 indicates confirmation of expression of HA protein from codon-optimized HA gene of avian influenza virus A/Shanghai/02/2013 produced using *Bombyx mori* by western blotting. Marker indicates molecular weight markers. Control indicates uninfected *Bombyx mori*. H7N9 indicates *Bombyx mori* infected with codon-optimized HA gene. The arrow indicates a specific band.

FIG. 16-1 indicates the correspondence between a Pre-M-M-E fused protein gene DNA sequence codon-optimized for Japanese encephalitis virus and an amino acid sequence. The enclosed portion indicates the FLAG tag. The base sequence of a synthetic gene was designed based on the base sequence of the Pre-M protein gene, M protein gene and E protein gene of Japanese encephalitis virus in consideration of the introduction of a FLAG tag on the C terminal and optimization of the codon usage frequency of *Bombyx mori* cells. The amino acid sequence predicted from the base sequence of the synthetic gene is also shown. PreM/M protein: DNA sequence positions 1 to 501, E protein: positions 502 to 2001, FLAG tag: positions 2002 to 2025.

FIG. 16-2 indicates the correspondence between a Pre-M-M-E fused protein gene DNA sequence codon-optimized for Japanese encephalitis virus and an amino acid sequence. The enclosed portion indicates the FLAG tag. The base sequence of a synthetic gene was designed based on the base sequence of the Pre-M protein gene, M protein gene and E protein gene of Japanese encephalitis virus in consideration of the introduction of a FLAG tag on the C terminal and optimization of the codon usage frequency of *Bombyx mori* cells. The amino acid sequence predicted from the base sequence of the synthetic gene is also shown. PreM/M protein: DNA sequence positions 1 to 501, E protein: positions 502 to 2001, FLAG tag: positions 2002 to 2025.

FIG. 16-3 indicates the correspondence between a Pre-M-M-E fused protein gene DNA sequence codon-optimized for Japanese encephalitis virus and an amino acid sequence. The enclosed portion indicates the FLAG tag. The base sequence of a synthetic gene was designed based on the base sequence of the Pre-M protein gene, M protein gene and E protein gene of Japanese encephalitis virus in consideration of the introduction of a FLAG tag on the C terminal and optimization of the codon usage frequency of *Bombyx mori* cells. The amino acid sequence predicted from the base sequence of the synthetic gene is also shown. PreM/M protein: DNA sequence positions 1 to 501, E protein: positions 502 to 2001, FLAG tag: positions 2002 to 2025.

FIG. 16-4 indicates the correspondence between a Pre-M-M-E fused protein gene DNA sequence codon-optimized for Japanese encephalitis virus and an amino acid sequence. The enclosed portion indicates the FLAG tag. The base sequence of a synthetic gene was designed based on the base sequence of the Pre-M protein gene, M protein gene and E protein gene of Japanese encephalitis virus in consideration of the introduction of a FLAG tag on the C terminal and optimization of the codon usage frequency of *Bombyx mori* cells. The amino acid sequence predicted from the base sequence of the synthetic gene is also shown. PreM/M protein: DNA sequence positions 1 to 501, E protein: positions 502 to 2001, FLAG tag: positions 2002 to 2025.

FIG. 18-1 indicates the correspondence between a G protein gene DNA sequence codon-optimized for rabies virus and an amino acid sequence. The enclosed portion indicates the FLAG tag. The base sequence of a synthetic gene was designed based on the base sequence of the G protein gene of rabies virus in consideration of the introduction of a FLAG tag on the C terminal and optimization of the codon usage frequency of *Bombyx mori* cells. The amino acid sequence predicted from the base sequence of the synthetic gene is also shown.

FIG. 18-2 indicates the correspondence between a G protein gene DNA sequence codon-optimized for rabies virus and an amino acid sequence. The enclosed portion indicates the FLAG tag. The base sequence of a synthetic gene was designed based on the base sequence of the G protein gene of rabies virus in consideration of the introduction of a FLAG tag on the C terminal and optimization of the codon usage frequency of *Bombyx mori* cells. The amino acid sequence predicted from the base sequence of the synthetic gene is also shown.

FIG. 18-3 indicates the correspondence between a G protein gene DNA sequence codon-optimized for rabies virus and an amino acid sequence. The enclosed portion indicates the FLAG tag. The base sequence of a synthetic gene was designed based on the base sequence of the G protein gene of rabies virus in consideration of the introduction of a FLAG tag on the C terminal and optimization of the codon usage frequency of *Bombyx mori* cells. The amino acid sequence predicted from the base sequence of the synthetic gene is also shown.

FIG. 18-4 indicates the correspondence between a G protein gene DNA sequence codon-optimized for rabies virus and an amino acid sequence. The enclosed portion indicates the FLAG tag. The base sequence of a synthetic gene was designed based on the base sequence of the G protein gene of rabies virus in consideration of the introduction of a FLAG tag on the C terminal and optimization of the codon usage frequency of *Bombyx mori* cells. The amino acid sequence predicted from the base sequence of the synthetic gene is also shown.

FIG. 19-1 indicates the correspondence between a Pre-M-M-E fused protein gene DNA sequence codon-optimized for West Nile virus and an amino acid sequence. The base sequence of a synthetic gene was designed based on the base sequence of the E protein gene of West Nile virus in consideration of the introduction of a FLAG tag on the C terminal and optimization of the codon usage frequency of *Bombyx mori* cells. The amino acid sequence predicted from the base sequence of the synthetic gene is also shown.

FIG. 19-2 indicates the correspondence between a Pre-M-M-E fused protein gene DNA sequence codon-optimized for West Nile virus and an amino acid sequence. The base sequence of a synthetic gene was designed based on the base sequence of the E protein gene of West Nile virus in consideration of the introduction of a FLAG tag on the C terminal and optimization of the codon usage frequency of

*Bombyx mori* cells. The amino acid sequence predicted from the base sequence of the synthetic gene is also shown.

FIG. 19-3 indicates the correspondence between a Pre-M-M-E fused protein gene DNA sequence codon-optimized for West Nile virus and an amino acid sequence. The base sequence of a synthetic gene was designed based on the base sequence of the E protein gene of West Nile virus in consideration of the introduction of a FLAG tag on the C terminal and optimization of the codon usage frequency of *Bombyx mori* cells. The amino acid sequence predicted from the base sequence of the synthetic gene is also shown.

FIG. 20-1 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

FIG. 20-2 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

FIG. 20-3 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

Figure 4:
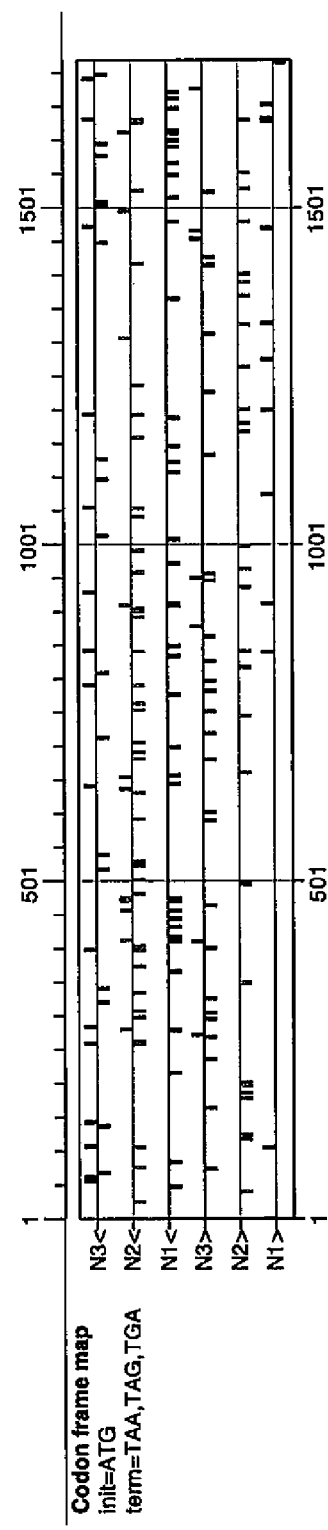

FIG. 20-4 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

FIG. 20-5 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

FIG. 20-6 indicates the correspondence between a spike glycoprotein (S protein) gene DNA sequence codon-optimized for MERS coronavirus and an amino acid sequence. The base sequence of a synthetic gene was designed based on the base sequence of the S protein gene of MERS coronavirus in consideration of the introduction of a FLAG tag on the C terminal and optimization of the codon usage frequency of *Bombyx mori* cells. The amino acid sequence predicted from the base sequence of the synthetic gene is also shown.

FIG. 21-1 indicates the correspondence between a VP4-VP2-VP3-VP1-2A-3C fused protein gene DNA sequence codon-optimized for foot and mouth disease virus and an amino acid sequence. The base sequence of a synthetic gene was designed based on the base sequence of VP4, VP2, VP3, VP1, 2A and 3C protein genes of foot and mouth disease virus in consideration of the introduction of a FLAG tag on the N terminal and optimization of the codon usage frequency of *Bombyx mori* cells. The amino acid sequence predicted from the base sequence of the synthetic gene is also shown.

FIG. 21-2 indicates the correspondence between a VP4-VP2-VP3-VP1-2A-3C fused protein gene DNA sequence codon-optimized for foot and mouth disease virus and an amino acid sequence. The base sequence of a synthetic gene was designed based on the base sequence of VP4, VP2, VP3, VP1, 2A and 3C protein genes of foot and mouth disease virus in consideration of the introduction of a FLAG tag on the N terminal and optimization of the codon usage frequency of *Bombyx mori* cells. The amino acid sequence predicted from the base sequence of the synthetic gene is also shown.

FIG. 21-3 indicates the correspondence between a VP4-VP2-VP3-VP1-2A-3C fused protein gene DNA sequence codon-optimized for foot and mouth disease virus and an amino acid sequence. The base sequence of a synthetic gene was designed based on the base sequence of VP4, VP2, VP3, VP1, 2A and 3C protein genes of foot and mouth disease virus in consideration of the introduction of a FLAG tag on the N terminal and optimization of the codon usage frequency of *Bombyx mori* cells. The amino acid sequence predicted from the base sequence of the synthetic gene is also shown.

FIG. 21-4 indicates the correspondence between a VP4-VP2-VP3-VP1-2A-3C fused protein gene DNA sequence codon-optimized for foot and mouth disease virus and an amino acid sequence. The base sequence of a synthetic gene was designed based on the base sequence of VP4, VP2, VP3, VP1, 2A and 3C protein genes of foot and mouth disease virus in consideration of the introduction of a FLAG tag on the N terminal and optimization of the codon usage frequency of *Bombyx mori* cells. The amino acid sequence predicted from the base sequence of the synthetic gene is also shown.

FIG. 21-5 indicates the correspondence between a VP4-VP2-VP3-VP1-2A-3C fused protein gene DNA sequence codon-optimized for foot and mouth disease virus and an amino acid sequence. The base sequence of a synthetic gene was designed based on the base sequence of VP4, VP2, VP3, VP1, 2A and 3C protein genes of foot and mouth disease virus in consideration of the introduction of a FLAG tag on the N terminal and optimization of the codon usage frequency of *Bombyx mori* cells. The amino acid sequence predicted from the base sequence of the synthetic gene is also shown.

BEST MODE FOR CARRYING OUT THE INVENTION

The nucleic acid according to the present invention contains a nucleic acid sequence of a virus that has been subjected to codon optimization for expression in *Bombyx mori* cells. More specifically, codon optimization consists of replacing a target nucleic acid sequence using a correspondence table (FIG. 2) of amino acid sequences and gene sequences prepared based on the codon usage (FIG. 1) of *Bombyx mori*. In this correspondence table, the sequences are designed so as to generate numerous UGA (stop codons) in the complementary strand by using UCA (having the highest usage frequency in *Bombyx mori*) for the Ser sequence to prevent the synthesis of unexpected by-products as a result of being able to form a long coding frame in the complementary strand.

Although there are no particular limitations on the virus targeted by the vaccine according to the present invention, examples thereof include influenza virus, hepatitis C virus, Japanese encephalitis virus, rabies virus, West Nile virus, MERS coronavirus and foot and mouth disease virus. Among influenza viruses, type A influenza virus is preferable, and subtypes H5 and H7 are more preferable. Among hepatitis C viruses, genotype 1*a* 1*b*, 2*a*, 2*b* or 3*a* is preferable.

The virus nucleic acid sequence according to the present invention encodes any arbitrary virus protein provided it can function as a vaccine. In the case of influenza virus, the virus nucleic acid sequence preferably encodes HA protein. In the case of hepatitis C virus, the virus nucleic acid protein preferably encodes core protein, E1 protein, E2 protein or a combination thereof. In the case of Japanese encephalitis virus, the virus nucleic acid sequence preferably encodes PreM protein, M protein and/or E protein. In the case of rabies virus, the virus nucleic acid sequence preferably encodes G protein. In the case of West Nile virus, the virus nucleic acid sequence preferably encodes PreM protein, M protein and/or E protein. In the case of MERS coronavirus, the virus nucleic acid sequence preferably encodes spike glycoprotein (S protein). In the case of foot and mouth disease virus, the virus nucleic acid sequence preferably encodes VP4, VP2, VP3, VP1, 2A and/or 3C protein.

The virus nucleic acid sequence according to the present invention may have been modified to attenuate the influenza virus HA protein. Attenuation can be carried out by an arbitrary modification commonly known among persons with ordinary skill in the art. For example, in the case of the HA protein of influenza virus, the sequence at the cleavage site that binds the HA1 and HA2 molecules that govern pathogenicity is modified. In one mode thereof, the amino acid sequence indicated in SEQ ID NO: 7 in HA protein is replaced with the amino acid sequence indicated in SEQ ID NO: 8.

Thus, the nucleic acid according to the present invention is preferably a nucleic acid that contains or is composed of the nucleic acid sequence of SEQ ID NO: 4, 12, 15, 18, 21, 24, 27, 30 or 33.

In the present invention, a vaccine is produced in *Bombyx mori*. The method used to produce a vaccine using *Bombyx mori* can be carried out using any arbitrary method commonly known among persons with ordinary skill in the art. More specifically, the nucleic acid of the present invention is introduced into *Bombyx mori* and a virus protein encoded by the virus nucleic acid sequence is expressed therein. Although there are no particular limitations thereon, the method used to introduce the nucleic acid is carried out by, for example, inoculating *Bombyx mori* with a recombinant baculovirus comprising the nucleic acid of the present invention.

Thus, in one embodiment, the present invention is the vector that contains the nucleic acid according to the present invention. The vector of the present invention is an arbitrary vector that enables expression of a protein encoded by the nucleic acid. The vector of the present invention may also be introduced directly into *Bombyx mori*. The vector of the present invention is preferably a baculovirus transfer vector.

In addition, in one embodiment, the present invention is a recombinant baculovirus that is produced using the aforementioned vector according to the present invention. The method used to produce the recombinant baculovirus can be carried out using any arbitrary method commonly known among persons with ordinary skill in the art. In one embodiment, the recombinant baculovirus of the present invention can be produced by simultaneously introducing the vector of the present invention and DNA extracted from baculovirus into *Bombyx mori* cells.

Thus, in one embodiment, the present invention is *Bombyx mori* comprising the nucleic acid, the vector or the recombinant baculovirus according to the present invention. There are no particular limitations on the form in which the vector or recombinant baculovirus is contained, and the vector or recombinant baculovirus may be present independently from the genome of *Bombyx mori* or may be incorporated in the genome of *Bombyx mori*.

In one embodiment, the present invention is a polypeptide composed of an amino acid sequence encoded by the nucleic acid according to the present invention.

In one embodiment, the present invention is a method for producing a vaccine that uses the nucleic acid, the vector, the recombinant baculovirus or the *Bombyx mori* according to the present invention.

In one embodiment, the method for producing a vaccine according to the present invention comprises the following steps:

1) a step for obtaining the nucleic acid or vector according to the present invention, 2) a step for introducing the nucleic acid, vector or recombinant baculovirus according to the present invention into *Bombyx mori*, and 3) a step for recovering protein from *Bombyx mori*.

Introduction of the nucleic acid, vector or recombinant baculovirus of the present invention into *Bombyx mori* can be carried out using an arbitrary method commonly known among persons with ordinary skill in the art. Introduction is preferably carried out using baculovirus. There are no particular limitations on the time at which the nucleic acid, vector or recombinant baculovirus is introduced into *Bombyx mori*. The time of introduction is preferably the pupal stage.

Recovery of protein from *Bombyx mori* can use an arbitrary method commonly known among persons with ordinary skill in the art. For example, in the case of HA protein, after homogenizing *Bombyx mori* in an isotonic buffer solution, HA protein is recovered using immobilized erythrocytes or a sialic acid column (fetuin column).

In one embodiment, the present invention is a vaccine that contains the polypeptide according to the present invention or is produced according to the production method of the present invention for vaccinating an animal against a viral infection.

Figure 9:
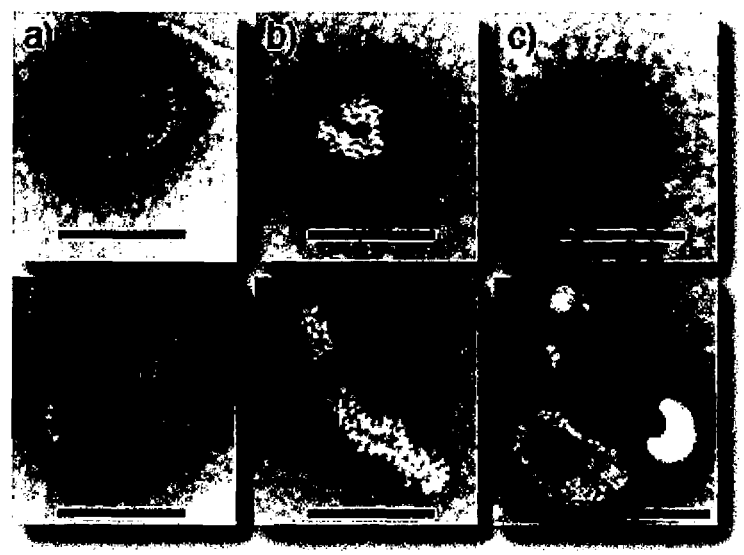
FIG. 9 indicates electron micrographs of sucrose density gradient fractions. A large number of virus-like particles having a diameter of 60 nm to 120 nm were observed.

In one embodiment, the vaccine of the present invention has a virus-like particle structure. A virus-like particle structure refers to a structure in which well-defined HA spikes are densely arranged on the surface of particles having a diameter of 50 nm to 150 nm, and although morphologically resembling virus particles, are naturally non-pathogenic. The virus-like particle structure is preferably a spherical structure that has spikes. The particle diameter of the virus-like particles is preferably 60 nm to 120 nm. An example of the virus-like particle structure of the present invention is shown in FIG. 9.

In one embodiment, the present invention is a method for inoculating an animal with a vaccine against a viral infection, comprising administering to the animal an effective amount of a vaccine comprising the polypeptide according to the present invention or a vaccine that is produced according to the production method according to the present invention.

In one embodiment, the present invention is a method for introducing an immune response to a virus in an animal, comprising administering to the animal an effective amount of a vaccine comprising the polypeptide according to the present invention or a vaccine that is produced according to the production method according to the present invention.

The animal according to the present invention refers to an animal capable of acquiring sufficient humoral immunity or cellular immunity to a virus as a result of being inoculated with a vaccine. The animal according to the present invention is preferably a vertebrate, more preferably a human, bird, pig or horse, and most preferably a human.

An effective amount of vaccine refers to an amount that is sufficient for achieving a biological effect such as inducing sufficient humoral immunity or cellular immunity to a virus. In addition, the administration method includes inhalation, intranasal administration, oral administration and parenteral administration (such as intracutaneous, intramuscular, intravenous, intraperitoneal or subcutaneous administration). The effective amount and administration method are dependent on the age, gender, physical status and body weight of the person undergoing administration. For example, in the case of an influenza vaccine, a vaccine comprising 15 μg or more of HA protein per strain in 1 ml is typically injected twice subcutaneously at an interval of about 2 to 4 weeks in an amount of 0.25 ml to subjects age 6 months to under 3 years old or in an amount of 0.5 ml to subjects age 3 to under 13 years old. Subjects age 13 years and older are injected subcutaneously once or twice at an interval of about 2 to 4 weeks in an amount of 0.5 ml.

EXAMPLES

The following provides a more detailed explanation of the present invention by indicating specific examples thereof.

Example 1

Design of DNA for Developing Influenza Vaccine Suitable for Production in *Bombyx mori* Based on HA Genetic Information of Avian Influenza Virus a Virus/Tufted Duck/Fukushima/16/2011 (H5N1)

Design of Nucleic Acid Sequence of Codon-Optimized HA Gene

HA genetic information of highly pathogenic influenza virus A/tufted duck/Fukushima/16/2011 (H5N1) which was found in wild ducks in 2011 was designed and altered in the manner indicated below.

First, the amino acid sequence (SEQ ID NO: 2) of the hemagglutinin (HA) protein of avian influenza virus A/tufted duck/Fukushima/16/2011 (H5N1) was predicted from the gene sequence (SEQ ID NO: 1) registered with Genbank under Accession No. BAK24078.

Next, the sequence Arg-Glu-Arg-Arg-Lys-Arg (SEQ ID NO: 7) in the predicted amino acid sequence, which is presumed to be associated with high pathogenicity, was replaced with the sequence Arg-Glu-Thr-Arg (SEQ ID NO: 8), and a FLAG tag sequence composed of Asp-Tyr-Lys-Asp-Asp-Asp-Asp-Lys (SEQ ID NO: 5) was added to the C-terminal to design an attenuated HA protein amino acid sequence (SEQ ID NO: 3).

Codon optimization was carried out for the purpose of improving protein expression using *Bombyx mori*. A correspondence table between the resulting amino acid sequence and gene sequence (FIG. 2) was prepared based on the codon usage of *Bombyx mori* obtained from the Codon Usage Database provided by the Kazusa DNA Research Instituted (FIG. 1). In this correspondence table, the sequences are designed so as to generate numerous UGA (stop codons) in the complementary strand by using UCA (having the highest usage frequency in *Bombyx mori*) for the Ser sequence to prevent the synthesis of unexpected by-products as a result of being able to form a long coding frame in the complementary strand. The designed gene sequence (SEQ ID NO: 4) and the corresponding amino acid sequence are shown in FIG. 3. Large coding frames other than the protein desired to be expressed were confirmed to be unable to be formed (FIG. 4).

Synthesis of Codon-Optimized HA Gene and Vector Construction

Total synthesis of DNA was commissioned to Takara Bio Inc. based on sequence data of the codon-optimized HA gene designed as described above. The synthesized codon-optimized HA gene DNA was inserted into a transfer vector in the form of pBm-8 (Baculotechnologies Co., Ltd.) using an in-fusion method (Clontech Laboratories Inc.) to prepare pBm-8HA.

Infection of *Bombyx mori* with Baculovirus Introduced with Codon-Optimized HA Gene and Preparation of Emulsion Recombinant baculovirus for producing a vaccine in a cell supernatant was obtained by simultaneously introducing pBm-8HA and DNA extracted from baculovirus into *Bombyx mori* cells. Pupas of *Bombyx mori* were inoculated with the recombinant baculovirus. Namely, a virus stock solution having a virus titer of $1 \times 10^8$ pfu/ml or more was diluted ten-fold with insect cell medium TC-100. Pupas of *Bombyx mori* were then inoculated with 50 μl of this diluted solution by injecting into the abdominal region on the second day of molting followed by breeding the pupas in an incubator at 26° C. 72 hours later, the pupas were cut in half with a scissors on ice and the mesenteron was removed with a forceps followed by homogenizing and emulsifying in phenylthiourea-containing PBS using a Potter-Elvehjem homogenizer. PBS was added to the emulsion to a volume of 50 ml followed by the addition of 5 μl of formalin to a final concentration of 0.01% to obtain an emulsion of *Bombyx mori* pupas.

Recovery of HA Protein and Confirmation of Expression

The resulting emulsion of *Bombyx mori* pupas was subjected to ultrasonic treatment for 5 minutes with a sonicator (UR-20P, Tomy Seiko Co., Ltd.) followed by the addition of immobilized chicken erythrocytes to recover HA protein. Moreover, the HA protein was able to be purified to 95% or more at the protein level by purifying by DEAE ion exchange chromatography. Expression of the purified protein was confirmed by western blotting (primary antibody: anti-FLAG mouse monoclonal antibody, secondary antibody: anti-mouse IgG rabbit polyclonal antibody). A band was confirmed in the vicinity of 65 kDa as shown in FIG. 6.

Evaluation of HA Activity

Influenza virus has the property of agglutinating when mixed with erythrocytes of various animals, which is referred to as hemagglutination, and is the result of formation of a large aggregate by crosslinking of a plurality of erythrocytes through the bonding of hemagglutinin (HA) present on the virus surface with sugar chains of erythrocytes. Since the concentration of virus (HA activity) contained in a stock solution can be calculated by investigating the degree of agglutination when the virus is serially diluted by using this property, this can be used to quantify influenza virus. More specifically, after serially diluting 50 µl of a specimen with 50 µl of PBS (phosphate-buffered saline) using a 96-well microplate, an equal volume of chicken erythrocytes adjusted to a concentration of 0.5% was added and mixed well followed by allowing to stand undisturbed for 30 minutes to 60 minutes at room temperature. Although HA forms an aggregate with the erythrocytes if HA activity is present in the specimen, in the case the virus is absent, an aggregate is not formed and the erythrocytes settle on the bottom of the plate in the form of a red dot. HA titer is represented in the form of HA agglutination activity based on the dilution factor of the dilution prior to the formation of this red dot.

Results of Evaluation

The resulting HA protein solution was evaluated under the aforementioned conditions. As a result, HA activity was demonstrated to be 2,097,152. As a result, total activity produced in 30 Bombyx mori pupas was 2,097,152×50 ml=104,857,600, and the amount of HA activity per pupa was 3,495,253. This value of HA activity per recombinant Bombyx mori individual is roughly 11.4 times of HA activity of 307,160 per Bombyx mori individual when HA gene of human-derived highly pathogenic avian influenza virus A/HK/483/97 (H5N1) was expressed in Bombyx mori in 1998, and is roughly 340 times of HA activity of 10,240 produced from a single embryonated chicken egg, thereby demonstrating a remarkable increase in the amount of HA activity.

Immunization of Chickens with HA Protein Solution

Chickens were immunized using the aforementioned HA protein solution. Chickens were inoculated with 0.5 ml of HA protein solution adjusted to an HA activity value between 4,096 and 8,192 into leg muscle on two occasions at an interval of 16 days. Blood samples of 5 ml each were collected from the chickens at 33 days, 40 days, 47 days and 50 days after the initial inoculation.

Evaluation of HI Activity of Antibody Produced by Immunized Chickens

The aforementioned chicken blood samples were each allowed to stand at room temperature followed by centrifuging at room temperature to obtain chicken serum. The hemagglutination inhibitory activity (HI activity) of each sample of chicken serum was examined using the method indicated below. First, a 1:2 serial dilution series of the serum was prepared that contained 25 µl per well using a 96-well plate. Next, 25 µl of the aforementioned HA protein (adjusted to 8 HA with PBS) were added to each well. After allowing the plate to stand undisturbed for 30 minutes at room temperature, 50 µl of chicken erythrocytes at a concentration of 0.5% in PBS were added to each well. One hour later, the hemagglutination pattern was observed and the largest dilution factor at which agglutination of erythrocytes was observed was taken to be the HI activity value. Serum at 33 days after initial inoculation demonstrated HI activity of 8,192.

Evaluation of HI Activity for Various Influenza Viruses

In addition, the presence or absence of HI activity was examined for various influenza viruses using chicken serum obtained at 40 days after initial inoculation. HI activity was measured under the same conditions as previously described using each of the viruses of A/chicken/Legok/2004 (H5N1) and A/chicken/West Java/2009 (H5N1). The results are shown in FIG. 7. The chicken serum demonstrated HI activity against all viruses.

Fractionation of HA Protein Solution by Sucrose Density Gradient

In addition, the HA protein solution was fractionated using the sucrose density gradient method. The HA activity of each liquid fraction was examined using the same method as previously described. The results are shown in FIG. 8. Fraction 4, having a buoyant density of naturally-occurring virus of 1.18 g/l, did not show HA activity. On the other hand, HA activity was observed in fractions 7 to 9 demonstrating smaller buoyant densities.

Observation of HA Protein Solution Fraction with an Electron Microscope

Fraction 7 of the aforementioned sucrose density gradient was observed with an electron microscope. The results are shown in FIG. 9. A virus particle-like structure in the shape of a sphere having spikes and having a particle diameter of 60 nm to 120 nm was observed. As a general rule, naturally-occurring viruses have a spherical shape of 60 nm to 150 nm, a long, narrow fibrous shape of 100 nm to 1000 nm or an annular shape of 80 nm to 200 nm. In contrast, as shown in FIG. 10, the HA protein derived from Bombyx mori exhibited a diverse shape in the manner of naturally-occurring viruses, and the shape was determined for the first time in this research to have a spherical shape of 60 nm to 150 nm, a fibrous shape of about 200 nm and an annular shape of about 60 nm to 150 nm. These morphological characteristics are thought to be reflected in the aforementioned previously unobserved strong immunity of HA protein.

In this manner, the reason for the activity level of HA protein of avian influenza virus A/tufted duck/Fukushima/16/2001 being high in pupas of Bombyx mori is thought to be due to modification of the design of DNA based on genetic information and the effectiveness of genetic manipulation of synthetic DNA on the basis thereof. Moreover, since the target gene was highly expressed using the pupal stage of Bombyx mori, the resulting vaccine is through to have shown a virus particle-like structure. In this manner, it is thought that this novel method for producing a vaccine that utilizes design modification and synthesis of DNA based on genetic information will be used in numerous fields in the future.

In conclusion, the greatest significance of vaccine production utilizing Bombyx mori by design-modified DNA is that an amount of vaccine equivalent to 340 embryonated chicken eggs can be produced with a single Bombyx mori pupa.

Example 2

Design of DNA for Developing Influenza Vaccine Suitable for Production in Bombyx mori Based on HA Genetic Information of Avian Influenza Virus a Virus/Chicken/Sukabumi/2008 (H5N1)

Since viruses frequently mutate over time in both humans and animals, apprehension remains with respect to only using DNA of the avian influenza virus A/tufted duck/Fukushima/16/2011 strain. Therefore, DNA for developing a vaccine for influenza virus (SEQ ID NO: 12) was designed in the same manner as Example 1 based on amino acid sequence data (SEQ ID NO: 10) predicted from the HA gene sequence of influenza virus A/chicken/Sukabumi/2008

(H5N1) (SEQ ID NO: 9) isolated in Indonesia in 2008. The corresponding amino acid sequence (SEQ ID NO: 11) is shown in FIG. 10. In the same manner as Example 1, a recombinant baculovirus comprising the aforementioned DNA for development was inoculated into *Bombyx mori* followed by synthesis and recovery of HA protein and confirmation of the expression thereof by western blotting (FIG. 11). Evaluation of HA activity yielded an amount of HA activity per pupa of 419,430.

Example 3

Design of DNA for Developing Hepatitis C Virus Vaccine Suitable for Production in *Bombyx mori*

The particle structure of hepatitis C virus is such that it is covered with a lipid layer comprising E1 and E2 glycoproteins, with the virus gene being contained within the particle with a nuclear protein or a protein referred to as the core protein. It has been clearly determined that the E1 protein and E2 protein play an important role in order for the virus to initiate infection, while conversely, the E1 protein and E2 protein are also protective antigens against infection, and therefore have an important function as vaccine proteins as well. In actuality, E1 protein and E2 protein have been used to prepare a test vaccine, and that vaccine has been reported to demonstrate preventive effects as well as mild, albeit inadequate, protective effects in chimpanzees. However, more highly concentrated E1 protein and E2 protein are required in order to demonstrate more adequate preventive effects.

Design of Nucleic Acid Sequence of Codon-Optimized Core-E1-E2-Fused Protein Gene Therefore, the inventors of the present invention designed genetic information for expressing a fused protein consisting of hepatitis C virus-like core protein, E1 protein and E2 protein in order to develop a hepatitis C virus vaccine. Here, a fused protein was designed since a virus particle-like protein can be expected to be synthesized by expressing simultaneously. First, a FLAG tag sequence (SEQ ID NO: 5) was added to the amino acid sequence from the core protein to E1 protein and E2 protein (SEQ ID NO: 13) in the amino acid sequence of HCV gene registered with Genbank under Accession No. ACK28185 to obtain an amino acid sequence of a fused protein based on the nucleic acid design (SEQ ID NO: 14). The nucleic acid sequence of a codon-optimized Core-E1-E2 fused protein was then designed in the same manner as Example 1 based on the amino acid sequence of this fused protein (SEQ ID NO: 15). Correspondence between the designed nucleic acid sequence of the chimeric synthetic DNA and the amino acid sequence is shown in FIG. 12.

DNA Synthesis of Codon-Optimized Core-E1-E2 Fused Protein Gene and Vector Construction Full-length gene DNA was synthesized in the same manner as Example 1 based on the designed nucleic acid sequence of the codon-optimized core-E1-E2 fused protein gene followed by insertion into pBm-8 vector to produce pBM-8Core-E1-E2.

Infection with Baculovirus Introduced with Codon-Optimized Core-E1-E2 Fused Protein Gene A recombinant baculovirus was obtained in the same manner as Example 1 using pBm-8Core-E1-E2 followed by inoculation of *Bombyx mori* pupas to obtain an emulsion of *Bombyx mori* pupas.

Recovery of Core-E1-E2 Fused Protein and Confirmation of Expression Thereof

Figure 13:
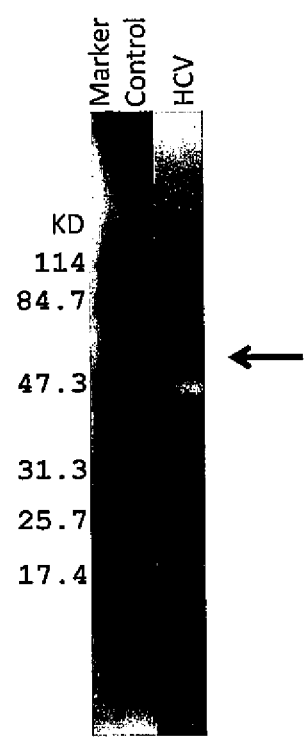
FIG. 13 indicates confirmation of expression of core-E1-E2 fused protein from codon-optimized core-E1-E2 fused protein gene of hepatitis C virus produced using *Bombyx mori* by western blotting. Marker indicates molecular weight markers. Control indicates uninfected *Bombyx mori*. HCV indicates *Bombyx mori* infected with codon-optimized core-E1-E2 fused protein gene. The arrow indicates a specific band. This indicates confirmation of expression of core-E1-E2 fused protein produced using *Bombyx mori* by western blotting.

The resulting emulsion of *Bombyx mori* pupas was subjected to ultrasonic treatment for 5 minutes with a sonicator (UR-20P, Tomy Seiko Co., Ltd.) followed by purifying the Core-E1-E2 fused protein using the sucrose density gradient method (sucrose concentration: 10% to 50%, 100,000 G, 24 hours). Expression of the purified Core-E1-E2 fused protein was confirmed by western blotting in the same manner as Example 1. As shown in FIG. 13, a band was confirmed in the vicinity of 60 kDa.

Evaluation of Activity

Immune reaction can be predicted from the amount of protein produced, and the effect in a neutralization test was estimated using antibody produced as a result thereof.

Discussion of Results

Since a molecular weight of 83 kDa or more is predicted to be demonstrated as a result of linked expression of Core-E1-E2 fused protein, a molecular size of 60 kDa was suggested to indicate that the Core-E1-E2 protein was subjected to intracellular processing by protease resulting in synthesis of mature E2. This fact clearly indicates that the vaccine protein designed based on DNA was accurately produced without any significant difference in molecular size, and judging from the strong protein band as well, hepatitis C vaccine was suggested to be efficiently synthesized.

Reference Example 1

Design of DNA for Developing Influenza Vaccine Suitable for Production in *Bombyx mori* Based on HA Genetic Information of Avian Influenza Virus a Virus/Shanghai/2/2013 (H7N9)

DNA for developing a vaccine for influenza virus (SEQ ID NO: 18) was designed in the same manner as Example 1 based on amino acid sequence data (SEQ ID NO: 16) of the HA gene sequence of avian influenza virus A/Shanghai/2/2013 (H7N9) registered with GISAID under Accession No. EPI1439502 that was isolated in China in 2013. The corresponding amino acid sequence (SEQ ID NO: 17) is shown in FIG. 14. Since the 199th Glu of HA protein is predicted to mutate to Asp and the 234th Gly is predicted to mutate to Asp when influenza caused by H7N9 influenza virus becomes epidemic in humans, those mutations were introduced. A recombinant baculovirus comprising the aforementioned DNA for development was inoculated into *Bombyx mori* pupas followed by synthesis and recovery of HA protein in the same manner as Example 1 (FIG. 15). The HA activity thereof was then evaluated in the same manner as Example 1.

Reference Example 2

Design of DNA for Developing Japanese Encephalitis Virus Vaccine Suitable for Production in *Bombyx mori*

Japanese encephalitis virus is an encephalitis virus that is mainly transmitted by *Culex triaeniorhynchus*, and is currently prevalent in the regions of Southeast Asia, India and China. Although mouse brain infected with the same virus has been used as a vaccine for its prevention, viruses for vaccine use have more recently come to be cultured in cultured cells. However, there is the need to develop a new vaccine in response to demands for enhanced vaccine immunity, reduction of adverse side effects and lower production costs, and considerable expectations are being placed on improvement of vaccine quality.

Design of Nucleic Acid Sequence of PreM-M-E Fused Protein Gene Codon-Optimized for Japanese Encephalitis Virus Therefore, the inventors of the present invention designed genetic information for expressing the E protein of Japanese encephalitis virus in order to develop a vaccine against Japanese encephalitis virus. First, a FLAG tag sequence (SEQ ID NO: 5) was added to the amino acid sequence from the PreM protein to the M protein and E protein (SEQ ID NO: 19) in the amino acid sequence registered with Genbank under Accession No. ABQ52691 to obtain an amino acid sequence of the Japanese encephalitis virus PreM-M-E fused protein based on the nucleic acid design (SEQ ID NO: 20). The nucleic acid sequence of a PreM-M-E fused protein codon-optimized for Japanese encephalitis virus was then designed in the same manner as Example 1 based on the amino acid sequence of this Japanese encephalitis virus PreM-M-E fused protein (SEQ ID NO: 21). Correspondence between the designed nucleic acid sequence of the chimeric synthetic DNA and the amino acid sequence is shown in FIG. 16.

DNA Synthesis of PreM-M-E Fused Protein Gene Codon-Optimized for Japanese Encephalitis Virus and Vector Construction Full-length gene DNA was synthesized in the same manner as Example 1 based on the designed nucleic acid sequence of the PreM-M-E fused protein gene codon-optimized for Japanese encephalitis virus followed by insertion into pBm-8 vector to produce pBM-8JevpMME.

Infection with Baculovirus Introduced with PreM-M-E Fused Protein Gene Codon-Optimized for Japanese Encephalitis Virus A recombinant baculovirus was obtained in the same manner as Example 1 using pBm-8JevpMME followed by inoculation of *Bombyx mori* pupas to obtain an emulsion of *Bombyx mori* pupas.

Figure 17:
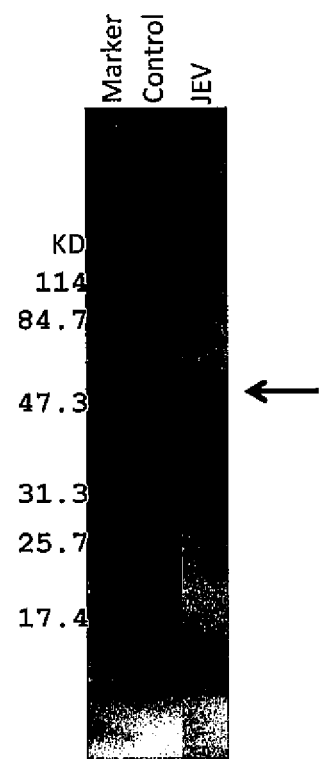
FIG. 17 indicates confirmation of expression of PreM-M-E fused protein from codon-optimized PreM-M-E fused protein gene of Japanese encephalitis virus produced using *Bombyx mori* by western blotting. Marker indicates molecular weight markers. Control indicates uninfected *Bombyx mori*. JEV indicates *Bombyx mori* infected with codon-optimized PreM-M-E fused protein gene. The arrow indicates a specific band.

Recovery of Japanese Encephalitis Virus PreM-M-E Fused Protein and Confirmation of Expression The resulting emulsion of *Bombyx mori* pupas was subjected to ultrasonic treatment and purification in the same manner as Example 3. Expression of the purified Japanese encephalitis virus E protein was confirmed by western blotting in the same manner as Example 3 (FIG. 17).

Evaluation of Activity

Immune reaction can be predicted from the amount of protein produced, and the effect in a neutralization test was estimated using antibody produced as a result thereof.

Reference Example 3

Design of DNA for Developing Rabies Virus Vaccine Suitable for Production in *Bombyx mori*

Although rabies virus is distributed on a global scale and results in numerous deaths, resulting in the international need for the development of an effective, safe and inexpensive vaccine, the development of such a vaccine is proceeding slowly. Therefore, if it were possible to develop a vaccine that is safe, inexpensive and demonstrates potent immunity, the demand for such a vaccine is thought to be on a global scale. Vaccines currently in use are derived from rabbit, goat and mouse brain, while human diploid cells and chicken embryonic cells are also used. In the future, it will be desirable to develop a component vaccine that can be used stably both in terms of supply and costs, and the successful development of a component vaccine using *Bombyx mori* is thought to result in use of that vaccine on a global scale.

Design of Nucleic Acid Sequence of G Protein Gene Codon-Optimized for Rabies Virus Therefore, the inventors of the present invention designed genetic information for expressing the G protein of rabies virus in order to develop a vaccine against rabies virus. First, a FLAG tag sequence (SEQ ID NO: 5) was added to the amino acid sequence registered with Genbank under Accession No. ABX46657 (SEQ ID NO: 22) to obtain an amino acid sequence of the rabies virus G protein based on the nucleic acid design (SEQ ID NO: 23). The nucleic acid sequence of a G protein codon-optimized for rabies virus was then designed in the same manner as Example 1 based on the amino acid sequence of this rabies virus G protein (SEQ ID NO: 24). Correspondence between the designed nucleic acid sequence of the chimeric synthetic DNA and the amino acid sequence is shown in FIG. 18.

DNA Synthesis of G Protein Gene Codon-Optimized for Rabies Virus and Vector Construction Full-length gene DNA was synthesized in the same manner as Example 1 based on the designed nucleic acid sequence of the G protein gene codon-optimized for rabies virus followed by insertion into pBm-8 vector to produce pBM-8rvG.

Infection with Baculovirus Introduced with G Protein Gene Codon-Optimized for Rabies Virus A recombinant baculovirus was obtained in the same manner as Example 1 using pBm-8rvG followed by inoculation of *Bombyx mori* pupas to obtain an emulsion of *Bombyx mori* pupas.

Recovery of Rabies Virus G Protein and Confirmation of Expression

The resulting emulsion of *Bombyx mori* pupas was subjected to ultrasonic treatment and purification in the same manner as Example 3. Expression of the purified rabies virus G protein was confirmed by western blotting in the same manner as Example 3.

Evaluation of Activity

Immune reaction can be predicted from the amount of protein produced, and the effect in a neutralization test was estimated using antibody produced as a result thereof.

Reference Example 4

Design of DNA for Developing West Nile Virus Vaccine Suitable for Production in *Bombyx mori*

West Nile virus is prevalent in the US, Eastern Europe and Europe, and there is the risk of its propagation to Japan in the near future. In addition to its ecocycle from mosquitoes to chickens and back to mosquitoes, this cycle also includes propagation to humans or horses. Although there are currently no vaccines available, there is an urgent global demand for the development of a vaccine. Although vaccine research and development is being actively conducted in the US and Europe, those efforts have yet to be successful. Therefore, the inexpensive, large-scale production of a vaccine against West Nile fever would enable its use on a global scale.

Design of Nucleic Acid Sequence of PreM-M-E Fused Protein Gene Codon-Optimized for West Nile Virus Therefore, the inventors of the present invention designed genetic information for expressing the PreM-M-E fused protein of West Nile virus in order to develop a vaccine against West Nile virus. First, a FLAG tag sequence (SEQ ID NO: 5) was added to the amino acid sequence from the PreM protein to the M protein and E protein (SEQ ID NO: 25) in the amino acid sequence registered with Genbank under Accession No. AAT95390 to obtain an amino acid sequence of the West Nile virus PreM-M-E fused protein based on the nucleic acid design (SEQ ID NO: 26). The nucleic acid sequence of a PreM-M-E fused protein codon-optimized for West Nile virus was then designed in the same manner as Example 1 based on the amino acid sequence of this West Nile virus PreM-M-E fused protein (SEQ ID NO: 27). Correspondence between the designed nucleic acid sequence of the chimeric synthetic DNA and the amino acid sequence is shown in FIG. 19.

DNA Synthesis of PreM-M-E Fused Protein Gene Codon-Optimized for West Nile Virus and Vector Construction Full-length gene DNA was synthesized in the same manner as Example 1 based on the designed nucleic acid sequence of the PreM-M-E fused protein gene codon-optimized for West Nile virus followed by insertion into pBm-8 vector to produce pBM-8wnvpMME.

Infection with Baculovirus Introduced with PreM-M-E Fused Protein Gene Codon-Optimized for West Nile Virus A recombinant baculovirus was obtained in the same manner as Example 1 using pBm-8wnvpMME followed by inoculation of *Bombyx mori* pupas to obtain an emulsion of *Bombyx mori* pupas.

Recovery of West Nile Virus PreM-M-E Fused Protein and Confirmation of Expression The resulting emulsion of *Bombyx mori* pupas was subjected to ultrasonic treatment and purification in the same manner as Example 3. Expression of the purified West Nile virus PreM-M-E fused protein was confirmed by western blotting in the same manner as Example 3.

Evaluation of Activity

Immune reaction can be predicted from the amount of protein produced, and the effect in a neutralization test was estimated using antibody produced as a result thereof.

Reference Example 5

Design of DNA for Developing MERS Coronavirus Vaccine Suitable for Production in *Bombyx mori*

Design of Nucleic Acid Sequence of Spike Glycoprotein (S Protein) Gene Codon-Optimized for MERS Coronavirus The inventors of the present invention designed genetic information for expressing the S protein of MERS coronavirus in order to develop a vaccine against MERS coronavirus. First, a FLAG tag sequence (SEQ ID NO: 5) was added to the amino acid sequence registered with Genbank under Accession No. AGN52936 (SEQ ID NO: 28) to obtain an amino acid sequence of the MERS coronavirus S protein based on the nucleic acid design (SEQ ID NO: 29). The nucleic acid sequence of an S protein codon-optimized for MERS coronavirus was then designed in the same manner as Example 1 based on the amino acid sequence of this MERS coronavirus S protein (SEQ ID NO: 30). Correspondence between the designed nucleic acid sequence of the chimeric synthetic DNA and the amino acid sequence is shown in FIG. 20.

DNA Synthesis of S Protein Gene Codon-Optimized for MERS Coronavirus and Vector Construction Full-length gene DNA was synthesized in the same manner as Example 1 based on the designed nucleic acid sequence of the S protein gene codon-optimized for MERS coronavirus followed by insertion into pBm-8 vector to produce pBM-8mcvS.

Infection with Baculovirus Introduced with S Protein Gene Codon-Optimized for MERS Coronavirus A recombinant baculovirus was obtained in the same manner as Example 1 using pBm-8mcvS followed by inoculation of *Bombyx mori* pupas to obtain an emulsion of *Bombyx mori* pupas.

Recovery of MERS Coronavirus S Protein and Confirmation of Expression

The resulting emulsion of *Bombyx mori* pupas was subjected to ultrasonic treatment and purification in the same manner as Example 3. Expression of the purified MERS coronavirus S protein was confirmed by western blotting in the same manner as Example 3.

Evaluation of Activity

Immune reaction can be predicted from the amount of protein produced, and the effect in a neutralization test was estimated using antibody produced as a result thereof.

Reference Example 6

Design of DNA for Developing Foot and Mouth Disease Virus Vaccine Suitable for Production in *Bombyx mori*

Design of Nucleic Acid Sequence of VP4-VP2-VP3-VP1-2A-3C Fused Protein Codon-Optimized for Foot and Mouth Disease Virus The inventors of the present invention designed genetic information for expressing the VP4-VP2-VP3-VP1-2A-3C fused protein of foot and mouth disease virus in order to develop a vaccine against foot and mouth disease virus. First, a FLAG tag sequence (SEQ ID NO: 5) was added to the amino acid sequence obtained by binding from the N-terminal side towards the C-terminal side an amino acid sequence of VP4, Vp2, VP1, 2A and 3C proteins in an amino acid sequence predicted from the nucleic acid sequence registered with GenBank under Accession No. HV940030 (SEQ ID NO: 31) to obtain an amino acid sequence of the foot and mouth disease virus based on the nucleic acid design (SEQ ID NO: 32). The nucleic acid sequence of a VP4-VP2-VP3-VP1-2A-3C fused protein codon-optimized for foot and mouth disease virus was then designed in the same manner as Example 1 based on the amino acid sequence of this foot and mouth disease virus VP4-VP2-VP3-VP1-2A-3C protein (SEQ ID NO: 33). Correspondence between the designed nucleic acid sequence of the chimeric synthetic DNA and the amino acid sequence is shown in FIG. 21.

DNA Synthesis of VP4-VP2-VP3-VP1-2A-3C Fused Protein Gene Codon-Optimized for Foot and Mouth Disease Virus and Vector Construction Full-length gene DNA was synthesized in the same manner as Example 1 based on the designed nucleic acid sequence of the VP4-VP2-VP3-VP1-2A-3C fused protein gene codon-optimized for foot and mouth disease virus followed by insertion into pBm-8 vector to produce pBM-8fmdvP.

Infection with Baculovirus Introduced with VP4-VP2-VP3-VP1-2A-3C Fused Protein Gene Codon-Optimized for Foot and Mouth Disease Virus A recombinant baculovirus was obtained in the same manner as Example 1 using pBm-8fmdvP followed by inoculation of *Bombyx mori* pupas to obtain an emulsion of *Bombyx mori* pupas.

Recovery of Foot and Mouth Disease Virus VP4-VP2-VP3-VP1-2A-3C Fused Protein and Confirmation of Expression The resulting emulsion of Bombyx mori pupas was subjected to ultrasonic treatment and purification in the same manner as Example 3. Expression of the purified foot and mouth disease virus VP4-VP2-VP3-VP1-2A-3C fused protein was confirmed by western blotting in the same manner as Example 3.

Evaluation of Activity

Immune reaction can be predicted from the amount of protein produced, and the effect in a neutralization test was estimated using antibody produced as a result thereof.

The nucleic acid according to the present invention demonstrated the remarkable effects indicated below.

1) Protein derived from a dangerous virus is obtained by using artificially synthesized DNA without having to handle the dangerous virus. (Since dangerous viruses can be handled without requiring P4 or P3 facilities, there is no possibility of the virus escaping to the outside as a result of infecting people or adhering to clothing, thereby making it safe.)

2) An amino acid sequence having low pathogenicity can be designed from the start based on bioinformatics.

3) Amino acid sequences can be designed from the start while predicting future amino acid mutations based on bioinformatics and evolutionary analyses.

4) Although a gene sequence is determined from an amino acid sequence, and the amino acid sequence is completely identical to the original amino acid sequence with the exception of the virulent site and FLAG tag in an HA protein, for example, when a gene sequence is obtained therefrom, the homology thereof is only 77% (see, for example, FIG. 5), thereby making it possible to easily distinguish from the virus gene.

5) Since a FLAG tag sequence is attached to the C-terminal, even if the virus should happen to infect cells, there is a high degree of safety since there is no interaction between virus RNP and M1 protein.

6) Since a gene sequence is artificially designed using a codon usage optimized for Bombyx mori cells followed by incorporating in a vector, the expression level thereof in the Bombyx mori cells is significantly higher than that using a sequence derived from virus gene, and antigenicity is completely identical to that of the original virus.

7) As a result of using Bombyx mori cells, the sugar chain structure is not complex and antigenicity masking action attributable to sugar chains is extremely weak. Consequently, the increase in antibody titer when used as a vaccine is extremely high at 340 times that of purified HA protein derived from virus grown in chicken eggs.

8) The use of a FLAG tag facilitates confirmation of expression and purification.

The production of a vaccine in Bombyx mori by using this novel technology of the present application makes it possible to produce a component vaccine comprising only the active component at low cost while also allowing the vaccine to be produced in a shorter period of time. In addition, this also simultaneously solves the problem of egg allergies. Moreover, this technology also makes it possible to considerably reduce the amount of time required to produce seed viruses for rapid proliferation in embryonated chicken eggs, which in combination with the other aforementioned advantages, clearly makes this technology superior.

INDUSTRIAL APPLICABILITY

The nucleic acid of the present invention, which is artificially synthesized based on the design of a nucleic acid sequence codon-optimized for expression in Bombyx mori, is useful for producing a large amount of vaccine as previously described.

SEQUENCE LISTING FREE TEXT

SEQ ID NO: 1: HA gene DNA sequence of A/tufted duck/Fukushima/16/2011 (H5N1) avian influenza virus SEQ ID NO: 2: HA amino acid sequence of A/tufted duck/Fukushima/16/2011 (H5N1) avian influenza virus SEQ ID NO: 3: Modified HA amino acid sequence of A/tufted duck/Fukushima/16/2011 (H5N1) avian influenza virus SEQ ID NO: 4: HA gene DNA sequence codon-modified for A/tufted duck/Fukushima/16/2011 (H5N1) avian influenza virus SEQ ID NO: 5: FLAG tag amino acid sequence SEQ ID NO: 6: FLAG tag DNA sequence SEQ ID NO: 7: Highly pathogenic amino acid sequence SEQ ID NO: 8: Lowly pathogenic amino acid sequence SEQ ID NO: 9: HA gene DNA sequence of A/chicken/Sukabumi/2008 (H5N1) avian influenza virus SEQ ID NO: 10: HA amino acid sequence of A/chicken/Sukabumi/2008 (H5N1) avian influenza virus SEQ ID NO: 11: Modified HA amino acid sequence of A/chicken/Sukabumi/2008 (H5N1) avian influenza virus SEQ ID NO: 12: HA gene DNA sequence codon-optimized for A/chicken/Sukabumi/2008 (H5N1) avian influenza virus SEQ ID NO: 13: Core-E1-E2 fused protein amino acid sequence of hepatitis C virus SEQ ID NO: 14: Modified Core-E1-E2 fused protein amino acid sequence of hepatitis C virus SEQ ID NO: 15: Core-E1-E2 gene DNA sequence codon-optimized for hepatitis C virus SEQ ID NO: 16: HA amino acid sequence of A/Shanghai/02/2013 (H7N9) influenza virus SEQ ID NO: 17: Modified HA amino acid sequence of A/Shanghai/02/2013 (H7N9) influenza virus SEQ ID NO: 18: HA gene DNA sequence codon-optimized for A/Shanghai/02/2013 (H7N9) influenza virus SEQ ID NO: 19: PreM-M-E fused protein amino acid sequence of Japanese encephalitis virus SEQ ID NO: 20: PreM-M-E fused protein+FLAG tag amino acid sequence of Japanese encephalitis virus SEQ ID NO: 21: PreM-M-E fused protein gene DNA sequence codon-optimized for Japanese encephalitis virus SEQ ID NO: 22: G protein amino acid sequence of rabies virus SEQ ID NO: 23: G protein+FLAG tag amino acid sequence of rabies virus SEQ ID NO: 24: G protein gene DNA sequence codon-optimized for rabies virus SEQ ID NO: 25: PreM-M-E fused protein amino acid sequence of West Nile virus SEQ ID NO: 26: PreM-M-E fused protein+FLAG tag amino acid sequence of West Nile virus SEQ ID NO: 27: PreM-M-E fused protein gene DNA sequence codon-optimized for West Nile virus SEQ ID NO: 28: S protein amino acid sequence of MERS coronavirus SEQ ID NO: 29: S protein+FLAG tag amino acid sequence of MERS coronavirus SEQ ID NO: 30: S protein gene DNA sequence codon-optimized for MERS coronavirus SEQ ID NO: 31: VP4-VP2-VP3-VP1-2A-3C fused protein amino acid sequence of foot and mouth disease virus SEQ ID NO: 32: VP4-VP2-VP3-VP1-2A-3C fused protein+FLAG tag amino acid sequence of foot and mouth disease virus SEQ ID NO: 33: VP4-VP2-VP3-VP1-2A-3C fused protein gene DNA sequence codon-optimized for foot and mouth disease virus

SEQUENCE LISTING

<160> NUMBER OF SEQ ID NOS: 33

<210> SEQ ID NO 1
<211> LENGTH: 1742
<212> TYPE: DNA
<213> ORGANISM: Influenza A virus

<400> SEQUENCE: 1

```
ttcactctgt caaaatggag aaaatagtgc ttctctttac aacaatcggc cttgttaaaa      60
gcgatcatat ttgcattggt tatcatgcaa ataactcgac agagcaggtt gacacaataa     120
tggaaaagaa cgttactgtt acacatgccc aagcatact  ggaaaagaca cacaacggga     180
agctctgcga tctaaatgga gtgaagcctc tgattttaaa agattgtagt gtagcgggat     240
ggctcctcgg aaacccattg tgtgacgaat tcatcaatgt gccagaatgg tcttacatag     300
tagagaaggc caatccagcc aatgacctct gttacccagg gaatttcaac gattatgaag     360
aattgaaaca cctattgagc aggataaaac attttgagaa aatacagatc atccccaaag     420
actcttggtc agatcatgaa gcctcattgg gggtgagcgc agcatgttca tacccaggga     480
attcctcctt cttcagaaat gtggtatggc ttatcaaaaa ggacaatgca tacccaacaa     540
taaagaaagg ctacaataat accaaccaag aagatctctt ggtactgtgg gggattcacc     600
accctaatga tgaggcagag cagacaaggc tctatcaaaa cccaaccacc tatatttcca     660
ttgggacatc aacactaaac cagagattgg taccaaaaat agccactaga tccaaaataa     720
acgggcaaag gggcaggata gatttcttct ggacaatttt aaaaccgaat gatgcaatcc     780
acttcgagag taatggaaat ttcattgctc agaatatgc  atacaaaatt gttaagaaag     840
gagactccac aattatgaaa agtgaagtgg aatatggtaa ctgcaacacc aggtgtcaga     900
ctccgatagg ggcgataaac tctagtatgc cattccacaa catacaccct ctcaccatcg     960
gagaatgtcc caaatatgtg aaatcaaaca aattagtcct tgcgactggg ctcagaaata    1020
gtcctcaaag agagagaaga agaaaaagag gactgtttgg agctatagca ggttttatag    1080
agggaggatg gcagggaatg gtagatggtt ggtatgggta ccaccacagc aatgagcagg    1140
ggagtgggta cgctgcagac aaagaatcta ctcaaaaggc aatagacgga gtcaccaata    1200
aggtcaactc gatcattgac aaaatgaaca ctcagtttga ggccgtagga agggaattta    1260
acaacttaga gaggagaata gagaatttaa acaagaagat ggaagacgga ttcctagatg    1320
tttggactta taatgctgaa cttctggttc tcatggaaaa tgagagaact ctagatttcc    1380
atgactcaaa tgtcaagaac ctttacgata aggtcagact acagcttaag gataatgcaa    1440
aagagttggg taacggttgt ttcgagttct atcacaaatg taataatgaa tgtatggaaa    1500
gtgtaagaaa cggaacgtat gactacccgc agtattcaga agaagcaaga ctaaaaagag    1560
aggaaataag tggagtaaaa ttggaatcaa taggaatcta ccaaatactg tcaatttatt    1620
caacagtggc gagttcccta gtgctggcaa tcatgatggc tggtctgtct ttatggatgt    1680
gttccaacgg atcgttacag tgcagaattt gcatttaagt ctgtgagttc aaattgtggt    1740
ta                                                                   1742
```

<210> SEQ ID NO 2
<211> LENGTH: 566
<212> TYPE: PRT

<213> ORGANISM: Influenza A virus

<400> SEQUENCE: 2

```
Met Glu Lys Ile Val Leu Leu Phe Th

```
Ile Asp Lys Met Asn Thr Gln Phe Glu Ala Val Gly Arg Glu Phe Asn
            405                 410                 415

Asn Leu Glu Arg Arg Ile Glu Asn Leu Asn Lys Lys Met Glu Asp Gly
        420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Lys Asp Asn Ala Lys Glu Leu Gly Asn
465                 470                 475                 480

Gly Cys Phe Glu Phe Tyr His Lys Cys Asn Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Ile
        515                 520                 525

Tyr Gln Ile Leu Ser Ile Tyr Ser Thr Val Ala Ser Ser Leu Val Leu
    530                 535                 540

Ala Ile Met Met Ala Gly Leu Ser Leu Trp Met Cys Ser Asn Gly Ser
545                 550                 555                 560

Leu Gln Cys Arg Ile Cys
                565

<210> SEQ ID NO 3
<211> LENGTH: 572
<212> TYPE: PRT
<213> ORGANISM: Artificial Sequence
<220> FEATURE:
<223> OTHER INFORMATION: modified HA protein

<400> SEQUENCE: 3

Met Glu Lys Ile Val Leu Leu Phe Thr Thr Ile Gly Leu Val Lys Ser
1               5                   10                  15

Asp His Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Leu Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asp Ser Trp Ser Asp His Glu Ala Ser
    130                 135                 140

Leu Gly Val Ser Ala Ala Cys Ser Tyr Gln Gly Asn Ser Ser Phe Phe
145                 150                 155                 160

Arg Asn Val Val Trp Leu Ile Lys Lys Asp Asn Ala Tyr Pro Thr Ile
                165                 170                 175

Lys Lys Gly Tyr Asn Asn Thr Asn Gln Glu Asp Leu Leu Val Leu Trp
            180                 185                 190
```

```
Gly Ile His His Pro Asn Asp Glu Ala Glu Gln Thr Arg Leu Tyr Gln
            195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Ile Asn Gly Gln Arg Gly
225                 230                 235                 240

Arg Ile Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Val Glu Tyr Gly
    275                 280                 285

Asn Cys Asn Thr Arg Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
    355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
    435                 440                 445

Thr Leu Asp Phe His Asp Ser Asn Val Lys Asn Leu Tyr Asp Lys Val
450                 455                 460

Arg Leu Gln Leu Lys Asp Asn Ala Lys Glu Leu Gly Asn Gly Cys Phe
465                 470                 475                 480

Glu Phe Tyr His Lys Cys Asn Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
    515                 520                 525

Leu Ser Ile Tyr Ser Thr Val Ala Ser Ser Leu Val Leu Ala Ile Met
530                 535                 540

Met Ala Gly Leu Ser Leu Trp Met Cys Ser Asn Gly Ser Leu Gln Cys
545                 550                 555                 560

Arg Ile Cys Ile Asp Tyr Lys Asp Asp Asp Lys
                565                 570
```

<210> SEQ ID NO 4
<211> LENGTH: 1719
<212> TYPE: DNA
<213> ORGANISM: Artificial Sequence
<220> FEATURE:
<223> OTHER INFORMATION: codon modified HA protein

<400> SEQUENCE: 4

```
atggaaaaaa tcgtgctgct gttcacaaca atcggtctgg tgaaatcaga ccacatctgc    60
atcggttacc acgctaacaa ctcaacagaa caagtggaca caatcatgga aaaaaacgtg   120
acagtgacac acgctcaaga catcctggaa aaaacacaca acggtaaact gtgcgacctg   180
aacggtgtga acctctgat cctgaaagac tgctcagtgg ctggttggct gctgggtaac   240
cctctgtgcg acgaattcat caacgtgcct gaatggtcat acatcgtgga aaaagctaac   300
cctgctaacg acctgtgcta ccctggtaac ttcaacgact acgaagaact gaaacacctg   360
ctgtcaagaa tcaaccactt cgaaaaaatc caaatcatcc ctaaagactc atggtcagac   420
cacgaagctt cactgggtgt gtcagctgct tgctcatacc aaggtaactc atcattcttc   480
agaaacgtgg tgtggctgat caaaaaagac aacgcttacc ctacaatcaa aaaaggttac   540
aacaacacaa accaagaaga cctgctggtg ctgtggggta ccaccaccc taacgacgaa   600
gctgaacaaa caagactgta ccaaaaccct acaacataca tctcaatcgg tacatcaaca   660
ctgaaccaaa gactggtgcc taaaatcgct acaagatcaa aaatcaacgg tcaaagaggt   720
agaatcgact tcttctggac aatcctgaaa cctaacgacg ctatccactt cgaatcaaac   780
ggtaacttca tcgctcctga atacgcttac aaaatcgtga aaaaggtga ctcaacaatc   840
atgaaatcag aagtggaata cggtaactgc aacacaagat gccaaacacc tatcggtgct   900
atcaactcat caatgccttt ccacaacatc caccctctga aatcggtga atgccctaaa   960
tacgtgaaat caaacaaact ggtgctggct acaggtctga aaactcacc tcaaagagaa  1020
acaagaggtc tgttcggtgc tatcgctggt ttcatcgaag tggttggca aggtatggtg  1080
gacggttggt acggttacca ccactcaaac gaacaaggtt caggttacgc tgctgacaaa  1140
gaatcaacac aaaaagctat cgacggtgtg acaaacaaag tgaactcaat catcgacaaa  1200
atgaacacac aattcgaagc tgtgggtaga gaattcaaca acctggaaag aagaatcgaa  1260
aacctgaaca aaaaaatgga agacggtttc ctggacgtgt ggacatacaa cgctgaactg  1320
ctggtgctga tggaaaacga agaacactg gacttccacg actcaaacgt gaaaaacctg  1380
tacgacaaag tgagactgca actgaaagac aacgctaaag aactgggtaa cggttgcttc  1440
gaattctacc acaaatgcaa caacgaatgc atggaatcag tgagaaacgg tacatacgac  1500
taccctcaat actcagaaga agctagactg aaaagagaag aaatctcagg tgtgaaactg  1560
gaatcaatcg gtatctacca aatcctgtca atctactcaa cagtggcttc atcactggtg  1620
ctggctatca tgatggctgg tctgtcactg tggatgtgct caaacggttc actgcaatgc  1680
agaatctgca tcgactacaa agacgacgac gacaaataa                         1719
```

<210> SEQ ID NO 5
<211> LENGTH: 8
<212> TYPE: PRT
<213> ORGANISM: Artificial Sequence
<220> FEATURE:
<223> OTHER INFORMATION: Flag tag

<400> SEQUENCE: 5

Asp Tyr Lys Asp Asp Asp Asp Lys
1               5

<210> SEQ ID NO 6
<211> LENGTH: 24
<212> TYPE: DNA
<213> ORGANISM: Artificial Sequence

```
<220> FEATURE:
<223> OTHER INFORMATION: FLAG tag

<400> SEQUENCE: 6
gactacaaag acgacgacga caaa                                               24

<210> SEQ ID NO 7
<211> LENGTH: 7
<212> TYPE: PRT
<213> ORGANISM: Influenza A virus

<400> SEQUENCE: 7

Arg Glu Arg Arg Arg Lys Arg
1               5

<210> SEQ ID NO 8
<211> LENGTH: 4
<212> TYPE: PRT
<213> ORGANISM: Artificial Sequence
<220> FEATURE:
<223> OTHER INFORMATION: putative pathogenic site

<400> SEQUENCE: 8

Arg Glu Thr Arg
1

<210> SEQ ID NO 9
<211> LENGTH: 1776
<212> TYPE: DNA
<213> ORGANISM: Influenza A virus

<400> SEQUENCE: 9
agcaaaagca gggtataat  ctgtaaaaat ggagaaaaca gcgcttcttc ttgcaatagt          60
cagccttgtt aaaagtgatc agatttgcat tggttaccat gcaaacaatt caacagagca        120
ggtcgacaca atcatggaaa agaacgttac tgttacacat gcccaagaca tactggaaaa        180
gacacacaac gggaagctct gcgatctaga tggagtgaag cctctaattt taagagattg        240
tagtgtagct gggtggctcc tcgggaaccc aatgtgtgac gaattcatca agtaaaggaa        300
atggtcttac atagtggaga aggccagtcc aaccaatgac ctctgttacc cagggagttt        360
caacgactat gaagaactga aacacctatt gagcagaata aaacattttg agaaaattcg        420
aatcatcccc agaagtgatt ggtctgatca tgaaacctcg ggagtgagct cagcatgtcc        480
atacctggga agtccctcct tttttagaaa tgtggtatgg cttacccaaa agaacagtac        540
atacccaata taaagaaaa gctacaagaa taccaaccaa gaagatcttt tgatactgtg         600
gggaattcac cattctaata atgtggaaga gcagacaagg ctatatcaaa acctaaccac        660
ctatatttcc attgggacat caacactaaa ccagagatcg gtaccaaaaa tagctactag        720
aaccaaagta cacgggcaaa gtggaaggat ggatttcttc tggacaattt taaattctaa        780
tgatacaatc tacttcgaga gtaatggaaa tttcattgct ccagaatatg catacaaaat        840
tgtcaagaaa ggggactcag caattatgaa aagtgaattg gaatatggtg actgcaacac        900
taaatgtcaa actccaatgg gggcgataaa ctctagtatg ccattccaca acatacaccc        960
tctcactatc ggggaatgcc ccaaatatgt gaaatcaaac agattagtcc ttgcaacagg       1020
gctcagaaat agccctcaaa gagagagcag aaggaaaaag agaggactat ttggagctat       1080
agcaggtttt atagagggag gatggcaggg aatggtagat ggttggtatg gtaccatca        1140 tagcaatgag caggggagtg gtacgcgctgc agataaagaa tccactcaaa aggcaataga      1200
```

-continued

```
tggaatcacc aataaggtca actcaatcat tgacaagatg aacactcagt ttgaggccgt   1260
tggaagggaa tttaataact tagaaaggag aatagaaat ttaaacaaga agatggaaga    1320
cgggtttcta gatgtttgga cttataatgc cgaacttctg gttctcatgg aaaatgagag   1380
aactctagac tttcatgact caaatgttaa gaaccttttac gacaaagtcc gactacagct   1440
tagggataat gcaaggagc tgggtaatgg ttgtttcgag ttctatcaca aatgtgataa    1500
tgaatgtatg gaaagtataa gaaacggaac gtacaactat ccacagtatt cagaagaagc   1560
aaggttaaaa agagaggaaa taagtggggt aaaattggaa tcaataggaa cttaccaaat   1620
actgtcaatt tattcaacag tagcgagttc tctagcactg gcaatcatga tggctggtct   1680
atctttatgg atgtgctcca atgggtcttt acaatgcaga atttgcattt aaatttgtga   1740
gttcagattg tagttaaaaa caccctgtt tctact                              1776
```

<210> SEQ ID NO 10
<211> LENGTH: 567
<212> TYPE: PRT
<213> ORGANISM: Influenza A virus

<400> SEQUENCE: 10

```
Met Glu Lys Thr Ala Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Lys Val Lys Glu Trp Ser Tyr Ile Val
                85                  90                  95

Glu Lys Ala Ser Pro Thr Asn Asp Leu Cys Tyr Pro Gly Ser Phe Asn
            100                 105                 110

Asp Tyr Glu Glu Leu Lys His Leu Leu Ser Arg Ile Lys His Phe Glu
        115                 120                 125

Lys Ile Arg Ile Ile Pro Arg Ser Asp Trp Ser Asp His Glu Thr Ser
    130                 135                 140

Gly Val Ser Ser Ala Cys Pro Tyr Leu Gly Ser Pro Ser Phe Phe Arg
145                 150                 155                 160

Asn Val Val Trp Leu Thr Gln Lys Asn Ser Thr Tyr Pro Ile Ile Lys
                165                 170                 175

Lys Ser Tyr Lys Asn Thr Asn Gln Glu Asp Leu Leu Ile Leu Trp Gly
            180                 185                 190

Ile His His Ser Asn Asn Val Glu Glu Gln Thr Arg Leu Tyr Gln Asn
        195                 200                 205

Leu Thr Thr Tyr Ile Ser Ile Gly Thr Ser Thr Leu Asn Gln Arg Ser
    210                 215                 220

Val Pro Lys Ile Ala Thr Arg Thr Lys Val His Gly Gln Ser Gly Arg
225                 230                 235                 240

Met Asp Phe Phe Trp Thr Ile Leu Asn Ser Asn Asp Thr Ile Tyr Phe
                245                 250                 255

Glu Ser Asn Gly Asn Phe Ile Ala Pro Glu Tyr Ala Tyr Lys Ile Val
            260                 265                 270
```

```
Lys Lys Gly Asp Ser Ala Ile Met Lys Ser Glu Leu Glu Tyr Gly Asp
            275                 280                 285

Cys Asn Thr Lys Cys Gln Thr Pro Met Gly Ala Ile Asn Ser Ser Met
        290                 295                 300

Pro Phe His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Arg Glu Ser Arg Arg Lys Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
370                 375                 380

Ser Thr Gln Lys Ala Ile Asp Gly Ile Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Ile Arg Asn Gly Thr Tyr Asn Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
530                 535                 540

Ala Ile Met Met Ala Gly Leu Ser Leu Trp Met Cys Ser Asn Gly Ser
545                 550                 555                 560

Leu Gln Cys Arg Ile Cys Ile
                565

<210> SEQ ID NO 11
<211> LENGTH: 571
<212> TYPE: PRT
<213> ORGANISM: Artificial sequence
<220> FEATURE:
<223> OTHER INFORMATION: modified HA protein

<400> SEQUENCE: 11

Met Glu Lys Thr Ala Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60
```

-continued

```
Pro Leu Ile Leu Arg Asp Cys Ser Val Ala Gly Trp Leu Leu Gly Asn
 65                  70                  75                  80

Pro Met Cys Asp Glu Phe Ile Lys Val Lys Glu Trp Ser Tyr Ile Val
                 85                  90                  95

Glu Lys Ala Ser Pro Thr Asn Asp Leu Cys Tyr Pro Gly Ser Phe Asn
            100                 105                 110

Asp Tyr Glu Glu Leu Lys His Leu Leu Ser Arg Ile Lys His Phe Glu
        115                 120                 125

Lys Ile Arg Ile Ile Pro Arg Ser Asp Trp Ser Asp His Glu Thr Ser
130                 135                 140

Gly Val Ser Ser Ala Cys Pro Tyr Leu Gly Ser Pro Ser Phe Phe Arg
145                 150                 155                 160

Asn Val Val Trp Leu Thr Gln Lys Asn Ser Thr Tyr Pro Ile Ile Lys
                165                 170                 175

Lys Ser Tyr Lys Asn Thr Asn Gln Glu Asp Leu Leu Ile Leu Trp Gly
            180                 185                 190

Ile His His Ser Asn Asn Val Glu Glu Gln Thr Arg Leu Tyr Gln Asn
        195                 200                 205

Leu Thr Thr Tyr Ile Ser Ile Gly Thr Ser Thr Leu Asn Gln Arg Ser
210                 215                 220

Val Pro Lys Ile Ala Thr Arg Thr Lys Val His Gly Gln Ser Gly Arg
225                 230                 235                 240

Met Asp Phe Phe Trp Thr Ile Leu Asn Ser Asn Asp Thr Ile Tyr Phe
                245                 250                 255

Glu Ser Asn Gly Asn Phe Ile Ala Pro Glu Tyr Ala Tyr Lys Ile Val
            260                 265                 270

Lys Lys Gly Asp Ser Ala Ile Met Lys Ser Glu Leu Glu Tyr Gly Asp
        275                 280                 285

Cys Asn Thr Lys Cys Gln Thr Pro Met Gly Ala Ile Asn Ser Ser Met
290                 295                 300

Pro Phe His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Arg Glu Ser Arg Gly Leu Phe Gly Ala Ile Ala Gly Phe Ile Glu
            340                 345                 350

Gly Gly Trp Gln Gly Met Val Asp Gly Trp Tyr Gly Tyr His His Ser
        355                 360                 365

Asn Glu Gln Gly Ser Gly Tyr Ala Ala Asp Lys Glu Ser Thr Gln Lys
370                 375                 380

Ala Ile Asp Gly Ile Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
        435                 440                 445

Leu Asp Phe His Asp Ser Asn Val Lys Asn Leu Tyr Asp Lys Val Arg
450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Ile Arg Asn Gly
```

```
                485                 490                 495
Thr Tyr Asn Tyr Pro Gln Tyr Ser Glu Glu Ala Arg Leu Lys Arg Glu
            500                 505                 510

Glu Ile Ser Gly Val Lys Leu Glu Ser Ile Gly Thr Tyr Gln Ile Leu
        515                 520                 525

Ser Ile Tyr Ser Thr Val Ala Ser Ser Leu Ala Leu Ala Ile Met Met
    530                 535                 540

Ala Gly Leu Ser Leu Trp Met Cys Ser Asn Gly Ser Leu Gln Cys Arg
545                 550                 555                 560

Ile Cys Ile Asp Tyr Lys Asp Asp Asp Lys
                565                 570

<210> SEQ ID NO 12
<211> LENGTH: 1716
<212> TYPE: DNA
<213> ORGANISM: Artificial sequence
<220> FEATURE:
<223> OTHER INFORMATION: codon modified HA protein

<400> SEQUENCE: 12
atggaaaaaa cagctctgct gctggctatc gtgtcactgg tgaaatcaga ccaaatctgc     60
atcggttacc acgctaacaa ctcaacagaa caagtggaca caatcatgga aaaaaacgtg    120
acagtgacac acgctcaaga catcctggaa aaaacacaca cggtaaaact gtgcgacctg    180
gacggtgtga acctctgat cctgagagac tgctcagtgg ctggttggct gctgggtaac    240
cctatgtgcg acgaattcat caaagtgaaa gaatggtcat acatcgtgga aaaagcttca    300
cctacaaacg acctgtgcta ccctggttca ttcaacgact acgaagaact gaaacacctg    360
ctgtcaagaa tcaaacactt cgaaaaaatc agaatcatcc ctagatcaga ctggtcagac    420
cacgaaacat caggtgtgtc atcagcttgc ccttacctgg ttcaccttc attcttcaga    480
aacgtggtgt ggctgacaca aaaaaactca acatacccta tcatcaaaaa atcatacaaa    540
aacacaaacc aagaagacct gctgatcctg tggggtatcc accactcaaa caacgtggaa    600
gaacaaacaa gactgtacca aaacctgaca catacatct caatcggtac atcaacactg    660
aaccaaagat cagtgcctaa aatcgctaca gaacaaaaag tgcacggtca atcaggtaga    720
atggactct tctggacaat cctgaactca acgacacaa tctacttcga atcaaacggt    780
aacttcatcg ctcctgaata cgcttacaaa atcgtgaaaa aggtgactca agctatcatg    840
aaatcagaac tggaatacgg tgactgcaac acaaaatgcc aaacacctat gggtgctatc    900
aactcatcaa tgcctttcca caacatccac cctctgacaa tcggtgaatg ccctaaatac    960
gtgaaatcaa acagactggt gctggctaca ggtctgagaa actcacctca agagaatca   1020
agaggtctgt tcggtgctat cgctggtttc atcgaaggtg gttggcaagg tatggtggac   1080
ggttggtacg gttaccacca ctcaaacgaa caaggttcag gttacgctgc tgacaaagaa   1140
tcaacacaaa aagctatcga cggtatcaca aacaaagtga actcaatcat cgacaaaatg   1200
aacacacaat cgaagctgt gggtagagaa ttcaacaacc tggaaagaag aatcgaaaac   1260
ctgaacaaaa aaatggaaga cggtttcctg gacgtgtgga catacaacgc tgaactgctg   1320
gtgctgatgg aaaacgaaag aacactggac ttccacgact caaacgtgaa aaacctgtac   1380
gacaaagtga actgcaact gagagacaac gctaagaac tgggtaacgg ttgcttcgaa   1440
ttctaccaca aatgcgacaa cgaatgcatg gaatcaatca gaacggtac atacaactac   1500
cctcaatact cagaagaagc tagactgaaa agagaagaa tctcaggtgt gaaactggaa   1560
```

```
tcaatcggta cataccaaat cctgtcaatc tactcaacag tggcttcatc actggctctg    1620
gctatcatga tggctggtct gtcactgtgg atgtgctcaa acggttcact gcaatgcaga    1680
atctgcatcg actacaaaga cgacgacgac aaataa                              1716
```

<210> SEQ ID NO 13
<211> LENGTH: 745
<212> TYPE: PRT
<213> ORGANISM: Hepatitis C virus

<400> SEQUENCE: 13

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ala Tyr His Val Thr Asn Asp Cys Ala
        195                 200                 205

Asn Thr Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Ile Pro Thr Thr
                245                 250                 255

Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Val Ser
        275                 280                 285

Gln Leu Phe Val Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Ala Ala Leu Met Val Ser Gln
                325                 330                 335

Leu Leu Arg Ile Pro Gln Ala Val Val Asp Met Val Ala Gly Ala His
            340                 345                 350
```

Trp Gly Ile Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly Thr
370                 375                 380

Thr His Val Ser Gly Gly Ala Ala Gly Arg Asn Thr Tyr Gly Leu Thr
385                 390                 395                 400

Ser Leu Phe Thr Pro Gly Ala Ser Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Thr His Arg Phe Asn
        435                 440                 445

Ala Ser Gly Cys Pro Glu Arg Leu Ala His Cys Arg Pro Ile Asp Thr
450                 455                 460

Phe Ala Gln Gly Trp Gly Pro Ile Thr Tyr Ala Gly Gln Arg Gly Leu
465                 470                 475                 480

Asp Gln Arg Pro Tyr Cys Trp His Tyr Ala Pro Lys Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Val Pro Thr Tyr Thr
        515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Ser Thr Gly Tyr
545                 550                 555                 560

Thr Lys Thr Cys Gly Gly Pro Pro Cys Asp Ile Gly Gly Ala Gly Asn
                565                 570                 575

Asn Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Phe
610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
690                 695                 700

Ile Gly Ser Val Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu
            740                 745

<210> SEQ ID NO 14
<211> LENGTH: 754

<212> TYPE: PRT
<213> ORGANISM: Artificial sequence
<220> FEATURE:
<223> OTHER INFORMATION: modified Core-E1-E2 proteins

<400> SEQUENCE: 14

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr His Val Ser Gly Gly Ala Ala Gly Arg Asn Thr Tyr Gly Leu Thr
385                 390                 395                 400

Ser Leu Phe Thr Pro Gly Ala Ser Gln Asn Ile Gln Leu Ile Asn Thr
            405                 410                 415

Asn Gly Ser Trp His Ile Asn Arg Thr Ala Leu Asn Cys Asn Asp Ser
        420                 425                 430

Leu Asn Thr Gly Phe Leu Ala Ala Leu Phe Tyr Thr His Arg Phe Asn
    435                 440                 445

Ala Ser Gly Cys Pro Glu Arg Leu Ala His Cys Arg Pro Ile Asp Thr
450                 455                 460

Phe Ala Gln Gly Trp Gly Pro Ile Thr Tyr Ala Gly Gln Arg Gly Leu
465                 470                 475                 480

Asp Gln Arg Pro Tyr Cys Trp His Tyr Ala Pro Lys Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Val Pro Thr Tyr Thr
        515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Ser Thr Gly Tyr
545                 550                 555                 560

Thr Lys Thr Cys Gly Gly Pro Pro Cys Asp Ile Gly Gly Ala Gly Asn
                565                 570                 575

Asn Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Ile Gly Ser Val Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Arg Asp Tyr Lys Asp Asp Asp
            740                 745                 750

Asp Lys

<210> SEQ ID NO 15
<211> LENGTH: 2265
<212> TYPE: DNA
<213> ORGANISM: Artificial sequence
<220> FEATURE:
<223> OTHER INFORMATION: codon modified Core-E1-E2 proteins

<400> SEQUENCE: 15

```
atgtcaacaa accctaaacc tcaaagaaaa acaaaaagaa acacaaacag aagacctcaa      60
gacgtgaaat tccctggtgg tggtcaaatc gtgggtggtg tgtacctgct gcctagaaga     120
ggtcctagac tgggtgtgag agctacaaga aaaacatcag aaagatcaca acctagaggt     180
agaagacaac ctatccctaa agctagacaa cctgaaggta gagcttgggc tcaacctggt     240
taccctthgc ctctgtacgg taacgaaggt atgggttggg ctggttggct gctgtcacct     300
agaggttcaa gaccttcatg gggtcctaca gaccctagaa gaagatcaag aaacctgggt     360
aaagtgatcg acacactgac atgcggtttc gctgacctga tggttacat ccctctggtg      420
ggtgctcctc tgggtggtgc tgctagagct ctggctcacg gtgtgagagt gctggaagac     480
ggtgtgaact acgctacagg taacctgcct ggttgctcat tctcaatctt cctgctggct     540
ctgctgtcat gcctgacaat ccctgcttca gcttacgaag tgagaaacgt gtcaggtgct     600
taccacgtga caaacgactg cgctaacaca tcaatcgtgt acgaagctgc tgacatgatc     660
atgcacacac ctggttgcgt gccttgcgtg agagaaaaca actcatcaag atgctgggtg     720
gctctgacac ctacactggc tgctagaaac gcttcaatcc ctacaacaac aatcagaaga     780
cacgtggacc tgctggtggg tgctgctgct ttctgctcag ctatgtacgt gggtgacctg     840
tgcggttcag tgttcctggt gtcacaactg ttcgtgttct cacctagaag acacgaaaca     900
gtgcaagact gcaactgctc aatctaccct ggtcacgtgt caggtcacag aatggcttgg     960
gacatgatga tgaactggtc acctacagct gctctgatgg tgtcacaact gctgagaatc    1020
cctcaagctg tggtggacat ggtggctggt gctcactggg gtatcctggc tggtctggct    1080
tactactcaa tggtgggtaa ctgggctaaa gtgctgatcg tgatgctgct gttcgctggt    1140
gtggacggta caacacacgt gtcaggtggt gctgctggta aaacacata cggtctgaca    1200
tcactgttca cacctggtgc ttcacaaaac atccaactga tcaacacaaa cggttcatgg    1260
cacatcaaca gaacagctct gaactgcaac gactcactga acacaggttt cctggctgct    1320
ctgttctaca cacacagatt caacgcttca ggttgccctg aaagactggc tcactgcaga    1380
cctatcgaca cattgctca aggttggggt cctatcacat acgctggtca agaggtctg     1440
gaccaaagac cttactgctg gcactacgct cctaaacctt gcggtatcgt gcctgcttca    1500
caagtgtgcg gtcctgtgta ctgcttcaca ccttcacctg tggtggtggg tacaacagac    1560
agattcggtg tgcctacata cacatggggt gaaaacgaaa cagacgtgct gctgctgaac    1620
aacacaagac tcctcaagg taactggttc ggttgcacat ggatgaactc aacaggttac    1680
acaaaaacat gcggtggtcc tccttgcgac atcggtggtg ctggtaacaa cacactgatc    1740
tgccctacag actgcttcag aaaacacct gaagctacat acacaaaatg cggttcaggt    1800
ccttggctga cacctagatg catggtggac taccttaca gactgtggca ctaccttgc     1860
acagtgaact tcacaatctt caaagtgaga atgtacgtgg tggtgtgga acacagactg     1920
aacgctgctt gcaactggac aagaggtgaa agatgcgacc tggaagacag agacagatca    1980
gaactgtcac ctctgctgct gtcaacaaca gaatggcaaa tcctgccttg ctcattcaca    2040
acactgcctg ctctgtcaac aggtctgatc cacctgcacc aaaacatcgt ggacgtgcaa    2100
tacctgtacg gtatcggttc agtggtggtg tcattcgcta tcaaatggga atacgtgctg    2160
ctgctgttcc tgctgctggc tgacgctaga gtgtgcgctt gcctgtggat gatgctgctg    2220
atcgctcaag ctgaaagaga ctacaaagac gacgacgaca aataa                   2265
```

```
<210> SEQ ID NO 16
<211> LENGTH: 560
<212> TYPE: PRT
<213> ORGANISM: Influenza A virus

<400> SEQUENCE: 16

Met Asn Thr G

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
            405                 410                 415

Gly Asn Val Ile Asn Trp Thr Arg Asp Ser Ile Thr Glu Val Trp Ser
        420                 425                 430

Tyr Asn Ala Glu Leu Leu Val Ala Met Glu Asn Gln His Thr Ile Asp
    435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
            485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 17
<211> LENGTH: 569
<212> TYPE: PRT
<213> ORGANISM: Artificial sequence
<220> FEATURE:
<223> OTHER INFORMATION: modified HA protein

<400> SEQUENCE: 17

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Asp Gln Thr Lys Leu Tyr Gly Ser Gly Asn
        195                 200                 205
Lys Leu Val Thr Val Gly Ser Ser Asn Tyr Gln Gln Ser Phe Val Pro
    210                 215                 220
Ser Pro Gly Ala Arg Pro Gln Val Asn Asp Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Gly Val Gln Val Asp Ala Asn Cys Glu Gly
        275                 280                 285
Asp Cys Tyr His Ser Gly Gly Thr Ile Ile Ser Asn Leu Pro Phe Gln
    290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
    370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
    450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
        515                 520                 525
Ser Phe Gly Ala Ser Cys Phe Ile Leu Leu Ala Ile Val Met Gly Leu
    530                 535                 540
Val Phe Ile Cys Val Lys Asn Gly Asn Met Arg Cys Thr Ile Cys Ile
545                 550                 555                 560
Asp Tyr Lys Asp Asp Asp Asp Lys Glx
                565

<210> SEQ ID NO 18
<211> LENGTH: 1707
<212> TYPE: DNA
<213> ORGANISM: Artificial sequence
<220> FEATURE:
<223> OTHER INFORMATION: codon modified HA protein

<400> SEQUENCE: 18

```
atgaacacac aaatcctggt gttcgctctg atcgctatca tccctacaaa cgctgacaaa      60
atctgcctgg tcaccacgc tgtgtcaaac ggtacaaaag tgaacacact gacagaaaga     120
ggtgtggaag tggtgaacgc tacagaaaca gtggaaagaa caaacatccc tagaatctgc    180
tcaaaaggta aagaacagt ggacctgggt caatgcggtc tgctgggtac aatcacaggt     240
cctcctcaat gcgaccaatt cctggaattc tcagctgacc tgatcatcga agaagagaa     300
ggttcagacg tgtgctaccc tggtaaattc gtgaacgaag aagctctgag acaaatcctg    360
agagaatcag gtggtatcga caaagaagct atgggtttca catactcagg tatcagaaca    420
aacggtgcta catcagcttg cagaagatca ggttcatcat tctacgctga atgaaatgg     480
ctgctgtcaa acacagacaa cgctgctttc cctcaaatga caaatcata caaaaacaca    540
agaaaatcac ctgctctgat cgtgtggggt atccaccact cagtgtcaac agctgaccaa    600
acaaaactgt acggttcagg taacaaactg gtgacagtgg ttcatcaaa ctaccaacaa    660
tcattcgtgc cttcacctgg tgctagacct caagtgaacg acctgtcagg tagaatcgac    720
ttccactggc tgatgctgaa ccctaacgac acagtgacat tctcattcaa cggtgctttc    780
atcgctcctg acagagcttc attcctgaga ggtaaatcaa tgggtatcca atcaggtgtg    840
caagtggacg ctaactgcga aggtgactgc taccactcag gtggtacaat catctcaaac    900
ctgcctttcc aaaacatcga ctcaagagct gtgggtaaat gccctagata cgtgaaacaa    960
agatcactgc tgctggctac aggtatgaaa aacgtgcctg aaatccctaa aggtagaggt   1020
ctgttcggtg ctatcgctgg tttcatcgaa aacgttggg aaggtctgat cgacggttgg    1080
tacggttca gacaccaaaa cgctcaaggt gaaggtacag ctgctgacta caaatcaaca   1140
caatcagcta tcgaccaaat cacaggtaaa ctgaacgac tgatcgaaaa aacaaaccaa   1200
caattcgaac tgatcgacaa cgaattcaac gaagtggaaa acaaatcgg taacgtgatc    1260
aactggacaa gagactcaat cacagaagtg tggtcataca cgctgaaact gctggtggct    1320
atggaaaacc aacacacaat cgacctggct gactcagaaa tggacaaact gtacgaaaga    1380
gtgaaaagac aactgagaga aaacgctgaa gaagacggta caggttgctt cgaaatcttc    1440
cacaaatgcg acgacgactg catggcttca atcagaaaca acacatacga ccactcaaaa    1500
tacagagaag aagctatgca aaacagaatc caaatcgacc ctgtgaaact gtcatcaggt    1560
tacaaagacg tgatcctgtg gttctcattc ggtgcttcat gcttcatcct gctggctatc    1620
gtgatgggtc tggtgttcat ctgcgtgaaa aacggtaaca tgagatgcac aatctgcatc    1680
gactacaaag acgacgacga caaataa                                        1707
```

<210> SEQ ID NO 19
<211> LENGTH: 667
<212> TYPE: PRT
<213> ORGANISM: Japanese encephalitis virus

<400> SEQUENCE: 19

```
Met Lys Leu Ser Asn Phe Gln Gly Lys Leu Leu Met Thr Val Asn Asn
1               5                   10                  15

Thr Asp Ile Ala Asp Val Ile Val Ile Pro Thr Ser Lys Gly Glu Asn
            20                  25                  30

Arg Cys Trp Val Arg Ala Ile Asp Val Gly Tyr Met Cys Glu Asp Thr
        35                  40                  45

Ile Thr Tyr Glu Cys Pro Lys Leu Thr Met Gly Asn Asp Pro Glu Asp
```

-continued

```
                50                  55                  60
Val Asp Cys Trp Cys Asp Asn Gln Glu Val Tyr Val Gln Tyr Gly Arg
 65                  70                  75                  80

Cys Thr Arg Thr Arg His Ser Lys Arg Ser Arg Ser Val Ser Val
                 85                  90                  95

Gln Thr His Gly Glu Ser Ser Leu Val Asn Lys Glu Ala Trp Leu
            100                 105                 110

Asp Ser Thr Lys Ala Thr Arg Tyr Leu Met Lys Thr Glu Asn Trp Ile
            115                 120                 125

Val Arg Asn Pro Gly Tyr Ala Phe Leu Ala Ala Ile Leu Gly Trp Met
130                 135                 140

Leu Gly Ser Asn Asn Gly Gln Arg Val Val Phe Thr Ile Leu Leu Leu
145                 150                 155                 160

Leu Val Ala Pro Ala Tyr Ser Phe Asn Cys Leu Gly Met Gly Asn Arg
                165                 170                 175

Asp Phe Ile Glu Gly Ala Ser Gly Ala Thr Trp Val Asp Leu Val Leu
            180                 185                 190

Glu Gly Asp Ser Cys Leu Thr Ile Met Ala Asn Asp Lys Pro Thr Leu
            195                 200                 205

Asp Val Arg Met Ile Asn Ile Glu Ala Val Gln Leu Ala Glu Val Arg
            210                 215                 220

Ser Tyr Cys Tyr His Ala Ser Val Thr Asp Ile Ser Thr Val Ala Arg
225                 230                 235                 240

Cys Pro Thr Thr Gly Glu Ala His Asn Lys Lys Arg Ala Asp Ser Ser
                245                 250                 255

Tyr Val Cys Lys Gln Gly Phe Thr Asp Arg Gly Trp Gly Asn Gly Cys
            260                 265                 270

Gly Leu Phe Gly Lys Gly Ser Ile Asp Thr Cys Ala Lys Phe Ser Cys
            275                 280                 285

Thr Ser Lys Ala Ile Gly Arg Thr Ile Gln Pro Glu Asn Ile Lys Tyr
            290                 295                 300

Glu Val Gly Ile Phe Val His Gly Thr Thr Thr Ser Glu Asn His Gly
305                 310                 315                 320

Asn Tyr Ser Ala Gln Val Gly Ala Ser Gln Ala Ala Lys Phe Thr Val
                325                 330                 335

Thr Pro Asn Ala Pro Ser Thr Thr Leu Lys Leu Gly Asp Tyr Gly Glu
            340                 345                 350

Val Thr Leu Asp Cys Glu Pro Arg Ser Gly Leu Asn Thr Glu Ala Phe
            355                 360                 365

Tyr Val Met Thr Val Gly Ser Lys Ser Phe Leu Val His Arg Glu Trp
            370                 375                 380

Phe His Asp Leu Ala Leu Pro Trp Thr Pro Pro Ser Ser Thr Ala Trp
385                 390                 395                 400

Arg Asn Arg Glu Leu Leu Met Glu Phe Glu Glu Ala His Ala Thr Lys
                405                 410                 415

Gln Ser Val Val Ala Leu Gly Ser Gln Glu Gly Gly Leu His Gln Ala
            420                 425                 430

Leu Ala Gly Ala Ile Val Val Glu Tyr Ser Asn Ser Val Lys Leu Thr
            435                 440                 445

Ser Gly His Leu Lys Cys Arg Leu Arg Met Asp Lys Leu Ala Leu Lys
            450                 455                 460

Gly Thr Thr Tyr Gly Met Cys Thr Glu Lys Phe Ser Phe Ala Lys Asn
465                 470                 475                 480
```

-continued

```
Pro Ala Asp Thr Gly His Gly Thr Val Val Ile Glu Leu Ser Tyr Ser
                485                 490                 495

Gly Ser Asp Gly Pro Cys Lys Ile Pro Ile Val Ser Val Ala Ser Leu
            500                 505                 510

Asn Asp Met Thr Pro Val Gly Arg Leu Val Thr Val Asn Pro Phe Val
        515                 520                 525

Ala Thr Ser Ser Ala Asn Ser Lys Val Leu Val Glu Met Glu Pro Pro
    530                 535                 540

Phe Gly Asp Ser Tyr Ile Val Val Gly Arg Gly Asp Lys Gln Ile Asn
545                 550                 555                 560

His His Trp His Lys Ala Gly Ser Thr Leu Gly Lys Ala Phe Ser Thr
                565                 570                 575

Thr Leu Lys Gly Ala Gln Arg Leu Ala Ala Leu Gly Asp Thr Ala Trp
            580                 585                 590

Asp Phe Gly Ser Ile Gly Gly Val Phe Asn Ser Ile Gly Lys Ala Val
        595                 600                 605

His Gln Val Phe Gly Gly Ala Phe Arg Thr Leu Phe Gly Gly Met Ser
    610                 615                 620

Trp Ile Thr Gln Gly Leu Met Gly Ala Leu Leu Leu Trp Met Gly Val
625                 630                 635                 640

Asn Ala Arg Asp Arg Ser Ile Ala Leu Ala Phe Leu Ala Thr Gly Gly
                645                 650                 655

Val Leu Val Phe Leu Ala Thr Asn Val His Ala
            660                 665

<210> SEQ ID NO 20
<211> LENGTH: 676
<212> TYPE: PRT
<213> ORGANISM: Artificial sequence
<220> FEATURE:
<223> OTHER INFORMATION: modified E protein

<400> SEQUENCE: 20

Met Lys Leu Ser Asn Phe Gln Gly Lys Leu Leu Met Thr Val Asn Asn
1               5                   10                  15

Thr Asp Ile Ala Asp Val Ile Val Ile Pro Thr Ser Lys Gly Glu Asn
            20                  25                  30

Arg Cys Trp Val Arg Ala Ile Asp Val G

```
Asp Phe Ile Glu Gly Ala Ser Gly Ala Thr Trp Val Asp Leu Val Leu
            180                 185                 190

Glu Gly Asp Ser Cys Leu Thr Ile Met Ala Asn Asp Lys Pro Thr Leu
        195                 200                 205

Asp Val Arg Met Ile Asn Ile Glu Ala Val Gln Leu Ala Glu Val Arg
    210                 215                 220

Ser Tyr Cys Tyr His Ala Ser Val Thr Asp Ile Ser Thr Val Ala Arg
225                 230                 235                 240

Cys Pro Thr Thr Gly Glu Ala His Asn Lys Lys Arg Ala Asp Ser Ser
                245                 250                 255

Tyr Val Cys Lys Gln Gly Phe Thr Asp Arg Gly Trp Gly Asn Gly Cys
            260                 265                 270

Gly Leu Phe Gly Lys Gly Ser Ile Asp Thr Cys Ala Lys Phe Ser Cys
        275                 280                 285

Thr Ser Lys Ala Ile Gly Arg Thr Ile Gln Pro Glu Asn Ile Lys Tyr
    290                 295                 300

Glu Val Gly Ile Phe Val His Gly Thr Thr Thr Ser Glu Asn His Gly
305                 310                 315                 320

Asn Tyr Ser Ala Gln Val Gly Ala Ser Gln Ala Ala Lys Phe Thr Val
                325                 330                 335

Thr Pro Asn Ala Pro Ser Thr Thr Leu Lys Leu Gly Asp Tyr Gly Glu
            340                 345                 350

Val Thr Leu Asp Cys Glu Pro Arg Ser Gly Leu Asn Thr Glu Ala Phe
        355                 360                 365

Tyr Val Met Thr Val Gly Ser Lys Ser Phe Leu Val His Arg Glu Trp
    370                 375                 380

Phe His Asp Leu Ala Leu Pro Trp Thr Pro Ser Ser Thr Ala Trp
385                 390                 395                 400

Arg Asn Arg Glu Leu Leu Met Glu Phe Glu Glu Ala His Ala Thr Lys
                405                 410                 415

Gln Ser Val Val Ala Leu Gly Ser Gln Glu Gly Gly Leu His Gln Ala
            420                 425                 430

Leu Ala Gly Ala Ile Val Val Glu Tyr Ser Asn Ser Val Lys Leu Thr
        435                 440                 445

Ser Gly His Leu Lys Cys Arg Leu Arg Met Asp Lys Leu Ala Leu Lys
    450                 455                 460

Gly Thr Thr Tyr Gly Met Cys Thr Glu Lys Phe Ser Phe Ala Lys Asn
465                 470                 475                 480

Pro Ala Asp Thr Gly His Gly Thr Val Val Ile Glu Leu Ser Tyr Ser
                485                 490                 495

Gly Ser Asp Gly Pro Cys Lys Ile Pro Ile Val Ser Val Ala Ser Leu
            500                 505                 510

Asn Asp Met Thr Pro Val Gly Arg Leu Val Thr Val Asn Pro Phe Val
        515                 520                 525

Ala Thr Ser Ser Ala Asn Ser Lys Val Leu Val Glu Met Glu Pro Pro
    530                 535                 540

Phe Gly Asp Ser Tyr Ile Val Val Gly Arg Gly Asp Lys Gln Ile Asn
545                 550                 555                 560

His His Trp His Lys Ala Gly Ser Thr Leu Gly Lys Ala Phe Ser Thr
                565                 570                 575

Thr Leu Lys Gly Ala Gln Arg Leu Ala Ala Leu Gly Asp Thr Ala Trp
            580                 585                 590
```

```
Asp Phe Gly Ser Ile Gly Gly Val Phe Asn Ser Ile Gly Lys Ala Val
        595                 600                 605

His Gln Val Phe Gly Gly Ala Phe Arg Thr Leu Phe Gly Gly Met Ser
610                 615                 620

Trp Ile Thr Gln Gly Leu Met Gly Ala Leu Leu Leu Trp Met Gly Val
625                 630                 635                 640

Asn Ala Arg Asp Arg Ser Ile Ala Leu Ala Phe Leu Ala Thr Gly Gly
                645                 650                 655

Val Leu Val Phe Leu Ala Thr Asn Val His Ala Asp Tyr Lys Asp Asp
                660                 665                 670

Asp Asp Lys Glx
        675

<210> SEQ ID NO 21
<211> LENGTH: 2028
<212> TYPE: DNA
<213> ORGANISM: Artificial sequence
<220> FEATURE:
<223> OTHER INFORMATION: codon modified E protein

<400> SEQUENCE: 21
atgaaactgt caaacttcca aggtaaactg ctgatgacag tgaacaacac agacatcgct      60
gacgtgatcg tgatccctac atcaaaaggt gaaaacagat gctgggtgag agctatcgac     120
gtgggttaca tgtgcgaaga cacaatcaca tacgaatgcc ctaaactgac aatgggtaac     180
gaccctgaag acgtggactg ctggtgcgac aaccaagaag tgtacgtgca atacggtaga     240
tgcacaagaa caagcacactc aaaaagatca agaagatcag tgtcagtgca acacacggt     300 gaatcatcac tggtgaacaa aaagaagct tggctggact caacaaaagc tacaagatac     360
ctgatgaaaa cagaaaactg gatcgtgaga accctggtt acgctttcct ggctgctatc     420
ctgggttgga tgctgggttc aaacaacggt caaagagtgg tgttcacaat cctgctgctg     480
ctggtggctc ctgcttactc attcaactgc ctgggtatgg gtaacagaga cttcatcgaa     540
ggtgcttcag gtgctacatg ggtggacctg gtgctggaag tgactcatg cctgacaatc     600 atggctaacg acaaacctac actggacgtg agaatgatca acatcgaagc tgtgcaactg     660
gctgaagtga atcatactg ctaccacgct tcagtgacag acatctcaac agtggctaga     720
tgccctacaa caggtgaagc tcacaacaaa aaaagagctg actcatcata cgtgtgcaaa     780
caaggtttca cagacagagg ttggggtaac ggttgcggtc tgttcggtaa aggttcaatc     840
gacacatgcg ctaaattctc atgcacatca aaagctatcg gtagaacaat ccaacctgaa     900
aacatcaaat acgaagtggg tatcttcgtg cacggtacaa caacatcaga aaaccacggt     960
aactactcag ctcaagtggg tgcttcacaa gctgctaaat tcacagtgac acctaacgct    1020
ccttcaacaa cactgaaact gggtgactac ggtgaagtga cactggactg cgaacctaga    1080
tcaggtctga cacagaagc tttctacgtg atgacagtgg ttcaaaatc attcctggtg    1140 cacagagaat ggttccacga cctggctctg ccttggacac tccttcatc aacagcttgg    1200 agaaacagag aactgctgat ggaattcgaa gaagctcacg ctacaaaaca atcagtggtg    1260
gctctgggtt cacaagaagg tggtctgcac aagctctgg ctggtgctat cgtggtggaa    1320
tactcaaact cagtgaaact gacatcaggt cacctgaaat gcagactgag aatggacaaa    1380
ctggctctga aggtacaac atacggtatg tgcacagaaa aattctcatt cgctaaaaac    1440
cctgctgaca caggtcacgg tacagtggtg atcgaactgt catactcagg ttcagacggt    1500
ccttgcaaaa tccctatcgt gtcagtggct tcactgaacg acatgacacc tgtgggtaga    1560
```

```
ctggtgacag tgaacccttt cgtggctaca tcatcagcta actcaaaagt gctggtggaa    1620
atggaacctc ctttcggtga ctcatacatc gtggtgggta gaggtgacaa acaaatcaac    1680
caccactggc acaaagctgg ttcaacactg gtaaagcttt ctcaacaac actgaaaggt     1740 gctcaaagac tggctgctct gggtgacaca gcttgggact tcggttcaat cggtggtgtg   1800
ttcaactcaa tcggtaaagc tgtgcaccaa gtgttcggtg gtgctttcag aacactgttc    1860
ggtggtatgt catggatcac acaaggtctg atgggtgctc tgctgctgtg gatgggtgtg   1920
aacgctagag acagatcaat cgctctggct ttcctggcta caggtggtgt gctggtgttc   1980
ctggctacaa acgtgcacgc tgactacaaa gacgacgacg acaaataa                 2028
```

<210> SEQ ID NO 22
<211> LENGTH: 524
<212> TYPE: PRT
<213> ORGANISM: Rabies virus

<400> SEQUENCE: 22

```
Met Ile Pro Gln Ala Leu Leu Phe Val Pro Leu Leu Val Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Lys Ser Leu His Ser Arg Val Phe Pro Asn Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Leu Gly Thr Ser Cys
        195                 200                 205

Asp Ile Phe Thr Asn Ser Arg Gly Lys Arg Ala Ser Lys Gly Ser Lys
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Leu Gln Thr Ser Asp Glu Thr Lys Trp Cys Ser
            260                 265                 270

Pro Asp Gln Leu Val Asn Leu His Asp Phe His Ser Asp Glu Ile Glu
        275                 280                 285
```

His Leu Val Val Glu Glu Leu Val Lys Lys Arg Glu Glu Cys Leu Asp
290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Ile Arg
            340                 345                 350

Thr Trp Asn Glu Ile Ile Pro Ser Lys Gly Cys Leu Arg Val Gly Gly
        355                 360                 365

Lys Cys His Pro His Val Asn Gly Val Phe Phe Asn Gly Ile Ile Leu
        370                 375                 380

Gly Pro Asp Gly His Val Leu Ile Pro Glu Met Gln Ser Ser Leu Leu
385                 390                 395                 400

His Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Lys Gln Ile Ser Gly
            435                 440                 445

Val Asp Leu Gly Leu Pro Asn Trp Gly Lys Tyr Val Leu Met Ser Ala
450                 455                 460

Gly Ala Leu Thr Val Leu Met Leu Thr Ile Phe Leu Val Thr Cys Cys
465                 470                 475                 480

Arg Lys Thr Asn Arg Ala Glu Ser Ile Gln His Ser Ser Gly Glu Thr
                485                 490                 495

Gly Arg Lys Val Ser Val Thr Ser Gln Asn Gly Arg Val Ile Ser Ser
            500                 505                 510

Trp Glu Ser Tyr Lys Ser Gly Gly Glu Thr Lys Leu
            515                 520

<210> SEQ ID NO 23
<211> LENGTH: 533
<212> TYPE: PRT
<213> ORGANISM: Artificial sequence
<220> FEATURE:
<223> OTHER INFORMATION: modified G protein

<400> SEQUENCE: 23

Met Ile Pro Gln Ala Leu Leu Phe Val Pro Leu Leu Val Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

```
Glu Ser Leu His Asn Pro Tyr Pro Asp Tyr His Trp Leu Arg Thr Val
130                 135                 140
Lys Thr Thr Lys Glu Ser Leu Val Ile Ile Ser Pro Ser Val Ala Asp
145                 150                 155                 160
Leu Asp Pro Tyr Asp Lys Ser Leu His Ser Arg Val Phe Pro Asn Gly
                165                 170                 175
Lys Cys Ser Gly Ile Thr Val Ser Ser Thr Tyr Cys Ser Thr Asn His
                180                 185                 190
Asp Tyr Thr Ile Trp Met Pro Glu Asn Pro Arg Leu Gly Thr Ser Cys
                195                 200                 205
Asp Ile Phe Thr Asn Ser Arg Gly Lys Arg Ala Ser Lys Gly Ser Lys
210                 215                 220
Thr Cys Gly Phe Val Asp Glu Arg Gly Leu Tyr Lys Ser Leu Lys Gly
225                 230                 235                 240
Ala Cys Lys Leu Lys Leu Cys Gly Val Leu Gly Leu Arg Leu Met Asp
                245                 250                 255
Gly Thr Trp Val Ala Leu Gln Thr Ser Asp Glu Thr Lys Trp Cys Ser
                260                 265                 270
Pro Asp Gln Leu Val Asn Leu His Asp Phe His Ser Asp Glu Ile Glu
                275                 280                 285
His Leu Val Val Glu Glu Leu Val Lys Lys Arg Glu Glu Cys Leu Asp
290                 295                 300
Ala Leu Glu Ser Ile Met Thr Thr Lys Ser Val Ser Phe Arg Arg Leu
305                 310                 315                 320
Ser His Leu Arg Lys Leu Val Pro Gly Phe Gly Lys Ala Tyr Thr Ile
                325                 330                 335
Phe Asn Lys Thr Leu Met Glu Ala Asp Ala His Tyr Lys Ser Ile Arg
                340                 345                 350
Thr Trp Asn Glu Ile Ile Pro Ser Lys Gly Cys Leu Arg Val Gly Gly
                355                 360                 365
Lys Cys His Pro His Val Asn Gly Val Phe Phe Asn Gly Ile Ile Leu
                370                 375                 380
Gly Pro Asp Gly His Val Leu Ile Pro Glu Met Gln Ser Ser Leu Leu
385                 390                 395                 400
His Gln His Met Glu Leu Leu Glu Ser Ser Val Ile Pro Leu Met His
                405                 410                 415
Pro Leu Ala Asp Pro Ser Thr Val Phe Lys Asp Gly Asp Glu Ala Glu
                420                 425                 430
Asp Phe Val Glu Val His Leu Pro Asp Val His Lys Gln Ile Ser Gly
                435                 440                 445
Val Asp Leu Gly Leu Pro Asn Trp Gly Lys Tyr Val Leu Met Ser Ala
450                 455                 460
Gly Ala Leu Thr Val Leu Met Leu Thr Ile Phe Leu Val Thr Cys Cys
465                 470                 475                 480
Arg Lys Thr Asn Arg Ala Glu Ser Ile Gln His Ser Ser Gly Glu Thr
                485                 490                 495
Gly Arg Lys Val Ser Val Thr Ser Gln Asn Gly Arg Val Ile Ser Ser
                500                 505                 510
Trp Glu Ser Tyr Lys Ser Gly Gly Glu Thr Lys Leu Asp Tyr Lys Asp
                515                 520                 525
Asp Asp Asp Lys Glx
530
```

<210> SEQ ID NO 24
<211> LENGTH: 1599
<212> TYPE: DNA
<213> ORGANISM: Artificial sequence
<220> FEATURE:
<223> OTHER INFORMATION: codon modified G protein

<400> SEQUENCE: 24

```
atgatccctc aagctctgct gttcgtgcct ctgctggtgt tctcactgtg cttcggtaaa      60
ttccctatct acacaatccc tgacaaactg ggtccttggt cacctatcga catccaccac     120
ctgtcatgcc ctaacaacct ggtggtggaa gacgaaggtt gcacaaacct gtcaggtttc     180
tcatacatgg aactgaaagt gggttacatc tcagctatca agtgaacgg tttcacatgc      240
acaggtgtgg tgacagaagc tgaaacatac acaaacttcg tgggttacgt gacaacaaca     300
ttcaaaagaa acacttcag acctacacct gacgcttgca gagctgctta caactggaaa      360
atggctggtg accctagata cgaagaatca ctgcacaacc cttaccctga ctaccactgg     420
ctgagaacag tgaaaacaac aaaagaatca ctggtgatca tctcaccttc agtggctgac     480
ctggacccttt acgacaaatc actgcactca gagtgttcc ctaacggtaa atgctcaggt     540
atcacagtgt catcaacata ctgctcaaca accacgact acacaatctg gatgcctgaa     600
accctagac tgggtacatc atgcgacatc ttcacaaact caagaggtaa aagagcttca     660
aaaggttcaa aacatgcgg tttcgtggac gaaagaggtc tgtacaaatc actgaaaggt     720
gcttgcaaac tgaaactgtg cggtgtgctg gtctgagac tgatggacgg tacatgggtg     780
gctctgcaaa catcagacga aacaaaatgg tgctcacctg accaactggt gaacctgcac     840
gacttccact cagacgaaat cgaacacctg gtggtggaag aactggtgaa aaaaagagaa     900
gaatgcctgg acgctctgga tcaatcatg acaacaaaat cagtgtcatt cagaagactg     960
tcacacctga aaaactggt gcctggtttc ggtaaagctt cacaatctt caacaaaaca    1020
ctgatggaag ctgacgctca ctacaaatca atcagaacat ggaacgaaat catcccttca    1080
aaaggttgcc tgagagtggg tggtaaatgc caccctcacg tgaacggtgt gttcttcaac    1140
ggtatcatcc tgggtcctga cggtcacgtg ctgatccctg aaatgcaatc atcactgctg    1200
caccaacaca tggaactgct ggaatcatca gtgatccctc tgatgcaccc tctggctgac    1260
ccttcaacag tgttcaaaga cggtgacgaa gctgaagact cgtggaagt gcacctgcct    1320
gacgtgcaca acaaatctc aggtgtggac ctgggtctgc taactgggg taaatacgtg    1380
ctgatgtcag ctggtgctct gacagtgctg atgctgacaa tcttcctggt gacatgctgc    1440
agaaaaacaa acagagctga atcaatccaa cactcatcag tgaaacagg tagaaaagtg    1500
tcagtgacat cacaaaacgg tagagtgatc tcatcatggg aatcatacaa atcaggtggt    1560
gaaacaaaac tggactacaa agacgacgac gacaaataa                           1599
```

<210> SEQ ID NO 25
<211> LENGTH: 669
<212> TYPE: PRT
<213> ORGANISM: West Nile virus

<400> SEQUENCE: 25

Met Val Thr Leu Ser Asn Phe Gln Gly Lys Val Met Met Thr Val Asn
1               5                   10                  15

Ala Thr Asp Val Thr Asp Ala Ile Thr Ile Pro Thr Ala Ala Gly Lys
            20                  25                  30

Asn Leu Cys Ile Val Arg Ala Met Asp Val Gly Tyr Leu Cys Glu Asp
        35                  40                  45

```
Thr Ile Thr Tyr Glu Cys Pro Val Leu Ala Ala Gly Asn Asp Pro Glu
     50                  55                  60

Asp Ile Asp Cys Trp Cys Thr Lys Ser Ser Val Tyr Val Arg Tyr Gly
 65              70                  75                  80

Arg Cys Thr Lys Thr Arg His Ser Arg Arg Ser Arg Arg Ser Leu Thr
                 85                  90                  95

Val Gln Thr His Gly Glu Ser Thr Leu Ala Asn Lys Lys Gly Ala Trp
            100                 105                 110

Leu Asp Ser Thr Lys Ala Thr Arg Tyr Leu Val Lys Thr Glu Ser Trp
        115                 120                 125

Ile Leu Arg Asn Pro Gly Tyr Ala Leu Val Ala Val Ile Gly Trp
        130                 135                 140

Met Leu Gly Ser Asn Thr Met Gln Arg Val Val Phe Ala Ile Leu Leu
145                 150                 155                 160

Leu Leu Val Ala Pro Ala Tyr Ser Phe Asn Cys Leu Gly Met Ser Asn
                165                 170                 175

Arg Asp Phe Leu Glu Gly Val Ser Gly Ala Thr Trp Val Asp Leu Val
            180                 185                 190

Leu Glu Gly Asp Ser Cys Val Thr Ile Met Ser Lys Asp Lys Pro Thr
        195                 200                 205

Ile Asp Val Lys Met Met Asn Met Glu Ala Ala Asn Leu Ala Asp Val
        210                 215                 220

Arg Ser Tyr Cys Tyr Leu Ala Ser Val Ser Asp Leu Ser Thr Lys Ala
225                 230                 235                 240

Ala Cys Pro Thr Met Gly Glu Ala His Asn Glu Lys Arg Ala Asp Pro
                245                 250                 255

Ala Phe Val Cys Lys Gln Gly Val Val Asp Arg Gly Trp Gly Asn Gly
            260                 265                 270

Cys Gly Leu Phe Gly Lys Gly Ser Ile Asp Thr Cys Ala Lys Phe Ala
        275                 280                 285

Cys Thr Thr Lys Ala Thr Gly Trp Ile Ile Gln Lys Glu Asn Ile Lys
290                 295                 300

Tyr Glu Val Ala Ile Phe Val His Gly Pro Thr Thr Val Glu Ser His
305                 310                 315                 320

Gly Asn Tyr Ser Thr Gln Ile Gly Ala Thr Gln Ala Gly Arg Phe Ser
                325                 330                 335

Ile Thr Pro Ser Ala Pro Ser Tyr Thr Leu Lys Leu Gly Glu Tyr Gly
            340                 345                 350

Glu Val Thr Val Asp Cys Glu Pro Arg Ser Gly Ile Asp Thr Ser Ala
        355                 360                 365

Tyr Tyr Val Met Ser Val Gly Ala Lys Ser Phe Leu Val His Arg Glu
370                 375                 380

Trp Phe Met Asp Leu Asn Leu Pro Trp Ser Ser Ala Gly Ser Thr Thr
385                 390                 395                 400

Trp Arg Asn Arg Glu Thr Leu Met Glu Phe Glu Pro His Ala Thr
                405                 410                 415

Lys Gln Ser Val Val Ala Leu Gly Ser Gln Glu Gly Ala Leu His Gln
            420                 425                 430

Ala Leu Ala Gly Ala Ile Pro Val Glu Phe Ser Ser Asn Thr Val Lys
        435                 440                 445

Leu Thr Ser Gly His Leu Lys Cys Arg Val Lys Met Glu Lys Leu Gln
        450                 455                 460
```

```
Leu Lys Gly Thr Thr Tyr Gly Val Cys Ser Lys Ala Phe Lys Phe Ala
465                 470                 475                 480

Arg Thr Pro Ala Asp Thr Gly His Gly Thr Val Val Leu Glu Leu Gln
                485                 490                 495

Tyr Thr Gly Lys Asp Gly Pro Cys Lys Val Pro Ile Ser Ser Val Ala
            500                 505                 510

Ser Leu Asn Asp Leu Thr Pro Val Gly Arg Leu Val Thr Val Asn Pro
        515                 520                 525

Phe Val Ser Val Ala Thr Ala Asn Ser Lys Val Leu Ile Glu Leu Glu
    530                 535                 540

Pro Pro Phe Gly Asp Ser Tyr Ile Val Val Gly Arg Gly Glu Gln Gln
545                 550                 555                 560

Ile Asn His His Trp His Lys Ser Gly Ser Ser Ile Gly Lys Ala Phe
                565                 570                 575

Thr Thr Thr Leu Arg Gly Ala Gln Arg Leu Ala Ala Leu Gly Asp Thr
                580                 585                 590

Ala Trp Asp Phe Gly Ser Val Gly Gly Val Phe Thr Ser Val Gly Lys
                595                 600                 605

Ala Ile His Gln Val Phe Gly Gly Ala Phe Arg Ser Leu Phe Gly Gly
                610                 615                 620

Met Ser Trp Ile Thr Gln Gly Leu Leu Gly Ala Leu Leu Leu Trp Met
625                 630                 635                 640

Gly Ile Asn Ala Arg Asp Arg Ser Ile Ala Met Thr Phe Leu Ala Val
                645                 650                 655

Gly Gly Val Leu Leu Phe Leu Ser Val Asn Val His Ala
                660                 665

<210> SEQ ID NO 26
<211> LENGTH: 677
<212> TYPE: PRT
<213> ORGANISM: Artificial sequence
<220> FEATURE:
<223> OTHER INFORMATION: modified fusion protein

<400> SEQUENCE: 26

Met Val Thr Leu Ser Asn Phe Gln Gly Lys Val Met Met Thr Val Asn
1               5                   10                  15

Ala Thr Asp Val Thr Asp Ala Ile Thr Ile Pro Thr Ala Ala Gly Lys
                20                  25                  30

Asn Leu Cys Ile Val Arg Ala Met Asp Val Gly Tyr Leu Cys Glu Asp
            35                  40                  45

Thr Ile Thr Tyr Glu Cys Pro Val Leu Ala Ala Gly Asn Asp Pro Glu
    50                  55                  60

Asp Ile Asp Cys Trp Cys Thr Lys Ser Ser Val Tyr Val Arg Tyr Gly
65                  70                  75                  80

Arg Cys Thr Lys Thr Arg His Ser Arg Arg Ser Arg Arg Ser Leu Thr
                85                  90                  95

Val Gln Thr His Gly Glu Ser Thr Leu Ala Asn Lys Lys Gly Ala Trp
                100                 105                 110

Leu Asp Ser Thr Lys Ala Thr Arg Tyr Leu Val Lys Thr Glu Ser Trp
            115                 120                 125

Ile Leu Arg Asn Pro Gly Tyr Ala Leu Val Ala Ala Val Ile Gly Trp
    130                 135                 140

Met Leu Gly Ser Asn Thr Met Gln Arg Val Val Phe Ala Ile Leu Leu
145                 150                 155                 160
```

```
Leu Leu Val Ala Pro Ala Tyr Ser Phe Asn Cys Leu Gly Met Ser Asn
                165                 170                 175

Arg Asp Phe Leu Glu Gly Val Ser Gly Ala Thr Trp Val Asp Leu Val
            180                 185                 190

Leu Glu Gly Asp Ser Cys Val Thr Ile Met Ser Lys Asp Lys Pro Thr
        195                 200                 205

Ile Asp Val Lys Met Met Asn Met Glu Ala Ala Asn Leu Ala Asp Val
210                 215                 220

Arg Ser Tyr Cys Tyr Leu Ala Ser Val Ser Asp Leu Ser Thr Lys Ala
225                 230                 235                 240

Ala Cys Pro Thr Met Gly Glu Ala His Asn Glu Lys Arg Ala Asp Pro
                245                 250                 255

Ala Phe Val Cys Lys Gln Gly Val Val Asp Arg Gly Trp Gly Asn Gly
            260                 265                 270

Cys Gly Leu Phe Gly Lys Gly Ser Ile Asp Thr Cys Ala Lys Phe Ala
        275                 280                 285

Cys Thr Thr Lys Ala Thr Gly Trp Ile Ile Gln Lys Glu Asn Ile Lys
290                 295                 300

Tyr Glu Val Ala Ile Phe Val His Gly Pro Thr Thr Val Glu Ser His
305                 310                 315                 320

Gly Asn Tyr Ser Thr Gln Ile Gly Ala Thr Gln Ala Gly Arg Phe Ser
                325                 330                 335

Ile Thr Pro Ser Ala Pro Ser Tyr Thr Leu Lys Leu Gly Glu Tyr Gly
            340                 345                 350

Glu Val Thr Val Asp Cys Glu Pro Arg Ser Gly Ile Asp Thr Ser Ala
        355                 360                 365

Tyr Tyr Val Met Ser Val Gly Ala Lys Ser Phe Leu Val His Arg Glu
370                 375                 380

Trp Phe Met Asp Leu Asn Leu Pro Trp Ser Ser Ala Gly Ser Thr Thr
385                 390                 395                 400

Trp Arg Asn Arg Glu Thr Leu Met Glu Phe Glu Glu Pro His Ala Thr
                405                 410                 415

Lys Gln Ser Val Val Ala Leu Gly Ser Gln Glu Gly Ala Leu His Gln
            420                 425                 430

Ala Leu Ala Gly Ala Ile Pro Val Glu Phe Ser Ser Asn Thr Val Lys
        435                 440                 445

Leu Thr Ser Gly His Leu Lys Cys Arg Val Lys Met Glu Lys Leu Gln
450                 455                 460

Leu Lys Gly Thr Thr Tyr Gly Val Cys Ser Lys Ala Phe Lys Phe Ala
465                 470                 475                 480

Arg Thr Pro Ala Asp Thr Gly His Gly Thr Val Val Leu Glu Leu Gln
                485                 490                 495

Tyr Thr Gly Lys Asp Gly Pro Cys Lys Val Pro Ile Ser Ser Val Ala
            500                 505                 510

Ser Leu Asn Asp Leu Thr Pro Val Gly Arg Leu Val Thr Val Asn Pro
        515                 520                 525

Phe Val Ser Val Ala Thr Ala Asn Ser Lys Val Leu Ile Glu Leu Glu
530                 535                 540

Pro Pro Phe Gly Asp Ser Tyr Ile Val Val Gly Arg Gly Glu Gln Gln
545                 550                 555                 560

Ile Asn His His Trp His Lys Ser Gly Ser Ser Ile Gly Lys Ala Phe
                565                 570                 575

Thr Thr Thr Leu Arg Gly Ala Gln Arg Leu Ala Ala Leu Gly Asp Thr
```

```
            580                 585                 590
Ala Trp Asp Phe Gly Ser Val Gly Gly Val Phe Thr Ser Val Gly Lys
                595                 600                 605

Ala Ile His Gln Val Phe Gly Ala Phe Arg Ser Leu Phe Gly Gly
            610                 615                 620

Met Ser Trp Ile Thr Gln Gly Leu Leu Gly Ala Leu Leu Leu Trp Met
625                 630                 635                 640

Gly Ile Asn Ala Arg Asp Arg Ser Ile Ala Met Thr Phe Leu Ala Val
                645                 650                 655

Gly Gly Val Leu Leu Phe Leu Ser Val Asn Val His Ala Asp Tyr Lys
                660                 665                 670

Asp Asp Asp Asp Lys
            675

<210> SEQ ID NO 27
<211> LENGTH: 2034
<212> TYPE: DNA
<213> ORGANISM: Artificial sequence
<220> FEATURE:
<223> OTHER INFORMATION: codon modified fusion protein

<400> SEQUENCE: 27
atggtgacac tgtcaaactt ccaaggtaaa gtgatgatga cagtgaacgc tacagacgtg      60
acagacgcta tcacaatccc tacagctgct ggtaaaaaac ctgcatcgt gagagctatg     120 gacgtgggtt acctgtgcga agacacaatc acatacgaat gccctgtgct ggctgctggt     180
aacgaccctg aagacatcga ctgctggtgc acaaaatcat cagtgtacgt gagatacggt     240
agatgcacaa aaacaagaca ctcaagaaga tcaagaagat cactgacagt gcaaacacac     300
ggtgaatcaa cactggctaa caaaaaaggt gcttggctgg actcaacaaa agctacaaga     360
tacctggtga aaacagaatc atggatcctg agaaaccctg ttacgctct ggtggctgct     420 gtgatcggtt ggatgctggg ttcaaacaca atgcaaagag tggtgttcgc tatcctgctg     480
ctgctggtgg ctcctgctta ctcattcaac tgcctgggta tgtcaaacag agacttcctg     540
gaaggtgtgt caggtgctac atgggtggac ctggtgctgg aaggtgactc atgcgtgaca     600
atcatgtcaa aagacaaacc tacaatcgac gtgaaaatga tgaacatgga agctgctaac     660
ctggctgacg tgagatcata ctgctacctg gcttcagtgt cagacctgtc aacaaaagct     720
gcttgcccta caatgggtga agctcacaac gaaaaaagag ctgaccctgc tttcgtgtgc     780
aaacaaggtg tggtggacag aggttggggt aacggttgcg gtctgttcgg taaaggttca     840
atcgacacat gcgctaaatt cgcttgcaca acaaaagcta caggttggat catccaaaaa     900
gaaaacatca aatacgaagt ggctatcttc gtgcacggtc ctacaacagt ggaatcacac     960
ggtaactact caacacaaat cggtgctaca caagctggta gattctcaat cacaccttca    1020
gctccttcat acacactgaa actgggtgaa tacggtgaag tgacagtgga ctgcgaacct    1080
agatcaggta tcgacacatc agcttactac gtgatgtcag tgggtgctaa atcattcctg    1140
gtgcacagag aatggttcat ggacctgaac ctgccttggt catcagctgg ttcaacaaca    1200
tggagaaaca gagaaacact gatggaattc gaagaacctc acgctacaaa acaatcagtg    1260
gtggctctgg gttcacaaga aggtgctctg caccaagctc tggctggtgc tatccctgtg    1320
gaattctcat caaacacagt gaaactgaca tcaggtcacc tgaaatgcag agtgaaaatg    1380
gaaaaactgc aactgaaagg tacaacatac ggtgtgtgct caaaagcttt caaattcgct    1440
agaacacctg ctgacacagg tcacggtaca gtggtgctgg aactgcaata cacaggtaaa    1500
```

```
gacggtcctt gcaaagtgcc tatctcatca gtggcttcac tgaacgacct gacacctgtg    1560
ggtagactgg tgacagtgaa ccctttcgtg tcagtggcta cagctaactc aaaagtgctg    1620
atcgaactgg aacctccttt cggtgactca tacatcgtgg tgggtagagg tgaacaacaa    1680
atcaaccacc actggcacaa atcaggttca tcaatcggta aagctttcac aacaacactg    1740
agaggtgctc aaagactggc tgctctgggt gacacagctt gggacttcgg ttcagtgggt    1800
ggtgtgttca catcagtggg taaagctatc caccaagtgt tcggtggtgc tttcagatca    1860
ctgttcggtg gtatgtcatg gatcacacaa ggtctgctgg gtgctctgct gctgtggatg    1920
ggtatcaacg ctagagacag atcaatcgct atgacattcc tggctgtggg tggtgtgctg    1980
ctgttcctgt cagtgaacgt gcacgctgac tacaaagacg acgacgacaa ataa         2034

<210> SEQ ID NO 28
<211> LENGTH: 1353
<212> TYPE: PRT
<213> ORGANISM: MERS coronavirus

<400> SEQUENCE: 28

Met Ile His Ser Val Phe Leu Leu Met Phe Leu Leu Thr Pro Thr Glu
1               5                   10                  15

Ser Tyr Val Asp Val Gly Pro Asp Ser Ile Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
```

```
                275                 280                 285
Thr Ile Lys Tyr Tyr Ser Ile Ile Pro His Ser Ile Arg Ser Ile Gln
290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Ser Phe Glu Ala
                355                 360                 365

Lys Pro Ser Gly Ser Val Val Glu Gln Ala Glu Gly Val Glu Cys Asp
370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
690                 695                 700
```

-continued

```
Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760                 765

Gln Val Asp Gln Leu Asn Ser Ser Tyr Phe Lys Leu Ser Ile Pro Thr
770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe His Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110
```

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
    1340                1345                1350

<210> SEQ ID NO 29
<211> LENGTH: 1361
<212> TYPE: PRT
<213> ORGANISM: Artificial sequence
<220> FEATURE:
<223> OTHER INFORMATION: modified spike G protein

<400> SEQUENCE: 29

Met Ile His Ser Val Phe Leu Leu Met Phe Leu Leu Thr Pro Thr Glu
1               5                   10                  15

Ser Tyr Val Asp Val Gly Pro Asp Ser Ile Lys Ser Ala Cys Ile Glu
                20                  25                  30

Val Asp Ile Gln Gln Thr Phe Phe Asp Lys Thr Trp Pro Arg Pro Ile
            35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

```
Ala Asn Gly Phe Val Val Arg Ile Gly Ala Ala Ala Asn Ser Thr Gly
            115                 120                 125

Thr Val Ile Ile Ser Pro Ser Thr Ser Ala Thr Ile Arg Lys Ile Tyr
130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
```

```
              530                 535                 540
Leu Ser Pro Leu Glu Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
        610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
                755                 760                 765

Gln Val Asp Gln Leu Asn Ser Ser Tyr Phe Lys Leu Ser Ile Pro Thr
                770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
                835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
                915                 920                 925

Val Ala Gly Tyr Lys Val Leu Pro Pro Leu Met Asp Val Asn Met Glu
                930                 935                 940

Ala Ala Tyr Thr Ser Ser Leu Leu Gly Ser Ile Ala Gly Val Gly Trp
945                 950                 955                 960
```

```
Thr Ala Gly Leu Ser Ser Phe Ala Ala Ile Pro Phe Ala Gln Ser Ile
                965                 970                 975
Phe Tyr Arg Leu Asn Gly Val Gly Ile Thr Gln Gln Val Leu Ser Glu
                980                 985                 990
Asn Gln Lys Leu Ile Ala Asn Lys  Phe Asn Gln Ala Leu  Gly Ala Met
            995                 1000                1005
Gln Thr Gly Phe Thr Thr Thr Asn Glu Ala Phe His  Lys Val Gln
        1010                1015                 1020
Asp Ala Val Asn Asn Ala  Gln Ala Leu Ser Lys  Leu Ala Ser
        1025                1030                1035
Glu Leu Ser Asn Thr Phe Gly  Ala Ile Ser Ala Ser  Ile Gly Asp
        1040                1045                1050
Ile Ile Gln Arg Leu Asp Val  Leu Glu Gln Asp Ala  Gln Ile Asp
        1055                1060                1065
Arg Leu Ile Asn Gly Arg Leu  Thr Thr Leu Asn Ala  Phe Val Ala
        1070                1075                1080
Gln Gln Leu Val Arg Ser Glu  Ser Ala Ala Leu Ser  Ala Gln Leu
        1085                1090                1095
Ala Lys Asp Lys Val Asn Glu  Cys Val Lys Ala Gln  Ser Lys Arg
        1100                1105                1110
Ser Gly Phe Cys Gly Gln Gly  Thr His Ile Val Ser  Phe Val Val
        1115                1120                1125
Asn Ala Pro Asn Gly Leu Tyr  Phe Met His Val Gly  Tyr Tyr Pro
        1130                1135                1140
Ser Asn His Ile Glu Val Val  Ser Ala Tyr Gly Leu  Cys Asp Ala
        1145                1150                1155
Ala Asn Pro Thr Asn Cys Ile  Ala Pro Val Asn Gly  Tyr Phe Ile
        1160                1165                1170
Lys Thr Asn Asn Thr Arg Ile  Val Asp Glu Trp Ser  Tyr Thr Gly
        1175                1180                1185
Ser Ser Phe Tyr Ala Pro Glu  Pro Ile Thr Ser Leu  Asn Thr Lys
        1190                1195                1200
Tyr Val Ala Pro Gln Val Thr  Tyr Gln Asn Ile Ser  Thr Asn Leu
        1205                1210                1215
Pro Pro Pro Leu Leu Gly Asn  Ser Thr Gly Ile Asp  Phe Gln Asp
        1220                1225                1230
Glu Leu Asp Glu Phe Phe Lys  Asn Val Ser Thr Ser  Ile Pro Asn
        1235                1240                1245
Phe Gly Ser Leu Thr Gln Ile  Asn Thr Thr Leu Leu  Asp Leu Thr
        1250                1255                1260
Tyr Glu Met Leu Ser Leu Gln  Gln Val Val Lys Ala  Leu Asn Glu
        1265                1270                1275
Ser Tyr Ile Asp Leu Lys Glu  Leu Gly Asn Tyr Thr  Tyr Tyr Asn
        1280                1285                1290
Lys Trp Pro Trp Tyr Ile Trp  Leu Gly Phe Ile Ala  Gly Leu Val
        1295                1300                1305
Ala Leu Ala Leu Cys Val Phe  Phe Ile Leu Cys Cys  Thr Gly Cys
        1310                1315                1320
Gly Thr Asn Cys Met Gly Lys  Leu Lys Cys Asn Arg  Cys Cys Asp
        1325                1330                1335
Arg Tyr Glu Glu Tyr Asp Leu  Glu Pro His Lys Val  His Val His
        1340                1345                1350
```

Asp Tyr Lys Asp Asp Asp Lys
    1355            1360

<210> SEQ ID NO 30
<211> LENGTH: 4086
<212> TYPE: DNA
<213> ORGANISM: Artificial sequence
<220> FEATURE:
<223> OTHER INFORMATION: codon modified spike G protein

<400> SEQUENCE: 30

| | | | | | |
|---|---|---|---|---|---|
| atgatccact | cagtgttcct | gctgatgttc | ctgctgacac | ctacagaatc | atacgtggac | 60 |
| gtgggtcctg | actcaatcaa | atcagcttgc | atcgaagtgg | acatccaaca | acattcttc | 120 |
| gacaaaacat | ggcctagacc | tatcgacgtg | tcaaaagctg | acggtatcat | ctaccctcaa | 180 |
| ggtagaacat | actcaaacat | cacaatcaca | taccaaggtc | tgttcccttt | ccaaggtgac | 240 |
| cacggtgaca | tgtacgtgta | ctcagctggt | cacgctacag | gtacaacacc | tcaaaaactg | 300 |
| ttcgtggcta | actactcaca | agacgtgaaa | caattcgcta | cggtttcgt | ggtgagaatc | 360 |
| ggtgctgctg | ctaactcaac | aggtacagtg | atcatctcac | cttcaacatc | agctacaatc | 420 |
| agaaaaatct | accctgcttt | catgctgggt | tcatcagtgg | gtaacttctc | agacggtaaa | 480 |
| atgggtagat | tcttcaacca | cactgctgtg | ctgctgcctg | acggttgcgg | tacactgctg | 540 |
| agagctttct | actgcatcct | ggaacctaga | tcaggtaacc | actgccctgc | tgtaactca | 600 |
| tacacatcat | cgctacata | ccacacacct | gctacagact | gctcagacgg | taactacaac | 660 |
| agaaacgctt | cactgaactc | attcaaagaa | tacttcaacc | tgagaaactg | cacattcatg | 720 |
| tacacataca | acatcacaga | agacgaaatc | ctggaatggt | tcggtatcac | acaaacagct | 780 |
| caaggtgtgc | acctgttctc | atcaagatac | gtggacctgt | acggtggtaa | catgttccaa | 840 |
| ttcgctacac | tgcctgtgta | cgacacaatc | aaatactact | caatcatccc | tcactcaatc | 900 |
| agatcaatcc | aatcagacag | aaaagcttgg | gctgctttct | acgtgtacaa | actgcaacct | 960 |
| ctgacattcc | tgctggactt | ctcagtggac | ggttacatca | gaagagctat | cgactgcggt | 1020 |
| ttcaacgacc | tgtcacaact | gcactgctca | tacgaatcat | tcgacgtgga | atcaggtgtg | 1080 |
| tactcagtgt | catcattcga | agctaaacct | tcaggttcag | tggtggaaca | agctgaaggt | 1140 |
| gtggaatgcg | acttctcacc | tctgctgtca | ggtacacctc | tcaagtgta | aacttcaaa | 1200 |
| agactggtgt | tcaaaactg | caactacaac | ctgacaaaac | tgctgtcact | gttctcagtg | 1260 |
| aacgacttca | catgctcaca | aatctcacct | gctgctatcg | cttcaaactg | ctactcatca | 1320 |
| ctgatcctgg | actacttctc | atacccctg | tcaatgaaat | cagacctgtc | agtgtcatca | 1380 |
| gctggtccta | tctcacaatt | caactacaaa | caatcattct | caaaccctac | atgcctgatc | 1440 |
| ctggctacag | tgcctcacaa | cctgacaaca | atcacaaaac | tctgaaata | tcatacatc | 1500 |
| aacaaatgct | caagactgct | gtcagacgac | agaacagaag | tgcctcaact | ggtgaacgct | 1560 |
| aaccaatact | caccttgcgt | gtcaatcgtg | ccttcaacag | tgggaagaa | cggtgactac | 1620 |
| tacagaaaac | aactgtcacc | tctggaaggt | ggtggttggc | tggtggcttc | aggttcaaca | 1680 |
| gtggctatga | cagaacaact | gcaaatgggt | ttcggtatca | cagtgcaata | cggtacagac | 1740 |
| acaaactcag | tgtgccctaa | actggaattc | gctaacgaca | caaaaatcgc | ttcacaactg | 1800 |
| ggtaactgcg | tggaatactc | actgtacggt | gtgtcaggta | gaggtgtgtt | ccaaaactgc | 1860 |
| acagctgtgg | gtgtgagaca | acaaagattc | gtgtacgacg | cttaccaaaa | cctggtgggt | 1920 |
| tactactcag | acgacggtaa | ctactactgc | ctgagagctt | gcgtgtcagt | gcctgtgtca | 1980 |

| | |
|---|---|
| gtgatctacg acaaagaaac aaaaacacac gctacactgt tcggttcagt ggcttgcgaa | 2040 |
| cacatctcat caacaatgtc acaatactca agatcaacaa gatcaatgct gaaaagaaga | 2100 |
| gactcaacat acggtcctct gcaaacacct gtggttgcg tgctgggtct ggtgaactca | 2160 |
| tcactgttcg tggaagactg caaactgcct ctgggtcaat cactgtgcgc tctgcctgac | 2220 |
| acaccttcaa cactgacacc tagatcagtg agatcagtgc ctggtgaaat gagactggct | 2280 |
| tcaatcgctt tcaaccaccc tatccaagtg gaccaactga actcatcata cttcaaactg | 2340 |
| tcaatcccta caaacttctc attcggtgtg acacaagaat acatccaaac aacaatccaa | 2400 |
| aaagtgacag tggactgcaa acaatacgtg tgcaacggtt tccaaaaatg cgaacaactg | 2460 |
| ctgagagaat acggtcaatt ctgctcaaaa atcaaccaag ctctgcacgg tgctaacctg | 2520 |
| agacaagacg actcagtgag aaacctgttc gcttcagtga atcatcaca atcatcacct | 2580 |
| atcatccctg gtttcggtgg tgacttcaac ctgacactgc tggaacctgt gtcaatctca | 2640 |
| acaggttcaa gatcagctag atcagctatc gaagacctgc tgttcgacaa agtgacaatc | 2700 |
| gctgaccctg gttacatgca aggttacgac gactgcatgc aacaaggtcc tgcttcagct | 2760 |
| agagacctga tctgcgctca atacgtggct ggttacaaag tgctgcctcc tctgatggac | 2820 |
| gtgaacatgg aagctgctta cacatcatca ctgctgggtt caatcgctgg tgtgggttgg | 2880 |
| acagctggtc tgtcatcatt cgctgctatc cctttcgctc aatcaatctt ctacagactg | 2940 |
| aacggtgtgg gtatcacaca acaagtgctg tcagaaaacc aaaaactgat cgctaacaaa | 3000 |
| ttcaaccaag ctctgggtgc tatgcaaaca ggtttcacaa caacaaacga agctttccac | 3060 |
| aaagtgcaag acgctgtgaa caacaacgct caagctctgt caaaactggc ttcagaactg | 3120 |
| tcaaacacat tcggtgctat ctcagcttca atcggtgaca tcatccaaag actggacgtg | 3180 |
| ctggaacaag acgctcaaat cgacagactg atcaacggta gactgacaac actgaacgct | 3240 |
| ttcgtggctc aacaactggt gagatcagaa tcagctgctc tgtcagctca actggctaaa | 3300 |
| gacaaagtga cgaatgcgt gaaagctcaa tcaaaaagat caggtttctg cggtcaaggt | 3360 |
| acacacatcg tgtcattcgt ggtgaacgct cctaacggtc tgtacttcat gcacgtgggt | 3420 |
| tactacccttt caaccacat cgaagtggtg tcagcttacg gtctgtgcga cgctgctaac | 3480 |
| cctacaaact gcatcgctcc tgtgaacggt tacttcatca aaacaaacaa cacaagaatc | 3540 |
| gtggacgaat ggtcatacac aggttcatca ttctacgctc ctgaacctat cacatcactg | 3600 |
| aacacaaaat acgtggctcc tcaagtgaca taccaaaaca tctcaacaaa cctgcctcct | 3660 |
| cctctgctgg gtaactcaac aggtatcgac ttccagacg aactggacga attcttcaaa | 3720 |
| aacgtgtcaa catcaatccc taacttcggt tcactgacac aaatcaacac aacactgctg | 3780 |
| gacctgacat acgaaatgct gtcactgcaa caagtggtga agctctgaa cgaatcatac | 3840 |
| atcgacctga agaactggg taactacaca tactacaaca atggccttg gtacatctgg | 3900 |
| ctgggttttca tcgctggtct ggtggctctg gctctgtgcg tgttcttcat cctgtgctgc | 3960 |
| acaggttgcg gtacaaactg catgggtaaa ctgaaatgca acagatgctg cgacagatac | 4020 |
| gaagaatacg acctggaacc tcacaaagtg cacgtgcacg actacaaaga cgacgacgac | 4080 |
| aaataa | 4086 |

<210> SEQ ID NO 31
<211> LENGTH: 969
<212> TYPE: PRT
<213> ORGANISM: Picornaviridae Aphthovirus

<400> SEQUENCE: 31

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
            35                  40                  45

Glu Gly Ser Thr Asp Thr Thr Ser Thr His Thr Thr Asn Thr Gln Asn
50              55                      60

Asn Asp Trp Phe Ser Arg Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
                100                 105                 110

Ser Ser Val Gly Val Thr Tyr Gly Tyr Ala Val Thr Glu Asp Ala Val
                115                 120                 125

Ser Gly Pro Asn Thr Ser Gly Leu Glu Thr Arg Val Thr Gln Ala Glu
                130                 135                 140

Arg Phe Phe Lys Lys His Leu Phe Asp Trp Thr Pro Asn Leu Ala Phe
145                 150                 155                 160

Gly His Cys His Tyr Leu Glu Leu Pro Thr Glu His Lys Gly Val Tyr
                165                 170                 175

Gly Ser Leu Met Asp Ser Tyr Ala Tyr Met Arg Asn Gly Trp Asp Ile
                180                 185                 190

Glu Val Thr Ala Val Gly Asn Gln Phe Asn Gly Gly Cys Leu Leu Val
                195                 200                 205

Ala Leu Val Pro Glu Leu Lys Glu Leu Asp Thr Arg Gln Lys Tyr Gln
210                 215                 220

Leu Thr Leu Phe Pro His Gln Phe Ile Asn Pro Arg Thr Asn Met Thr
225                 230                 235                 240

Ala His Ile Asn Val Pro Phe Val Gly Val Asn Arg Tyr Asp Gln Tyr
                245                 250                 255

Ala Leu His Lys Pro Trp Thr Leu Val Val Met Val Val Ala Pro Leu
                260                 265                 270

Thr Val Lys Thr Gly Gly Ser Glu Gln Ile Lys Val Tyr Met Asn Ala
                275                 280                 285

Ala Pro Thr Tyr Val His Val Ala Gly Glu Leu Pro Ser Lys Glu Gly
                290                 295                 300

Ile Val Pro Val Ala Cys Ala Asp Gly Tyr Gly Asn Met Val Thr Thr
305                 310                 315                 320

Asp Pro Lys Thr Ala Asp Pro Val Tyr Gly Lys Val Phe Asn Pro Pro
                325                 330                 335

Arg Thr Asn Leu Pro Gly Arg Phe Thr Asn Phe Leu Asp Val Ala Glu
                340                 345                 350

Ala Cys Pro Thr Phe Leu Arg Phe Gly Glu Val Pro Phe Val Lys Thr
                355                 360                 365

Val Asn Ser Gly Asp Arg Leu Leu Ala Lys Phe Asp Val Ser Leu Ala
                370                 375                 380

Ala Gly His Met Ser Asn Thr Tyr Leu Ala Gly Leu Ala Gln Tyr Tyr
385                 390                 395                 400

Thr Gln Tyr Ser Gly Thr Met Asn Ile His Phe Met Phe Thr Gly Pro
                405                 410                 415

-continued

```
Thr Asp Ala Lys Ala Arg Tyr Met Val Ala Tyr Val Pro Pro Gly Met
            420                 425                 430

Thr Pro Pro Thr Asp Pro Glu Arg Ala Ala His Cys Ile His Ser Glu
        435                 440                 445

Trp Asp Thr Gly Leu Asn Ser Lys Phe Thr Phe Ser Ile Pro Tyr Leu
    450                 455                 460

Ser Ala Ala Asp Tyr Ala Tyr Thr Ala Ser Asp Val Ala Glu Ala Thr
465                 470                 475                 480

Ser Val Gln Gly Trp Val Cys Ile Tyr Gln Ile Thr His Gly Lys Ala
                485                 490                 495

Glu Gly Asp Ala Leu Val Ser Ala Ser Ala Gly Lys Asp Phe Glu
            500                 505                 510

Phe Arg Leu Pro Val Asp Ala Arg Gln Gln Thr Thr Thr Gly Glu
        515                 520                 525

Ser Ala Asp Pro Val Thr Thr Thr Val Glu Asn Tyr Gly Gly Glu Thr
    530                 535                 540

Gln Thr Ala Arg Arg Leu His Thr Asp Val Ala Phe Val Leu Asp Arg
545                 550                 555                 560

Phe Val Lys Phe Thr Pro Lys Asn Thr Gln Thr Leu Asp Leu Met Gln
                565                 570                 575

Ile Pro Ser His Thr Leu Val Gly Ala Leu Leu Arg Ser Ala Thr Tyr
            580                 585                 590

Tyr Phe Ser Asp Leu Glu Ile Ala Leu Val His Thr Gly Pro Val Thr
        595                 600                 605

Trp Val Pro Asn Gly Ala Pro Lys Thr Ala Leu Asp Asn Gln Thr Asn
    610                 615                 620

Pro Thr Ala Tyr His Lys Gln Pro Ile Thr Arg Leu Ala Leu Pro Tyr
625                 630                 635                 640

Thr Ala Pro His Arg Val Leu Ala Thr Val Tyr Asn Gly Lys Thr Thr
                645                 650                 655

Tyr Gly Glu Glu Pro Thr Met Arg Gly Asp Arg Ala Val Leu Ala Ser
            660                 665                 670

Lys Val Asn Lys Gln Leu Pro Thr Ser Phe Asn Tyr Gly Ala Val Lys
        675                 680                 685

Ala Glu Asn Ile Thr Glu Met Leu Ile Arg Ile Lys Arg Ala Glu Thr
    690                 695                 700

Tyr Cys Pro Arg Pro Leu Leu Ala Leu Asp Thr Gln Asp Arg Arg
705                 710                 715                 720

Lys Gln Glu Ile Ile Ala Pro Glu Lys Gln Leu Leu Asn Phe Asp Leu
                725                 730                 735

Leu Lys Leu Ala Gly Asp Val Glu Ser Asn Pro Gly Pro Phe Phe Phe
            740                 745                 750

Ser Asp Val Arg Ser Gly Ala Pro Pro Thr Asp Leu Gln Lys Met Val
        755                 760                 765

Met Gly Asn Thr Lys Pro Val Glu Leu Ile Leu Asp Gly Lys Thr Val
    770                 775                 780

Ala Ile Cys Cys Ala Thr Gly Val Phe Gly Thr Ala Tyr Leu Val Pro
785                 790                 795                 800

Arg His Leu Phe Ala Glu Lys Tyr Asp Lys Ile Met Leu Asp Gly Arg
                805                 810                 815

Ala Met Thr Asp Ser Asp Tyr Arg Val Phe Glu Phe Glu Ile Lys Val
            820                 825                 830

Lys Gly Gln Asp Met Leu Ser Asp Ala Ala Leu Met Val Leu His Arg
```

```
                    835                 840                 845
Gly Asn Arg Val Arg Asp Ile Thr Lys His Phe Arg Asp Val Ala Arg
            850                 855                 860
Met Lys Lys Gly Thr Pro Val Val Gly Val Ile Asn Asn Ala Asp Val
865                 870                 875                 880
Gly Arg Leu Ile Phe Ser Gly Glu Ala Leu Thr Tyr Lys Asp Ile Val
                885                 890                 895
Val Cys Met Asp Gly Asp Thr Met Pro Gly Leu Phe Ala Tyr Lys Ala
                900                 905                 910
Ala Thr Lys Ala Gly Tyr Cys Gly Gly Ala Val Leu Ala Lys Asp Gly
            915                 920                 925
Ala Glu Thr Phe Ile Val Gly Thr His Ser Ala Gly Gly Asn Gly Val
        930                 935                 940
Gly Tyr Cys Ser Cys Val Ser Arg Ser Met Leu Leu Lys Met Lys Ala
945                 950                 955                 960
His Ile Asp Pro Glu Pro His His Glu
                965
```

<210> SEQ ID NO 32
<211> LENGTH: 978
<212> TYPE: PRT
<213> ORGANISM: Artificial sequence
<220> FEATURE:
<223> OTHER INFORMATION: modified fusion protein

<400> SEQUENCE: 32

```
Met Asp Tyr Lys Asp Asp Asp Lys Gly Ala Gly Gln Ser Ser Pro
1               5                   10                  15
Ala Thr Gly Ser Gln Asn Gln Ser Gly Asn Thr Gly Ser Ile Ile Asn
            20                  25                  30
Asn Tyr Tyr Met Gln Gln Tyr Gln Asn Ser Met Asp Thr Gln Leu Gly
        35                  40                  45
Asp Asn Ala Ile Ser Gly Gly Ser Asn Glu Gly Ser Thr Asp Thr Thr
    50                  55                  60
Ser Thr His Thr Thr Asn Thr Gln Asn Asn Asp Trp Phe Ser Arg Leu
65                  70                  75                  80
Ala Ser Ser Ala Phe Ser Gly Leu Phe Gly Ala Leu Leu Ala Asp Lys
                85                  90                  95
Lys Thr Glu Glu Thr Thr Leu Leu Glu Asp Arg Ile Leu Thr Thr Arg
            100                 105                 110
Asn Gly His Thr Thr Ser Thr Thr Gln Ser Ser Val Gly Val Thr Tyr
        115                 120                 125
Gly Tyr Ala Val Thr Glu Asp Ala Val Ser Gly Pro Asn Thr Ser Gly
    130                 135                 140
Leu Glu Thr Arg Val Thr Gln Ala Glu Arg Phe Phe Lys Lys His Leu
145                 150                 155                 160
Phe Asp Trp Thr Pro Asn Leu Ala Phe Gly His Cys His Tyr Leu Glu
                165                 170                 175
Leu Pro Thr Glu His Lys Gly Val Tyr Gly Ser Leu Met Asp Ser Tyr
            180                 185                 190
Ala Tyr Met Arg Asn Gly Trp Asp Ile Glu Val Thr Ala Val Gly Asn
        195                 200                 205
Gln Phe Asn Gly Gly Cys Leu Leu Val Ala Leu Val Pro Glu Leu Lys
    210                 215                 220
Glu Leu Asp Thr Arg Gln Lys Tyr Gln Leu Thr Leu Phe Pro His Gln
```

```
            225                 230                 235                 240
        Phe Ile Asn Pro Arg Thr Asn Met Thr Ala His Ile Asn Val Pro Phe
                            245                 250                 255
        Val Gly Val Asn Arg Tyr Asp Gln Tyr Ala Leu His Lys Pro Trp Thr
                            260                 265                 270
        Leu Val Val Met Val Val Ala Pro Leu Thr Val Lys Thr Gly Gly Ser
                        275                 280                 285
        Glu Gln Ile Lys Val Tyr Met Asn Ala Ala Pro Thr Tyr Val His Val
            290                 295                 300
        Ala Gly Glu Leu Pro Ser Lys Glu Gly Ile Val Pro Val Ala Cys Ala
        305                 310                 315                 320
        Asp Gly Tyr Gly Asn Met Val Thr Thr Asp Pro Lys Thr Ala Asp Pro
                            325                 330                 335
        Val Tyr Gly Lys Val Phe Asn Pro Pro Arg Thr Asn Leu Pro Gly Arg
                        340                 345                 350
        Phe Thr Asn Phe Leu Asp Val Ala Glu Ala Cys Pro Thr Phe Leu Arg
                        355                 360                 365
        Phe Gly Glu Val Pro Phe Val Lys Thr Val Asn Ser Gly Asp Arg Leu
                    370                 375                 380
        Leu Ala Lys Phe Asp Val Ser Leu Ala Ala Gly His Met Ser Asn Thr
        385                 390                 395                 400
        Tyr Leu Ala Gly Leu Ala Gln Tyr Tyr Thr Gln Tyr Ser Gly Thr Met
                        405                 410                 415
        Asn Ile His Phe Met Phe Thr Gly Pro Thr Asp Ala Lys Ala Arg Tyr
                        420                 425                 430
        Met Val Ala Tyr Val Pro Pro Gly Met Thr Pro Thr Asp Pro Glu
                    435                 440                 445
        Arg Ala Ala His Cys Ile His Ser Glu Trp Asp Thr Gly Leu Asn Ser
                    450                 455                 460
        Lys Phe Thr Phe Ser Ile Pro Tyr Leu Ser Ala Ala Asp Tyr Ala Tyr
        465                 470                 475                 480
        Thr Ala Ser Asp Val Ala Glu Ala Thr Ser Val Gln Gly Trp Val Cys
                        485                 490                 495
        Ile Tyr Gln Ile Thr His Gly Lys Ala Glu Gly Asp Ala Leu Val Val
                    500                 505                 510
        Ser Ala Ser Ala Gly Lys Asp Phe Glu Phe Arg Leu Pro Val Asp Ala
                    515                 520                 525
        Arg Gln Gln Thr Thr Thr Thr Gly Glu Ser Ala Asp Pro Val Thr Thr
            530                 535                 540
        Thr Val Glu Asn Tyr Gly Gly Glu Thr Gln Thr Ala Arg Arg Leu His
        545                 550                 555                 560
        Thr Asp Val Ala Phe Val Leu Asp Arg Phe Val Lys Phe Thr Pro Lys
                        565                 570                 575
        Asn Thr Gln Thr Leu Asp Leu Met Gln Ile Pro Ser His Thr Leu Val
                    580                 585                 590
        Gly Ala Leu Leu Arg Ser Ala Thr Tyr Tyr Phe Ser Asp Leu Glu Ile
                    595                 600                 605
        Ala Leu Val His Thr Gly Pro Val Thr Trp Val Pro Asn Gly Ala Pro
                    610                 615                 620
        Lys Thr Ala Leu Asp Asn Gln Thr Asn Pro Thr Ala Tyr His Lys Gln
        625                 630                 635                 640
        Pro Ile Thr Arg Leu Ala Leu Pro Tyr Thr Ala Pro His Arg Val Leu
                        645                 650                 655
```

```
Ala Thr Val Tyr Asn Gly Lys Thr Thr Tyr Gly Glu Glu Pro Thr Met
            660                 665                 670
Arg Gly Asp Arg Ala Val Leu Ala Ser Lys Val Asn Lys Gln Leu Pro
        675                 680                 685
Thr Ser Phe Asn Tyr Gly Ala Val Lys Ala Glu Asn Ile Thr Glu Met
    690                 695                 700
Leu Ile Arg Ile Lys Arg Ala Glu Thr Tyr Cys Pro Arg Pro Leu Leu
705                 710                 715                 720
Ala Leu Asp Thr Thr Gln Asp Arg Arg Lys Gln Ile Ile Ala Pro
                725                 730                 735
Glu Lys Gln Leu Leu Asn Phe Asp Leu Leu Lys Leu Ala Gly Asp Val
            740                 745                 750
Glu Ser Asn Pro Gly Pro Phe Phe Ser Asp Val Arg Ser Gly Ala
        755                 760                 765
Pro Pro Thr Asp Leu Gln Lys Met Val Met Gly Asn Thr Lys Pro Val
    770                 775                 780
Glu Leu Ile Leu Asp Gly Lys Thr Val Ala Ile Cys Cys Ala Thr Gly
785                 790                 795                 800
Val Phe Gly Thr Ala Tyr Leu Val Pro Arg His Leu Phe Ala Glu Lys
            805                 810                 815
Tyr Asp Lys Ile Met Leu Asp Gly Arg Ala Met Thr Asp Ser Asp Tyr
        820                 825                 830
Arg Val Phe Glu Phe Glu Ile Lys Val Lys Gly Gln Asp Met Leu Ser
    835                 840                 845
Asp Ala Ala Leu Met Val Leu His Arg Gly Asn Arg Val Arg Asp Ile
850                 855                 860
Thr Lys His Phe Arg Asp Val Ala Arg Met Lys Lys Gly Thr Pro Val
865                 870                 875                 880
Val Gly Val Ile Asn Asn Ala Asp Val Gly Arg Leu Ile Phe Ser Gly
            885                 890                 895
Glu Ala Leu Thr Tyr Lys Asp Ile Val Val Cys Met Asp Gly Asp Thr
        900                 905                 910
Met Pro Gly Leu Phe Ala Tyr Lys Ala Ala Thr Lys Ala Gly Tyr Cys
    915                 920                 925
Gly Gly Ala Val Leu Ala Lys Asp Gly Ala Glu Thr Phe Ile Val Gly
930                 935                 940
Thr His Ser Ala Gly Gly Asn Gly Val Gly Tyr Cys Ser Cys Val Ser
945                 950                 955                 960
Arg Ser Met Leu Leu Lys Met Lys Ala His Ile Asp Pro Glu Pro His
            965                 970                 975
His Glu

<210> SEQ ID NO 33
<211> LENGTH: 2937
<212> TYPE: DNA
<213> ORGANISM: Artificial sequence
<220> FEATURE:
<223> OTHER INFORMATION: codon modified fusion protein

<400> SEQUENCE: 33
atggactaca aagacgacga cgacaaaggt gctggtcaat catcacctgc tacaggttca    60
caaaaccaat caggtaacac aggttcaatc atcaacaact actacatgca acaataccaa   120
aactcaatgg acacacaact gggtgacaac gctatctcag gtggttcaaa cgaaggttca   180
```

-continued

```
acagacacaa catcaacaca cacaacaaac acacaaaaca acgactggtt ctcaagactg    240
gcttcatcag ctttctcagg tctgttcggt gctctgctgg ctgacaaaaa aacagaagaa    300
acaacactgc tggaagacag aatcctgaca acaagaaacg gtcacacaac atcaacaaca    360
caatcatcag tgggtgtgac atacggttac gctgtgacag aagacgctgt gtcaggtcct    420
aacacatcag gtctggaaac aagagtgaca caagctgaaa gattcttcaa aaaacacctg    480
ttcgactgga cacctaacct ggctttcggt cactgccact acctggaact gcctacagaa    540
cacaaaggtg tgtacggttc actgatggac tcatacgctt acatgagaaa cggttgggac    600
atcgaagtga cagctgtggg taaccaattc aacggtggtt gcctgctggt ggctctggtg    660
cctgaactga agaactggga cacaagacaa aaataccaac tgacactgtt ccctcaccaa    720
ttcatcaacc ctagaacaaa catgacagct cacatcaacg tgcctttcgt gggtgtgaac    780
agatacgacc aatacgctct gcacaaacct tggacactgg tggtgatggt ggtggctcct    840
ctgacagtga aaacaggtgg ttcagaacaa atcaaagtgt acatgaacgc tgctcctaca    900
tacgtgcacg tggctggtga actgccttca aaagaaggta tcgtgcctgt ggcttgcgct    960
gacggttacg gtaacatggt gacaacagac cctaaaacag ctgaccctgt gtacggtaaa   1020
gtgttcaacc ctcctagaac aaacctgcct ggtagattca caaacttcct ggacgtggct   1080
gaagcttgcc ctacattcct gagattcggt gaagtgcctt tcgtgaaaac agtgaactca   1140
ggtgacagac tgctggctaa attcgacgtg tcactggctg ctggtcacat gtcaaacaca   1200
tacctggctg gtctggctca atactacaca caatactcag gtacaatgaa catccacttc   1260
atgttcacag gtcctacaga cgctaaagct agatacatgg tggcttacgt gcctcctggt   1320
atgacacctc ctacagaccc tgaaagagct gctcactgca tccactcaga atgggacaca   1380
ggtctgaact caaaattcac attctcaatc ccttacctgt cagctgctga ctacgcttac   1440
acagcttcag acgtggctga agctacatca gtgcaaggtt gggtgtgcat ctaccaaatc   1500
acacacggta aagctgaagg tgacgctctg gtggtgtcag cttcagctgg taaagacttc   1560
gaattcagac tgcctgtgga cgctagacaa caaacaacaa caacaggtga atcagctgac   1620
cctgtgacaa caacagtgga aaactacggt ggtgaaacac aaaacagtag aagactgcac   1680
acagacgtgg ctttcgtgct ggacagattc gtgaaattca cacctaaaaa cacacaaaca   1740
ctggacctga tgcaaatccc ttcacacaca ctggtgggtg ctctgctgag atcagctaca   1800
tactacttct cagacctgga aatcgctctg gtgcacacag gtcctgtgac atgggtgcct   1860
aacggtgctc ctaaaacagc tctggacaac caaacaaacc ctacagctta ccacaaacaa   1920
cctatcacaa gactggctct gccttacaca gctcctcaca gagtgctggc tacagtgtac   1980
aacggtaaaa caacatacgg tgaagaacct acaatgagag gtgacagagc tgtgctggct   2040
tcaaaagtga caaacaact gcctacatca ttcaactacg gtgctgtgaa agctgaaaac   2100
atcacagaaa tgctgatcag aatcaaaaga gctgaaacat actgccctag acctctgctg   2160
gctctggaca acacaagaga cagaagaaaa caagaaatca tcgctcctga aaaacaactg   2220
ctgaacttcg acctgctgaa actggctggt gacgtggaat caaaccctgg tcctttcttc   2280
ttctcagacg tgagatcagg tgctcctcct acagacctgc aaaaaatggt gatgggtaac   2340
acaaaacctg tggaactgat cctggacggt aaaacagtgg ctatctgctg cgctacaggt   2400
gtgttcggta cagcttacct ggtgcctaga cacctgttcg ctgaaaaata cgacaaaatc   2460
atgctggacg gtagagctat gacagactca gactacagag tgttcgaatt cgaaatcaaa   2520
gtgaaaggtc aagacatgct gtcagacgct gctctgatgg tgctgcacag aggtaacaga   2580
```

-continued

| | | | | | |
|---|---|---|---|---|---|
| gtgagagaca | tcacaaaaca | cttcagagac | gtggctagaa | tgaaaaaagg | tacacctgtg | 2640 |
| gtgggtgtga | tcaacaacgc | tgacgtgggt | agactgatct | tctcaggtga | agctctgaca | 2700 |
| tacaaagaca | tcgtggtgtg | catggacggt | gacacaatgc | ctggtctgtt | cgcttacaaa | 2760 |
| gctgctacaa | aagctggtta | ctgcggtggt | gctgtgctgg | ctaaagacgg | tgctgaaaca | 2820 |
| ttcatcgtgg | gtacacactc | agctggtggt | aacggtgtgg | gttactgctc | atgcgtgtca | 2880 |
| agatcaatgc | tgctgaaaat | gaaagctcac | atcgaccctg | aacctcacca | cgaataa | 2937 |

The invention claimed is:

1. An isolated nucleic acid comprising: a nucleic acid sequence of a virus that has undergone codon optimization for expression in *Bombyx mori* for the production of a vaccine against that virus in *Bombyx mori*, wherein the virus is influenza virus, type A, and the nucleic acid sequence encodes influenza virus HA protein which has been modified to attenuate the influenza virus HA protein by replacing the amino acid sequence of SEQ ID NO:7 with that of SEQ ID NO:8.

2. The isolated nucleic acid according to claim 1, wherein the virus is selected from the group consisting of subtypes H5 and H7.

3. The isolated nucleic acid according to claim 1, wherein the nucleic acid sequence is selected from the group consisting of SEQ ID NO: 4, SEQ ID NO: 12 and SEQ ID NO: 18.

4. A vector comprising the isolated nucleic acid according to claim 1.

5. A recombinant baculovirus produced using the vector according to claim 4.

6. A *Bombyx mori* comprising the recombinant baculovirus according to claim 5.

7. A *Bombyx mori* comprising the vector according to claim 4.

8. A *Bombyx mori* comprising: the isolated nucleic acid according to claim 1.

9. A method for producing a vaccine, the method comprising: obtaining the isolated nucleic acid according to claim 1, introducing the obtained nucleic acid according to claim 2 into *Bombyx mori* to express an encoded protein, and recovering the expressed protein from *Bombyx mori*.

10. A polypeptide comprising: an amino acid sequence encoded by the isolated nucleic acid according to claim 1.

11. A vaccine comprising: the polypeptide according to claim 10 for vaccinating an animal against a viral infection.

12. The vaccine according to claim 11, which has a virus-like particle structure.

13. The vaccine according to claim 12, wherein the diameter of the virus-like particle structure is 50 nm to 150 nm.

* * * * *